US008067566B2

(12) United States Patent
Kinney et al.

(10) Patent No.: US 8,067,566 B2
(45) Date of Patent: Nov. 29, 2011

(54) DENGUE SEROTYPE 2 ATTENUATED STRAIN

(75) Inventors: Richard Kinney, Fort Collins, CO (US); Claire Y. H. Kinney, Fort Collins, CO (US); Véronique Barban, Craponne (FR); Jean Lang, Mions (FR); Bruno Guy, Lyons (FR)

(73) Assignees: Sanofi Pasteur, Lyons (FR); Centers for Disease Control and Prevention, Atlanta, GA (US)

( * ) Notice: Subject to any disclaimer, the term of this patent is extended or adjusted under 35 U.S.C. 154(b) by 160 days.

(21) Appl. No.: 12/633,459

(22) Filed: Dec. 8, 2009

(65) Prior Publication Data

US 2010/0174057 A1 Jul. 8, 2010

Related U.S. Application Data

(62) Division of application No. 11/453,344, filed on Jun. 15, 2006, now Pat. No. 7,641,908.

(60) Provisional application No. 60/691,274, filed on Jun. 17, 2005.

(51) Int. Cl.
*A61K 39/12* (2006.01)

(52) U.S. Cl. .................................. 536/23.72; 424/218.1

(58) Field of Classification Search ........................ None
See application file for complete search history.

(56) References Cited

U.S. PATENT DOCUMENTS

2004/0137013 A1 7/2004 Katinger et al.

FOREIGN PATENT DOCUMENTS

| | | |
|---|---|---|
| EP | 1 159 968 | 12/2001 |
| WO | WO-96/40933 | 12/1996 |
| WO | WO-00/57907 | 10/2000 |
| WO | WO-02/095075 | 11/2002 |
| WO | WO-03/092592 | 11/2003 |

OTHER PUBLICATIONS

Kinney et al, "Development of new vaccine against dengue fever and Japanese encephalitis", 2001, pp. 176-197, vol. 44, Intervirology.

Kinney et al, "Construction of Infectious cDNA for Dengue 2 Virus: Strain 16681 and its attenuated Vaccine Derivative, Strain PDK-53", Apr. 14, 1997, pp. 300-308, vol. 230, No. 2, Academic Press Orlando, Florida, USA.

Butrapet et al, "Attenuation markers of a candidate dengue type 2 vaccine virus, strain 16681 (PDK-53), are defined by mutations in the 5' noncoding region and nonstructural proteins 1 and 3", Apr. 2000, pp. 3011-3019, vol. 74, No. 7, Journal of Virology, The American Society for Microbiology, USA.

Putnak et al, "Development of a purified, inactivated, dengue-2 virus vaccine prototype in vero cells: Immunogenicity and protection in mice and rhesus monkeys", Dec. 1996, pp. 1176-1184, vol. 174, No. 6, Journal of Infectious Diseases, Chicago, IL, USA.

Montagnon et al, "Experience with vero cells at Pasteur merieux connaught developments in biological standardization", 1997, pp. 137-140, vol. 98, Developments in Biological Standardization, Karger, Basel, CH.

*Primary Examiner* — Stacy B. Chen

(74) *Attorney, Agent, or Firm* — B. Aaron Schulman, Esq.; Terry L. Wright, Esq.; Stites & Harbison PLLC

(57) ABSTRACT

The invention relates to live attenuated VDV2 (VERO-Derived Vaccine Dengue serotype 2) strains which have been derived from the wild-type dengue-2 strain 16681 by passaging on PDK and Vero cells and nucleic acids thereof. The invention further relates to a vaccine composition which comprises a VDV2 strain.

4 Claims, 6 Drawing Sheets

```
Vero Working Cell Bank                    VDV2 passage 9
        │                                        │
        │ Cell cultivation      Virus inoculation on Vero cells
        │                       Virus cultivaton on Vero cells
        ▼                                        ▼
Vero cells suspension                    VDV2 passage 10
        │                                        │
        └────────────────┬───────────────────────┘
                         ▼
                   Crude Harvest
                         │
                         ▼
                  Clarified Harvest
                         │
                         ▼
                 Concentrated Harves
                         │
                         ▼
                   VDV2 passage 11
                     monovalent
                         │
                         ▼
                  Final Bulk Product
                     monovalent
                         │
                         ▼
                    Filled Product
                     monovalent
```

FIG.2

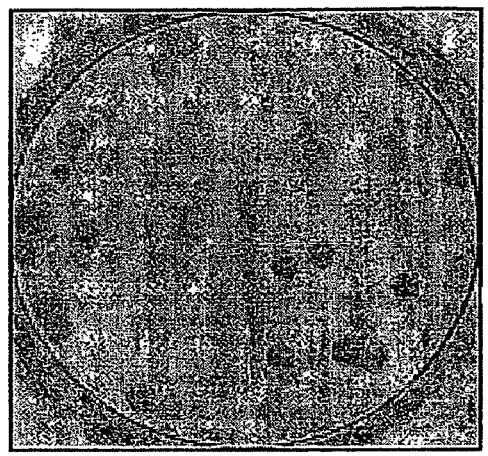
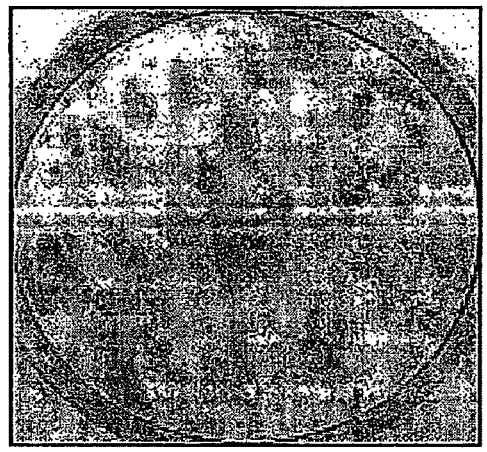
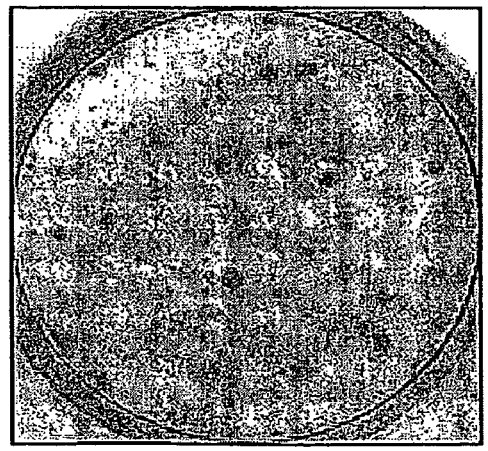
FIG.4

DENGUE SEROTYPE 2 ATTENUATED STRAIN

CROSS-REFERENCE TO RELATED APPLICATIONS

The present application is a divisional of U.S. application Ser. No. 11/453,344, filed Jun. 15, 2006, now U.S. Pat. No. 7,641,908 which claims the benefit of U.S. provisional application 60/691,274, filed on Jun. 17, 2005, incorporated herein by reference.

The invention relates to new live attenuated VDV2 (VERO-Derived Dengue serotype 2 virus) strains which are derived from the wild-type dengue-2 strain 16681 by passaging on PDK and Vero cells sanitization. The invention further relates to a vaccine composition which comprises such VDV2 strain.

Dengue diseases are caused by four closely related, but antigenically distinct, virus serologic types (Gubler, 1988; Kautner et al., 1997; Rigau-Perez et al., 1998; Vaughn et al., 1997), of the genus *Flavivirus* (Gubler, 1988). Infection with a dengue virus serotype can produce a spectrum of clinical illnesses ranging from a non-specific viral syndrome to severe, fatal haemorrhagic disease. The incubation period of dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Perez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

Dengue haemorrhagic fever (DHF) is a severe febrile disease characterised by abnormalities of homeostasis and increased vascular permeability that can lead to hypovolemia and hypotension (dengue shock syndrome, DSS) often complicated by severe internal bleeding. The case fatality rate of DHF can be as high as 10% without therapy, but below 1% in most centres with therapeutic experience (WHO Technical Guide, 1986).

Routine laboratory diagnosis of dengue infections are based on virus isolation and/or the detection of dengue virus-specific antibodies.

Dengue disease is the second most important tropical infectious disease after malaria, with over half of the world's population (2.5 billion) living in areas at risk for epidemic transmission. An estimated 50 to 100 million cases of dengue, 500,000 hospitalised DHF patients and 25,000 deaths occur each year. Dengue is endemic in Asia, the Pacific, Africa, Latin America, and the Caribbean. More than 100 tropical countries have endemic dengue virus infections, and DHF have been documented in more than 60 of these (Gubler, 2002; Monath, 1994). A number of well described factors appear to be involved in dengue infections: population growth, unplanned and uncontrolled urbanisation particularly in association with poverty, increased air travel, lack of effective mosquito control, and the deterioration of sanitary and public health infrastructure (Gubler, 2002). The awareness of dengue in travelers and expatriates is increasing (Shirtcliffe et al., 1998). Dengue has proven to be a major cause of febrile illness among US troops during deployments in dengue-endemic tropical areas (DeFraites et al., 1994).

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases, including some viruses belonging to the same genus as dengue (examples of commercially available flavivirus live-attenuated vaccines include yellow fever and Japanese encephalitis vaccines). The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotype 1 (strain 16007, passage 13), serotype 2 (strain 16681, passage 53=LAV2), and serotype 4 (strain 1036, passage 48) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3). These vaccines have been tested as monovalent (single serotype), bivalent (two serotypes), trivalent (three serotypes), and tetravalent (all four serotypes) vaccines in That volunteers. Those vaccines were found to be safe and immunogenic in children and in adults (Gubler, 1997). These LAV 1-4 strains have been described in EP 1159968 in the name of the Mahidol University and were deposited before the CNCM (CNCM I-2480; CNCM I-2481; CNCM I-2482 and CNCM I-2483 respectively).

The Den-2 strain 16681 was recovered from serum of a DHF (Dengue Hemorrhagic Fever) patient in Bangkok in 1964 (Halstead et al., 1970). The original viremic serum had been passaged 4 times on BSC-1 cells (African Green Monkey kidney cells) and 5 times on continuous LLC-MK.sub.2 cells (Rhesus Monkey kidney cells). In 1977, the virus was passaged once in vivo, in susceptible monkeys (*Macaca Mulatta*), and then again in LLC-MK.sub.2 cells. Two additional passages in mosquitoes (*Toxorhynchites amboinensis*) were conducted in 1980. Virus attenuation was performed by passages at 32.degree. C. on PDK cells (Primary Dog Kidney cells). Attenuation of the strain was checked according to several in vitro and in vivo markers. Passage 50 fulfilled all these attenuation criteria and was chosen as master seed for vaccine production (1982), at passage 53. DEN-2 PDK53 vaccine candidate was evaluated in humans and found to be strongly immunogenic with no untoward clinical signs and symptoms (Bhamarapravati et al., 1989).

The complete sequence of the Dengue 2 Live-Attenuated Virus strain (LAV2) was established by R. Kinney et al. (CDC, Fort Collins) in 2001. Sequence differences between parent DEN-2 strain 16681 (SEQ ID No.3) and LAV2 (SEQ ID No.38) strain are described in Table 1. Thus, genetic comparison of the wild-type virus strain 16681 and LAV2 strain showed a set of 9 point mutations which could be linked to LAV2 attenuation.

TABLE 1

DEN-2 16681 and DEN-2 16681/PDK53 (LAV2) Sequence Differences

| coordinates | | LAV2 | | 16681 | |
|---|---|---|---|---|---|
| Gene-aa | position | Nt | Aa | nt | aa |
| Non coding | Nt-57 | T | — | C | — |
| PrM-29 | Nt-524 | T | Val | A | Asp |
| E-373 | Nt-2055 | T | Phe | C | Phe |
| NS1-53 | Nt-2579 | A | Asp | G | Gly |
| NS2A-181 | Nt-4018 | T | Phe | C | Leu |
| NS3-250 | Nt-5270 | A/T | Val/Glu | A | Glu |
| NS3-342 | Nt-5547 | C | Arg | T | Arg |
| NS4A-75 | Nt-6599 | C | Ala | G | Gly |
| NS5-334 | Nt-8571 | T | Val | C | Val |

Nucleotide changes modifying the corresponding codon are indicated in bold.

The LAV2 strain which was initially established in 1983 was further rapidly identified as potential vaccine candidate (Bhamarapravati and Yoksan, 1997).

However, at that time, transmission to humans of Spongiform Encephalitis through mammalian cultures was not perceived as a risk and the virus was routinely maintained in Primary Dog Kidney cells (PDK). Furthermore, this LAV2 strain corresponds to a heterogeneous population. This heterogeneity represents an additional risk due to a potential in vitro or in vivo selection of one of the strain present in the composition.

In view of these increasing concerns, the Applicant decided to set up a sanitization process in order to get rid of any such risks. By transfecting Vero cells with the purified genomic RNA of LAV2, followed by three cycles of amplification in Vero cells, and two successive steps of virus plaque purification the Applicant produced a new Vero-Derived serotype 2 virus (VDV2).

This new VDV2 strain which has been thus derived by transfer to VERO cells and biological cloning differs from the LAV2 strain by sequence, an homogenous plaque size and temperature sensitivity but importantly has conserved some phenotypic and genotypic features of the LAV2 such as e.g. attenuation spots, small plaque phenotype, growth restriction at high temperature and has conserved the immunogenic features of the LAV2 strains. These features make this new strain a valuable vaccine candidate for prophylactic immunization in humans.

DEFINITIONS

"Dengue viruses" are positive-sense, single-stranded RNA viruses belonging to the *Flavivirus* genus of the flaviridae family. In the case of dengue serotype 2 (DEN-2) strain 16681, the entire sequence is 10723 nucleotides long (SEQ ID No.3). The RNA genome contains a type I cap at the 5'-end but lacks a 3'-end poly (A)-tail. The gene organization is 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The viral RNA genome is associated with the C proteins to form nucleocapsid (icosahedral symmetry). As with other flaviviruses, the DEN viral genome encodes the uninterrupted open reading frame (ORF) which is translated to a single polyprotein.

Serial passaging of a virulent (disease-causing) strain of dengue-2 results in the isolation of modified virus which are "live attenuated", i.e., infectious, yet not capable of causing disease. These modified viruses are usually tested in monkeys to evaluate their attenuation. However, Humans are the only primates that exhibit signs of clinical disease. The viruses that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response are called "live attenuated".

The term "LAV" denotes live attenuated Dengue viral strains. In the context of the invention "LAVs" are live attenuated strains initially derived from the Dengue serotype 2 (DEN-2) strain 16681 by passages in Primary Dog Kidney (PDK) Cells. For instance "LAV2/PDK53" is the attenuated strain established after 53 passages of strain 16681 in PDK cells (DEN-2 16681/PDK53). "LAV2/PDK50" is the attenuated strain established after 50 passages of strain 16681 in PDK cells (DEN-2 16681/PDK50). LAV2/PDK53 nucleotide sequence is shown in SEQ ID No.38.

"VDV2" is meant a LAV obtainable by the sanitization process disclosed in the present application. A VDV2 is thus a biological clone (homogeneous) VERO-adapted Dengue serotype 2 virus capable of inducing a specific humoral immune response including neutralizing antibodies in primate especially in humans. The VDV2 strains of the invention can be easily reconstructed starting directly from the here disclosed VDV2 sequences. The induction of a specific humoral immune response can be easily determined by an ELISA assay. The presence of neutralising antibody in the serum of a vaccinee is evaluated by the plaque reduction neutralization test as described in section 4.1.1.2.2. A serum is considered to be positive for the presence of neutralizing antibodies when the neutralizing antibody titer thus determined is at least superior or equal to 1:10.

The terms "mutation" means any detectable change in genetic material, e.g. DNA, RNA, cDNA, or any process, mechanism, or result of such a change. Mutations include substitution of one or more nucleotides. In the context of the instant application, mutations identified in dengue-2 virus genomic sequence or polyprotein are designated pursuant to the nomenclature of Dunnen and Antonarakis (2000). As defined by Dunnen and Antonarakis at the nucleic acid level, substitutions are designated by ">", e.g. "31A>G" denotes that at nucleotide 31 of the reference sequence a A is changed to a G.

Variations at the protein level describe the consequence of the mutation and are reported as follows. Stop codons are designated by X (e.g. R97X denotes a change of Arg96 to a termination codon). Amino acid substitutions a designated for instant by "S9G", which means that Ser in position 9 is replaced by Gly.

VERO-Derived Dengue Serotype 2 Viruses (VD V2)

The composition of the previously developed dengue-2 vaccine candidate LAV2 was improved by a sanitization process.

The VERO-Derived Vaccine Dengue serotype 2 (VDV2) disclosed herein uses the DEN-2 16681 virus attenuated by serial passages on PDK cells. VDV2 contains the genomic sequence of the whole live-attenuated DEN-2 virus, and bears the same attenuation spots which have been linked to attenuation as the original LAV2 strain that was tested in humans.

Sanitization of the LAV2 vaccine was performed by removing proteins and introducing only purified viral genomic material into Vero cells. More specifically, sanitization of the strain was performed by purifying and transfecting viral RNA into Vero cells. The process comprises the following steps:

a) extracting and purifying viral RNA from plaque-purified LVA2 strain, e.g. DEN-2 16681/PDK50 viruses;
b) advantageously associating of the purified RNA with cationic lipids;
c) transfecting Vero cell, in particular Vero cell LS10;
d) recovering of the neo-synthesized virus; and
e) purifying a VDV strain by plaque purification and optionally amplifying it in host cells, especially Vero cells.

The Vero cell technology is a well-known technology which has been used for different commercial products (injectable and oral polio vaccines, rabies vaccine). In the present invention qualified Vero cells were advantageously used to guarantee the absence of any risks potentially linked to the presence of adventitious agents. By "qualified VERO cells" is meant cells or cell lines for which culture conditions are known and is such that the said cells are free from any adventitious agents. These include e.g. the VERO cell LS10 of Sanofi Pasteur.

The thus isolated VDV strains are classically stored either in the form of a freezed composition or in the form of a lyophilised product. For that purpose, the VDV can be mixed with a diluent classically a buffered aqueous solution comprising cryoprotective compounds such a sugar alcohol and stabilizer. The pH before freezing or lyophilisation is advantageously settled in the range of 6 to 9, e.g. around 7 such as a pH of 7.5.+−.0.2 as determined by a pH meter at RT. Before use, the lyophilised product is mixed with a pharmaceutically diluent or excipient such as a sterile NaCl 4% solution to reconstitute a liquid immunogenic composition or vaccine.

The Glu variant of LAV2 vaccine strain, at position NS3-250, was selected during transfection and cloning, and positions 5'NC-57 and NS1-53, also identified as critical for attenuation of LAV2 vaccine, were both conserved in VDV2 sequence.

Sequencing, at attenuation-specific loci, of virus recovered after transfection, did not reveal any mutation, compared to SEQ ID No.38. The biologically cloned VDV2 virus exhibits a homogenous plaque phenotype and a remarkable genetic stability with regard to its LAV2 parent as it can be deduced especially from the conservation of the attenuation genotype.

VDV2 (passage 11) strain was sequenced and compared with the serotype 2 Dengue Live Attenuated Virus (LAV2) strain sequence (SEQ ID No.38). A set of 10 nucleotide differences was identified, triggering six amino acid substitutions located in M and Env structural peptides, and also in non-structural peptides NS3 and NS5. None of these differences corresponds to any of the LAV2 attenuation positions.

TABLE 2

Sequence comparison between LAV2/PDK53 and VDV2 passage 11 strains.

| Nucleotides | | | Amino Acids | | |
|---|---|---|---|---|---|
| Position | LAV2 | VDV2 | Region Position | LAV2 | VDV2 |
| 736 | G | C | M 9 | G | R |
| 1619 | G | A | F 228 | G | F |
| 1638 | A | G | E 234 | K | K |
| 2520 | G | A | NS1 33 | K | K |
| 4723 | T | A | NS3 69 | S | T |
| 5062 | G | C | NS3 181 | D | H |
| 9191 | G | A | NS5 541 | R | K |
| 9222 | A | G | NS5 551 | E | E |
| 10063 | T | A | NS5 832 | S | T |
| 10507 | A | G | 3'nc | — | — |

Grey shading: differences in structural proteins; Bold characters: differences in non-structural proteins.

The invention thus provides for live attenuated dengue-2 virus strains that have been obtained from the wild type virus DEN-2 16681 attenuated by serial passages on PDK cells and then by sanitization on VERO cells. In particular the attenuated strains of the invention comprise at least the identified sequence mutations (non-silent and optionally silent) relative to the nucleotide sequence or polyprotein sequence of the wild-type DEN-2 16681 and LAV2/PDK53 strains.

Accordingly, the invention relates to an isolated live attenuated dengue-2 virus strain which comprises, or consists of, the sequence of LAV2/PDK53 strain (SEQ ID No. 38) wherein at least nucleotides at positions 736, 1619, 4723, 5062, 9191, 10063, and 10507, and optionally 1638, 2520, 9222, and 10361, are mutated, with the proviso that the following nucleotides are not mutated: 57, 524, 2055, 2579, 4018, 5547, 6599, and 8571. Preferably, the mutations are substitutions. Preferably, the nucleotide at position 736 is C, the nucleotide at position 1619 is A, the nucleotide at position 4723 is A, the nucleotide at position 5062 is A, the nucleotide at position 9191 is A, the nucleotide at position 10063 A, and the nucleotide at position 10507 is G. The nucleotide at position 5270 may be A or T, preferably A.

Still preferably, the isolated strain according to the invention comprises the sequence SEQ ID No.38 wherein said sequence comprises at least the mutations 736 G>C, 1619 G>A, 4723 T>A, 5062 G>C, 9191 G>A, 10063 T>A, and 10507 A>G, and optionally the mutation 1638 A>G, 2520 G>A, and/or 9222 A>0.

Hence, a live attenuated dengue-2 virus strain according to the invention may comprise, or consist of, the sequence of wild-type dengue-2 strain 16681 (SEQ ID No.3) wherein said sequence comprises at least the mutations 57 C>T, 524 A>T, 736 G>C, 1619 G>A, 2055 C>T, 2579 G>A, 4018 C>T, 4723 T>A, 5062 G>C, 5547 T>C, 6599 G>C, 8571 C>T, 9191 G>A, 10063 T>A, and 10507 A>G. Preferably, a live attenuated strain according to the invention further comprises the mutation 1638 A>G, 2520 G>A, and/or 9222 A>G by reference to the nucleotide sequence of wild-type strain 16681 (SEQ ID No.3).

The live attenuated dengue-2 virus strains according to the invention may include variant strains that comprise a sequence SEQ ID No.38 mutated at positions 736, 1619, 4723, 5062, 9191, 10063, and 10507, as defined above, and that further comprise a substitution of one or more nucleotides in a given codon position that results in no alteration in the amino acid encoded at that position.

Advantageously, the live attenuated dengue-2 virus strain according to the invention comprises a sequence which differs by a limited number of mutations, e.g. no more than 5, still preferably no more than 2, from SEQ ID No.1.

Preferably, the genomic sequence of a dengue-2 virus strain according to the invention consists of the nucleotide sequence SEQ ID No.1.

The invention also relates to live attenuated dengue-2 strains that may be derived from the VDV2 strain of sequence SEQ ID No.1 by further passages on cells, in particular Vero cells.

The invention also relates to an isolated nucleic acid which comprises, or consists of, the DNA sequence SEQ ID No.1 or its equivalent RNA sequence.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, by RNA sequence "equivalent" to SEQ ID No.1 is meant a sequence SEQ ID No.1 wherein deoxythymidines have been replaced by uridines. As SEQ ID No.1 constitutes VDV2 cDNA sequence, the equivalent RNA sequence thus corresponds to the positive strand RNA of VDV2.

The invention further relates to the polyprotein of sequence SEQ ID No.2 and to fragments thereof. SEQ ID No.2 is the sequence of the polyprotein encoded by SEQ ID No.1 A "fragment" of a reference protein is meant a polypeptide which sequence comprises a chain of consecutive amino acids of the reference protein. A fragment may be at least 8, at least 12, at least 20, amino acid long.

Said fragments of the polyprotein of sequence SEQ ID No.2 comprise at least an arginine at position 9 of M protein (position 214 of SEQ ID No.2), and/or a glutamic acid at position 228 of E protein (position 508 of SEQ ID No.2), and/or a threonine at position 69 of NS3 protein (position 1543 of SEQ ID No.2), and/or a histidine at position 181 of NS3 protein (position 1656 of SEQ ID No.2), and/or a lysine at position 541 of NS5 protein (position 1725 of SEQ ID No.2), and/or a threonine at position 832 of NS5 protein (position 3032 of SEQ ID No.2).

According to an embodiment the fragment of the polyprotein encoded by SEQ ID No.1 is or comprises M protein, and/or E protein, and/or NS3 protein and/or NS5 protein.

Immunogenic and Vaccine Compositions

The invention also relates to an immunogenic composition, suitable to be used as a vaccine, which comprises a VDV2 strain according to the invention.

The immunogenic compositions according to the invention elicit a specific humoral immune response toward the dengue virus comprising neutralizing antibodies.

Preferably, the immunogenic composition is a vaccine.

According to an embodiment, the immunogenic is a monovalent composition, i.e. it elicits en immune response and/or confers protection against Dengue-2 virus only.

According to another embodiment, the invention relates to a multivalent dengue immunogenic composition. Such a multivalent immunogenic composition or vaccine may be obtained by combining individual monovalent dengue vaccines. The immunogenic or vaccine composition may further comprise at least a live attenuated dengue virus of another serotype. In particular, the immunogenic or vaccine composition may comprise a VDV2 according to the invention in combination with at least a live attenuated dengue virus selected from the group consisting of serotype 1, serotype 3, and serotype 4.

Preferably, the immunogenic or vaccine composition may be a tetravalent dengue vaccine composition, i.e. a vaccine composition that comprises a VDV2 according to the invention in combination with a live attenuated dengue-1 virus strain, a live attenuated dengue-3 virus strain and a live attenuated dengue-4 virus strain.

Live attenuated dengue-1, dengue-3 and dengue-4 virus strains have been described previously. Reference may be made to the live-attenuated vaccines that were developed by Mahidol University by passaging dengue serotype 1 (strain 16007, passage 13; LAV1), and serotype 4 (strain 1036, passage 48, LAV4) viruses in Primary Dog Kidney (PDK) Cells, and for serotype 3 (strain 16562) in Primary Green Monkey Kidney (PGMK) cells (passage 30) and Fetal Rhesus Lung (FRhL) cells (passage 3) (LAV3). The nucleotide sequences of LAV1 (SEQ ID No.40), LAV3 (SEQ ID No.41), and LAV4 (SEQ ID No.42) are shown in the annexed sequence listing.

Advantageously, a live attenuated dengue-1 strain may correspond to a VDV1 strain which has been obtained from the LAV1 strain developed by Mahidol by the process of sanitization according to the invention. In particular a live attenuated dengue-1 strain (VDV1) may comprise, and advantageously consists of the sequence SEQ ID No.39.

Immunogenic compositions including vaccines may be prepared as injectables which can correspond to liquid solutions, suspensions or emulsions. The active immunogenic ingredients may be mixed with pharmaceutically acceptable excipients which are compatible therewith.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Preferably, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the VDV2 strain. Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a dengue infection which comprises administering the host with an immunoeffective amount of a vaccine composition according to the invention.

A "host in need thereof" denotes a person at risk for dengue infection, i.e. individuals travelling to regions where dengue virus infection is present, and also inhabitants of those regions.

The route of administration is any conventional route used in the vaccine field the choice of administration route depends on the formulation that is selected preferably, the immunogenic composition or vaccine corresponds to an injectable composition administered via subcutaneous route, advantageously in the deltoid region.

The amount of LAV or VDV, in particular VDV2, in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or $10^3$ to $10^5$ $CCID_{50}$ of LAV or VDV, for instance a dose of $4\pm0.5$ $\log_{10}$ $CCID.sub._{50}$ of VDV2 strain for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee, as evaluated by the plaque reduction neutralization test as described in section 4.1.1.2.2; a serum being considered to be positive for the presence of neutralizing antibodies when the neutralizing antibody titer thus determined is at least superior or equal to 1:10.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naive as well as well as non-naive with regards to dengue virus. The vaccines of the invention can be administered in a single dose or, optionally, administration can involve the use of a priming dose followed by a booster dose that is administered, e.g. 2-6 months later, as determined to be appropriate by those of skill in the art. The invention will be further described in view of the following figures and examples.

FIGURES

FIG. 2 is a flow chart that summarises the developed manufacturing process that gives rise to the Filled Product (monovalent), "ready to use" doses.

Figure 1:
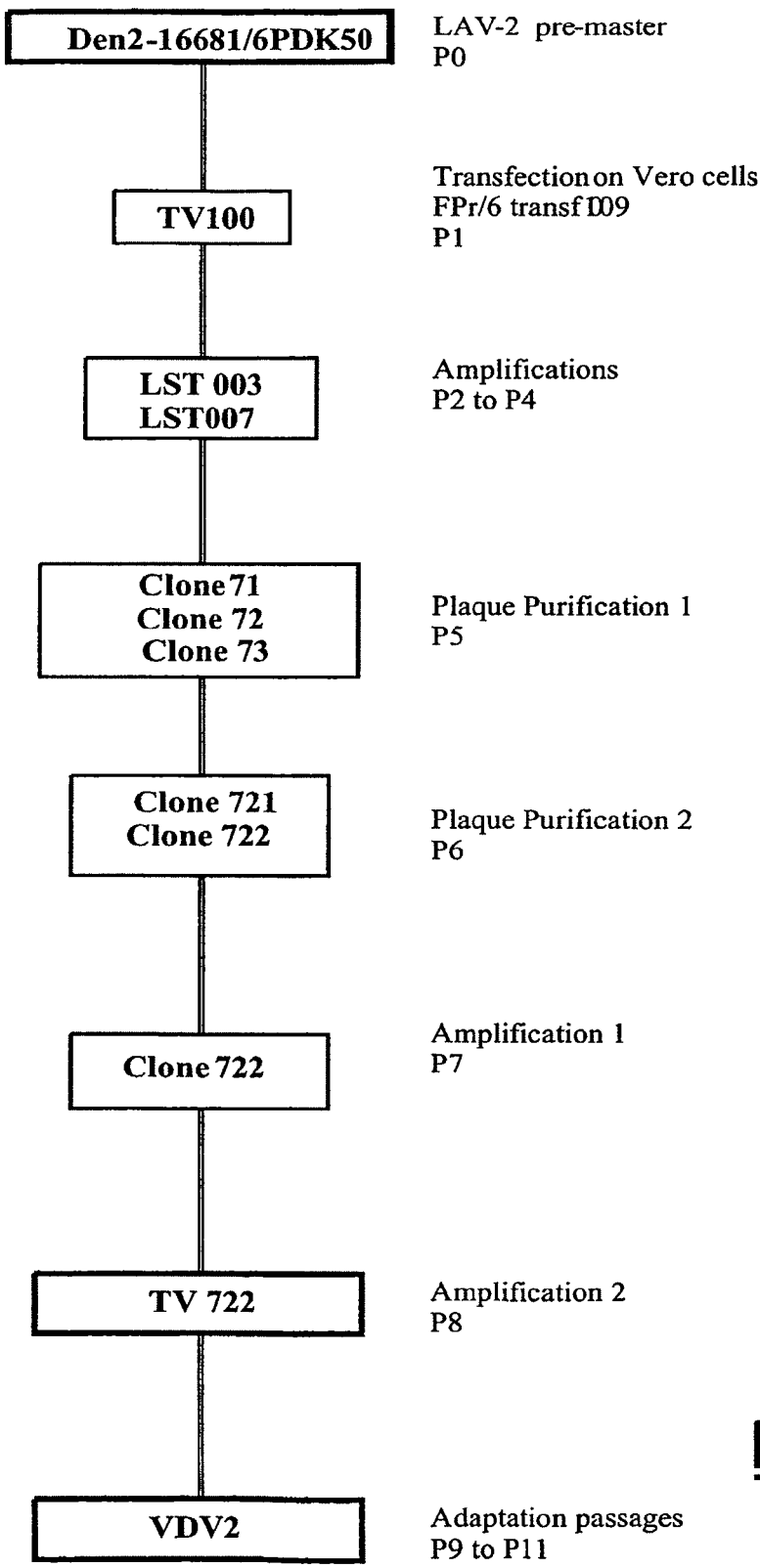
FIG. 1 is a summary of History of VDV2 seed.
Figure 3:
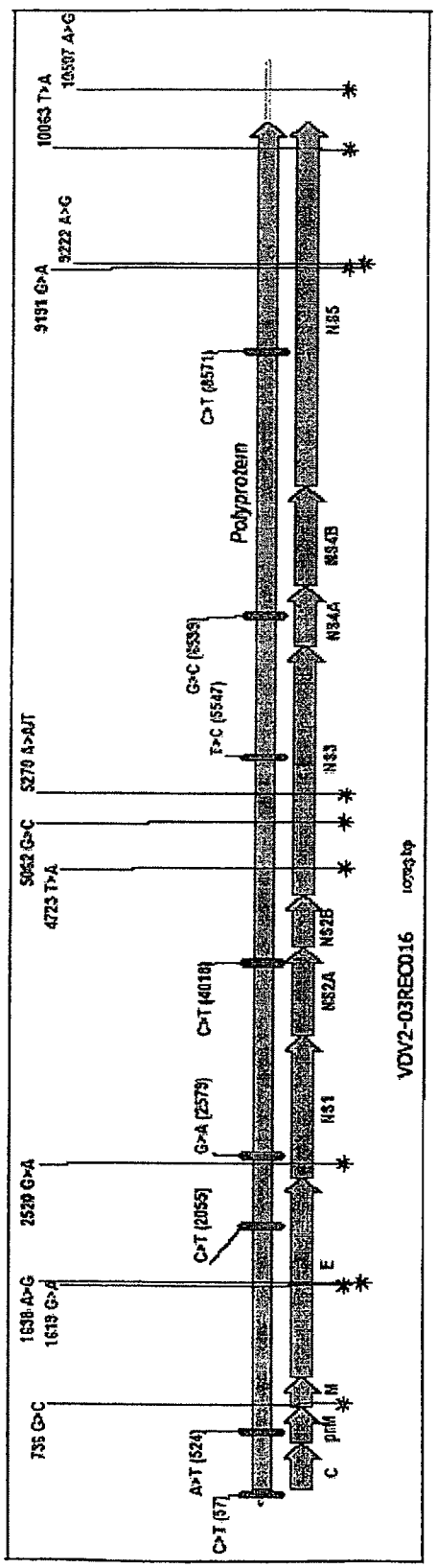

FIG. 3 is a diagrammatic representation of VDV2 genome map. The above arrow is the polyprotein coding sequence. The below arrows represent mature peptides coding sequence. The vertical bars symbolize the nucleotidic variations between wild-type dengue 2 strain 16681 and LAV2 strain. The stars designate the nucleotidic variations between LAV2 and VDV2.

FIG. 4 shows plaque size analysis after 7 days of incubation at 37° C. for dengue-1 viruses LAV2, VDV2, and strain 16681.

Figure 5:
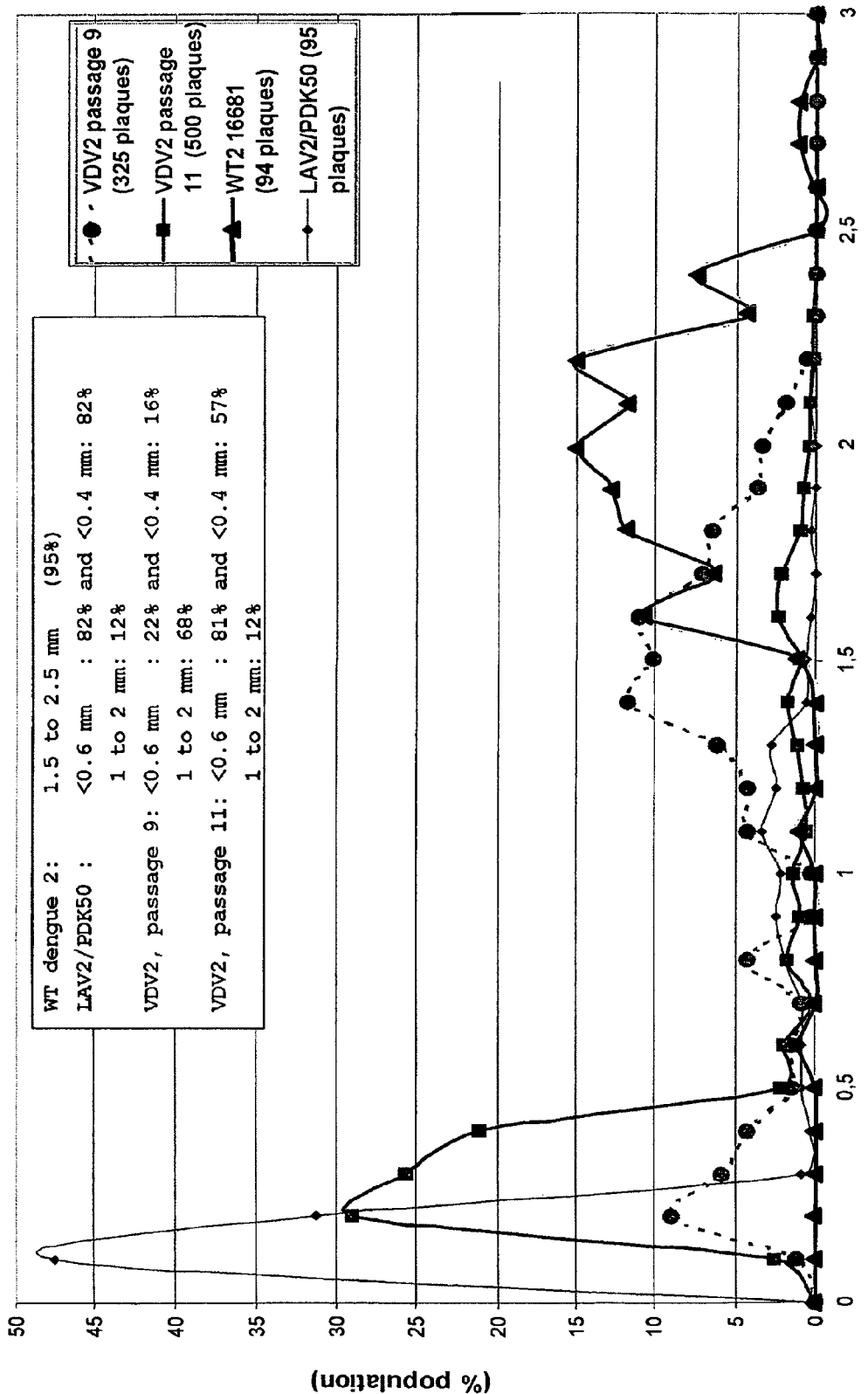

FIG. 5 is a graphic analysis showing plaque size distribution for dengue-2 viruses LAV2, VDV2, and strain 16681.

Figure 6:
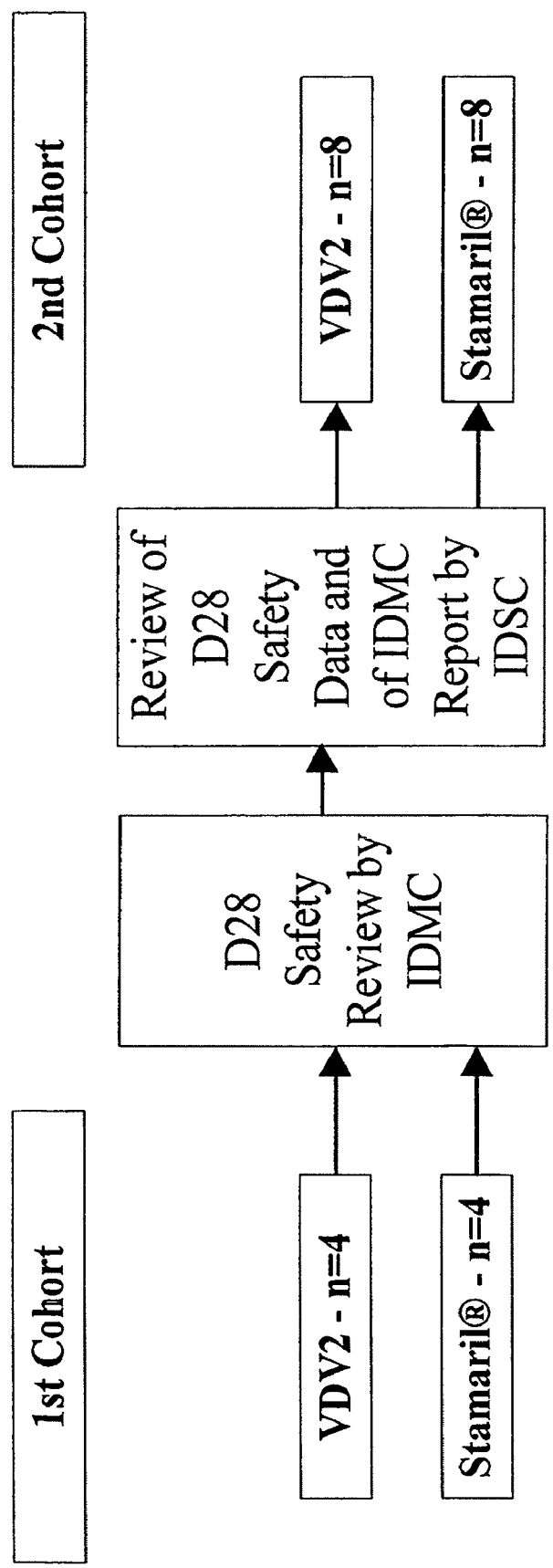

FIG. 6 is a summary of Trial Design for assessment of safety of VDV2 monovalent in healthy flavivirus-naive adults.

EXAMPLES

Example 1

Sanitization 1.1 Viral RNA Purification

The RNA purification and transfection process was performed as follows. DEN-2/PDK50 suspension was resuspended in 0.5 ml of water and diluted in order to contain at least $3\times10^4$ and up to $3\times10^7$ $TCID_{50}$ or PFU of virus per milliliter. One unit of benzonase diluted in 0.01 ml of William's medium was added to 0.5 ml of virus, in order to digest DNA or RNA molecules from cellular origin, and the solution was incubated for 2 hours at 4° C. on an agitator. At the end of incubation step, 0.65 ml of a denaturing buffer containing guanidium chloride, detergent (SDS), and pmercaptoethanol (RTL-.beta.mercaptoethanol buffer, provided in the kit RNeasy Mini kit, Qiagen Ref. 74104) were added and proteins were extracted once with phenol/chloroform (1/1) vol/vol and once with chloroform vol/vol, followed by centrifugation for 5 min at 14,000 rpm at room temperature. After each extraction, the aqueous phase was collected, taking care not to collect material (white precipitate) at the interface, and transferred to a clean 1 ml-Eppendorf tube. The RNA solution was then applied onto a QIAgen column following the recommendations of the manufacturer (RNeasy minikit, QIAgen), in order to remove traces of solvent, and eluted with 0.06 ml of nuclease-free $H_2O$ water. The presence of viral RNA was confirmed by quantitative RT-PCR, using a reference curve established with known quantities of virus, in $TCID_{50}$/ml.

1.2 Transfection of Vero Cells with Purified RNA

Transfection was performed using lipofectamine (LF2000 Reagent, Life Technologies), a mixture of cationic lipids that associate to RNA through charge interactions and allows transfer of the complexes into the cytoplasm of the cells by fusion with the cell membrane. The optimal quantity of LF2000 reagent was determined in a preliminary experiment by incubating Vero cells, plated 16 to 24 hours before (0.3-$0.5\times10.sup.^6$ cells per well in a 6 wells plate) with increasing doses (5 to 20 µl) of lipofectamine. Cells were then incubating 4 to 5 hours at 32° C., 5% $CO_2$, before replacing the medium by fresh culture medium without FCS, and the incubation was continued overnight at 32° C. Toxicity (round, refringent or floating cells, homogeneity of the cell monolayer) was checked regularly for 48 hours, under an inverted microscope. The highest dose of lipofectamine that was not toxic under these conditions was 10 µl and was chosen for RNA transfection.

Four transfections were carried out in parallel, using ¼ of the RNA preparation (about $2\times10^4$ log $eqTCID_{50}$, according to qRT-PCR). Twenty-five microliters of viral RNA solution were diluted in 500 .mu.l of OptiMEM medium (GIBCO) containing 15 .mu.l of LF2000 Reagent (a mixture of cationic lipids that associate to RNA through charge interactions, and allow transfer of the complexes into the cytoplasm of the cells by fusion with the cell membrane). 200 ng of yeast tRNA were added as carrier in 2 out of the 4 reactions.

The 4 transfection mixes were allowed to precipitate for 10 min at room temperature before addition to 6-wells plates of confluent Vero cells, and incubation at 36.degree. C. After four hours, transfection mix was removed and cells were rinsed once in PBS. Three milliliters of post-transfection medium (Williams, GIBCO) were added, and incubation was continued for 5 days at 32° C. Culture medium was then replaced by 3 ml of Dengue infection medium (Williams supplemented with 10 mM $MgSO_4$).

A focus of cells presenting typical cytopathic effects (round, refringent cells) was detected at day 8 post-transfection in 1 out of the 2 wells transfected in presence of tRNA. Release of virus in the supernatant of these cells was confirmed by qRT-PCR. Eleven days post-transfection, marked cytopathic effects were detected in this only well, while the supernatant of the three other transfected-wells remained negative.

The viral solution recovered after transfection was re-named TV100 (instead of 16681 PDK50Nero-2) and exhibited an infectious titer of 5.8 log $TCID_{50}$/ml after dilution at ½ in an aqueous buffered solution comprising cryoprotective agents (pH=7.5).

1.3 Characterization of Viruses Recovered After Transfection

Spot sequencing of specific loci important for attenuation was performed by R. Kinney (CDC, Fort Collins). Data are presented in Table 3.

TABLE 3

Sequencing of transfected virus at attenuation-specific positions

| Virus | 5'-NC-57 Nt 57 | NS1-53 Nt 2579 (aa) | NS3-250 Nt 5270 (aa) |
|---|---|---|---|
| DEN-2 16681 | C | G (Gly) | A (Glu) |
| DEN-2 PDK53 | T | A (Asp) | T/A (Val/Glu) |
| TV100 | T | A (Asp) | A (Glu) |

VDV2 has retained the important attenuating loci at 5'NC-57 and NS1-53, and the wild-type 16681 locus of the NS3-250-Glu variant in the PDK53 vaccine. The NS3-250-GluNal mix in the PDK53 vaccine was observed to be stable between passages PDK45 and PDK53 suggesting that selection has occurred in Vero cells. Previous analysis of DEN-2 vaccine isolated from serum of a vaccinee had demonstrated that this selection could also occur in humans.

Viral plaques diameters were measured in Vero cells. Briefly, Vero cells were plated at a density of 1.000.000 cells/$cm^2$ in culture medium containing 4% of FBS. After overnight incubation, the medium was removed and cells were infected with serial twofold or fivefold dilutions of virus. After 1.5 hour at 37° C. 5% $CO_2$, the inoculum was removed and cells were incubated at 37° C. 5% $CO_2$ in Minimal Eagle Medium (MEM) containing 1.26% methylcellulose and 10% FBS. After 11 days of incubation, plates were fixed 20 minutes in cold acetone at −20° C. and revealed by immunocoloration with a flavivirus-specific mAb, diluted at 2.5 μg/ml. Viral plaques were measured using an image analysis software (Saisam/Microvision). VDV2 was compared to LAV2 16681/PDK50 seed (Table 4) and exhibited similar homogeneous small plaques of 1-3 mm diameter.

TABLE 4

Plaques size of LAV2 16681/PDK50 and VDV2

| Step | Virus | LP/MP | SP |
|---|---|---|---|
| Before transfection | LAV2 PDK50 | 0 | 319 |
| After transfection | Uncloned VDV2 | 0 | 183 |

LP/MP: Number of Large/Medium Plaques in 6 wells
SP: Number of Small Plaques in 6 wells 1.4 Plaque-Purifications Three additional amplification passages (P2 to P4) were performed on the virus recovered after transfection. Biological cloning by plaque-purification was performed on P3 and P4 passaged virus (named LST 003 and LST 007, respectively).

Briefly, Vero cells were plated in 6-well plates and infected with serial dilutions of virus, in order to get between 1 and 20 plaques by plate. After 1.5 hour at 37° C. 5% $CO_2$, the inoculum was removed and cells were incubated under 3 ml of solid medium composed of MEM-10% FCS pre-heated at 42° C. and mired extemporaneally with 2% of melted agarose equilibrated at 42° C. The medium was allowed to solidify at room temperature for 30 min; under flow hood, and plates were incubated in inverted position for 10 days at 32° C.-5% CO.sub.2. A second layer of the same medium supplemented with 0.01% of neutral red was then added and plates were incubated for an additional night at 32° C. Six well-isolated small plaques were picked under sterile conditions using a micro-pipet equipped with an 0.1 ml tip, and transferred into sterile tubes containing 0.2 ml of MEM4% FCS: three from P3 passage (identified as clones 31, 32 and 33), and three from P4 passage (identified as clones 71, 72 and 73). The suspension was homogenised by vortexing, serially diluted in the same medium, and immediately used to infect 6-well plates of Vero cells. The protocol was repeated and a second picking of two SP was done on clones 32, 33, 71 and 72, and one SP on clone 31. Each picked plaque was diluted in 1 ml of medium, before amplification on Vero cells, in T25 cm.sup.2 flasks. Culture medium was collected at day 6 post-infection, diluted with the same volume of an aqueous buffered solution comprising cryoprotective agent (pH 7.5) and frozen at −70° C. All these steps were performed at 32° C.

Plaque purified virus were named 311, 321, 322, 331, 332, 341, 342, 351, 352, 711, 712, 721 and 722, respectively.

Infectious titers were determined on Vero cells at the end of the first amplification (see below)

Clone 311: 3.95 Log$CCID_{50}$/ml

Clone 321: 5.20 Log$CCID_{50}$/ml Clone 322: 5.45 Log$CCID_{50}$/ml

Clone 331: 5.55 Log$CCID_{50}$/ml Clone 332: 4.95 Log$CCID_{50}$/ml

Clone 341: 2.80 Log$CCID_{50}$/ml Clone 342: 4.85 Log$CCID_{50}$/ml

Clone 351: 5.35 Log$CCID_{50}$/ml Clone 352: 5.50 Log$CCID_{50}$/ml

Clone 711: 5.45 Log$CCID_{50}$/ml Clone 712: 5.65 Log$CCID_{50}$/ml

Clone 721: 5.30 Log$CCID_{50}$/ml Clone 722: 5.60 Log$CCID_{50}$/ml

A second amplification on Vero cells was carried out for three clones: clones 331, 352, and 722. Culture supernatants were collected at day 8 post-infection, diluted at ½ with an aqueous buffered solution comprising cryoprotective agent (pH 7.5) and named TV331, TV352 and TV722.

1.5 Characterization of Cloned Virus

After the $1^{st}$ amplification, all amplified viruses exhibited same plaque size phenotype and titers equivalent to, or higher than 5 log$CCID_{50}$/ml (except clones 311 and 341 which were significantly lower). Sequencing at attenuation-specific positions was performed on 6 clones from the $1^{st}$ amplification (clones 321, 331, 351, 352, 711, 721) and the three clones from the $2^{nd}$ amplification, and revealed no mutation.

In absence of any significant difference between the clones, TV722 was selected and amplified in VERO cells in order to generate a VDV2 vaccine candidate strain.

TABLE 5

Sequencing at attenuation-specific spots of DEN-2 viruses

| Step/cell | Virus | 5'-UTR | prM | E | NS1 | NS2a | NS3 | | NS4A | NS5 |
|---|---|---|---|---|---|---|---|---|---|---|
| | | 57 | 524 | 2055 | 2579 | 4018 | 5270 | 5547 | 6599 | 8571 |
| Wild-type/PGMK | 16681 | C | A | C | G | C | A | T | G | C |
| Vaccine/PDK | PDK53 | T | T | T | A | T | A/T | C | C | T |
| 2$^{nd}$plaque-purification/VERO | TV 321 | T | T | T | A | T | A | C | C | T |
| | TV 331 | T | T | T | A | T | A | C | C | T |
| | TV 342 | T | T | T | A | T | A | C | C | T |
| | TV 352 | T | T | T | A | T | A | C | C | T |
| | TV 711 | T | T | T | A | T | A | C | C | T |
| | TV 722 | T | T | T | A | T | A | C | C | T |
| 2$^{nd}$ amplification/VERO | TV 722PM | T | T | T | A | T | A | C | C | T |

Nucleotides position are indicated below each gene and referred to published sequence of DEN-2 16681 strain.

In conclusion, a total number of 11 passages was necessary to obtain a biological clone of DEN-2 166681/PDK50 adapted on VERO cells.

Further characterizations have been performed then by determining VDV2 passage 11 complete sequence and phenotypic testing.

Example 2

Sequencing

The complete sequence of the virus was generated according to the following strategy. Viral genomic RNA was purified. The full genome was amplified by 16 overlapping RT-PCR reactions. Each PCR was designed so that sequencing tags were added on each DNA strand. This allowed simpler sequence reactions, all driven by a single pair of universal sequencing primers. Each PCR product was individually sequenced on both DNA strands. All results were reassembled to reconstruct the full VDV2 genome.

2.1 Materials
2.1.1 Viruses

The viruses to which it is referred here are DEN-2 16681; LAV-2/PDK53; VDV2, the sequences of which are given in the attached sequence listing.

The complete genome sequence of these viruses is 10723 nucleotides in length.

2.1.2 Primers

All primers have been designed in Seqweb bioinformatics package (Accelrys), primer design module (Table 6).

TABLE 6 list of RT-PCT and sequencing primers

| Name | Primers sequences | | NtStart | NtEnd | Primer length | RT-PCR length | Overlap |
|---|---|---|---|---|---|---|---|
| D2 01+ | GTTTTCCCAGTCACGACacgtggaccgacaaagacag | (SEQ ID No. 4) | 13 | 32 | 37 | 978 | -32 |
| D2 01− | AACAGCTATGACCATGttcctcctgaaacccttcc | (SEQ ID No. 5) | 991 | 972 | 36 | | 371 |
| D2 02+ | GTTTTCCCAGTCACGACatcacgtacaagtgtccc | (SEQ ID No. 6) | 583 | 601 | 36 | 949 | |
| D2 02− | AACAGCTATGACCATGagcaacaccatctcattgaag | (SEQ ID No. 7) | 1532 | 1512 | 37 | | 163 |
| D2 03+ | GTTTTCCCAGTCACGACtgcaaccagaaaacttggaatacac | (SEQ ID No. 8) | 1325 | 1349 | 42 | 948 | |
| D2 03− | AACAGCTATGACCATGgctccatagattgctccaaagac | (SEQ ID No. 9) | 2273 | 2251 | 39 | | 203 |
| D2 04+ | GTTTTCCCAGTCACGACccagtcaacatagaagcagaacc | (SEQ ID No. 10) | 2025 | 2048 | 41 | 878 | |
| D2 04− | AACAGCTATGACCATGccaaagccatagtcttcaacttcc | (SEQ ID No. 11) | 2903 | 2880 | 40 | | 155 |
| D2 05+ | GTTTTCCCAGTCACGACatcatgcaggcaggaaaac | (SEQ ID No. 12) | 2707 | 2725 | 36 | 949 | |
| D2 05− | AACAGCTATGACCATGaccataaccatcactcttccc | (SEQ ID No. 13) | 3656 | 3636 | 37 | | 240 |
| D2 06+ | AACAGCTATGACCATGaccataaccatcactcttccc | (SEQ ID No. 14) | 33668 | 3386 | 36 | 930 | |
| D2 06− | AACAGCTATGACCATGgctctctccagttccaaatc | (SEQ ID No. 15) | 4298 | 4279 | 36 | | 146 |
| D2 07+ | GTTTTCCCAGTCACGACaagaaccagcaagaaaaggag | (SEQ ID No. 16) | 4113 | 4133 | 38 | 868 | |
| D2 07− | AACAGCTATGACCATGcaccattaccataaagacccac | (SEQ ID No. 17) | 4981 | 4960 | 38 | | 226 |
| D2 08+ | GTTTTCCCAGTCACGACttgaaccatcatgggcggac | (SEQ ID No. 18) | 4715 | 4734 | 37 | 910 | |
| D2 08− | AACAGCTATGACCATGtcctgcttttatacttggaacgaac | (SEQ ID No. 19) | 5625 | 5601 | 41 | | 158 |
| D2 09+ | GTTTTCCCAGTCACGACaagcccatttcacagaccc | (SEQ ID No. 20) | 5375 | 5393 | 36 | 920 | |
| D2 09− | AACAGCTATGACCATGtcaatttcttcctttccttc | (SEQ ID No. 21) | 6295 | 6274 | 38 | | 158 |
| D2 10+ | GTTTTCCCAGTCACGACgagaggagaagcaaggaaaac | (SEQ ID No. 22) | 6096 | 6116 | 38 | 923 | |
| D2 10− | AACAGCTATGACCATGagggacacattcactgagg | (SEQ ID No. 23) | 7019 | 7001 | 35 | | 233 |
| D2 11+ | GTTTTCCCAGTCACGACacagagaacaccccaagac | (SEQ ID No. 24) | 6750 | 6768 | 36 | 929 | |
| D2 11− | AACAGCTATGACCATGtccacttcctggattccac | (SEQ ID No. 25) | 7679 | 7661 | 35 | | 308 |
| D2 12+ | GTTTTCCCAGTCACGACacaagtaatgctcctagtcctc | (SEQ ID No. 26) | 7332 | 7353 | 39 | 935 | |
| D2 12− | AACAGCTATGACCATGttcactgatgacactatgttcc | (SEQ ID No. 27) | 8267 | 8246 | 38 | | 211 |
| D2 13+ | GTTTTCCCAGTCACGACgtcatcaccaaatcccacag | (SEQ ID No. 28) | 8016 | 8035 | 37 | 937 | |
| D2 13− | AACAGCTATGACCATGgcttcttctctcttttcccatc | (SEQ ID No. 29) | 8953 | 8931 | 39 | | 140 |
| D2 14+ | GTTTTCCCAGTCACGACaaggtgagaagcaatgcag | (SEQ ID No. 30) | 8773 | 8791 | 36 | 937 | |
| D2 14− | AACAGCTATGACCATGtggaaatggtgtgaacagaag | (SEQ ID No. 31) | 9710 | 9690 | 37 | | 209 |
| D2 15+ | GTTTTCCCAGTCACGACgcattcagcacctaacaatcac | (SEQ ID No. 32) | 9641 | 9482 | 39 | 9335 | |
| D2 15− | AACAGCTATGACCATGggcatttatgatggcctgac | (SEQ ID No. 33) | 10396 | 10377 | 36 | | — |

TABLE 6-continued list of RT-PCT and sequencing primers

| Name | Primers sequences | | NtStart | NtEnd | Primer length | RT-PCR length | Overlap |
|---|---|---|---|---|---|---|---|
| D2 16i+ | ccatggaagctgtacgc | (SEQ ID No. 34) | 10480 | 10496 | 64 | 234 | |
| D2 16i- | AACAGCTATGACCATGtgattcaacagcaccattcc | (SEQ ID No. 35) | 10714 | 10695 | 36 | | -28 |

2.2 Methods
2.2.1 Viral RNA Purification

From previous experience, a minimal of 1000 DICC.sub.50 is required to get a positive RT-PCR reaction in the next steps. This means that a minimum virus titer of $10^4$ $DICC_{50}$/mL is necessary. Virus genomic RNA was purified using QIAamp viral RNA mini kit (Qiagen), according to the manufacturer's recommendations. Briefly, a volume of 140 µl from a crude viral sample was incubated in the presence of the lysis solution, and loaded onto a kit column. After washing steps, the purified viral RNA was eluted by 60 µl of sterile nuclease-free water containing 1 µl (40 units) of RNAse inhibitor (RNAse Out, Sigma).

2.2.2 Reverse Transcription

Viral RNA was reverse transcribed into cDNA by a reverse transcriptase (reverse iT) from ABGene. Again, standard operating conditions were applied, using 10 µl of purified RNA, in a final reaction volume of 20 µl. The reaction was initiated by hybridization of the minus strand primers. One RT reaction per PCR was performed. The cDNA synthesis was obtained by 45 min incubation at 47° C.

2.2.3 PCR

All PCR were performed with Expand High Fidelity PCR system (Roche diagnostics), using all 16 pairs of primers (+) and (−) from Table 6. PCR conditions were the following ones:

| RT | 2 µl |
|---|---|
| 10x buffer | 2.5 µl |
| dNTP (10 mM) | mix 2 µl |
| Primers | 0.8 µl each |
| H20 | 16.4 µl |
| Enzyme | 0/5 µl |

| PCR program | | | |
|---|---|---|---|
| Denaturation | 94° C. | 2 min | |
| Denaturation | 94° C. | 15 sec | |
| Hybridization | 55° C. | 30 sec | 40 cycles |
| Elongation | 68° C. | 1 min | |
| Elongation | 68° C. | 5 min | |

All PCR products were controlled by electrophoresis on agarose gel.

2.2.4 Sequencing

The major part of the sequence reactions has been outsourced to Genome Express. Genome extremities, ambiguities, some inter-PCR junctions, and regions not sequenced by Genome Express for technical reasons were performed in-house.

Sequencing at Genome Express: PCR products were shipped at +4° C., and sequencing results were received as informatic sequence files. Text file, quality files and chromatograms are available for each individual sequence. After sequence alignment, all discrepancies were checked on the chromatogram, and corrected if identified as sequence algorithm errors.

In-house sequencing: Sequence reactions were performed on thermocycler PTC-200 (MJ Research), with Sequitherm Excell II LC kit (Epicentre). Each PCR product was sequenced on both strands independently in a single reaction. Reactions were loaded onto a sequence electrophoresis gel. Run and analysis of sequence were performed on the automated sequencer Gene Readl R 4200 (Li-Cor).

Sequence Reaction

| DNA | up to 200/250 ng |
|---|---|
| Reaction buffer | 72 µl |
| Primers (1-2 pM) | 1.5 µl each |
| Enzyme | 1 µl |
| $H_2O$ | up to 20 µl |

| PCR program | | | |
|---|---|---|---|
| Denaturation | 92° C. | 2 min | |
| Denaturation | 92° C. | 15 sec | |
| Hybridization | 50° C. | 30 sec | 30 cycles |
| Elongation | 70° C. | 1 min | |
| Elongation | 70° C. | 10 sec | |

Addition of 3 µl of denaturating/loading buffer.
Denaturation of samples 3 min at 95° C. and ice coding just before samples loading.

Sequence Electrophoresis

| Electrophoresis parameters | | Gel parameters | |
|---|---|---|---|
| Voltage | 1500 V | Gel hight | 41 cm |
| Current | 35 mA | Gel thickness | 0.2 mm |
| Power | 40 W | Temperature | 45° C. |
| Run time | 9H00 | Scan speed | 3 |

2.3 Results

All PCR fragments were sequenced from both ends using a common PCR added ail, i.e. a specific motif which has been added at 5' end of all primers:

```
                                            (SEQ ID No. 36)
5' primers: M13SEQ-GTTTTCCCAGTCACGAC (SEQ ID No. 37)
3' primers: M13REV-AACAGCTATGACCATG
```

M13-SEQ and -REV sequences correspond to universal M13 primers motifs (New England Biolabs references).

For final contig assembly, a quick analysis was performed in Vector NTi, in ContigExpress module (Informax). The LAV2 reference sequence was compared with all individual sequencing results. In such conditions, all results could be aligned at the right place on the complete genome, even when some regions were still missing contig assembly, giving a quick visualization of the overall genome alignment.

2.3.1 Complete VDV2 Sequence Assembly

The final sequence alignment was performed in Vector NTi, AlignX module (Informax). The classical multiple sequence alignment algorithm ClustalW (Thompson et al., 1994) was used by the software to build the global alignment. All the sequence results were aligned together with the LAV2 reference sequence, thus allowing for a better reconstruction of the genome. Any discrepancy in the sequence with regard to the reference required a confirmation on another independent sequence reaction. The complete sequence of VDV2 is shown in SEQ ID No.1.

Some ambiguities are often found in single sequences, especially near sequence extremities. This is inherent to the somewhat poor quality of the reaction at both ends of any PCR fragment. Such poor quality sequences were excluded from the alignment, until two other independent sequence reactions were available from other PCR products. Discrepancy towards the reference was not taken into account in the final alignment when not confirmed in at least two independent other PCR sequences matching the consensus. Conversely, any discrepancy confirmed on two independent sequences was kept in the final sequence.

Table 7 summarizes the characteristics of each individual sequence reaction, indicating start, end and length. Overlaps between adjacent PCR are also indicated, as well as differences with regard to the reference sequence in the last column.

sequence result is that of the synthetic oligonucleotide, and not that of the virus itself. PCR from both ends of the virus genome did work properly, suggesting that the viral sequence was not significantly different from the oligonucleotide sequence (if it had been the case, PCR amplification should have failed or at least should have been of poor quality). We were not able to distinguish them from all other PCR amplifications. So, in the reconstructed genome, both genome ends were considered as identical to oligonucleotide sequences (and also identical to the reference). At 5' end, the sequence is that of nucleotides 1 to 32. At 3' end, the sequence is that of nucleotides 10695 to 10723.

2.3.2 Sequence Comparison

Ten nucleotide differences have been detected with regard to the parent LAV2 genomic sequence. VDV2 vaccine strain is derived from LAV2, through virus sanitization and passage from dog to monkey cells.

Differences between LAV2 and VDV2 can have several origins. First, cloning steps can select a viral subpopulation that is not 100% identical to the major sequence previously detected in LAV2. Second, LAV2 has been produced on PDK cells, whereas VDV2 has been made on Vero cells. Such passage from dog to monkey cells is known to potentially induce virus changes that reflect adaptation to the new cell line. Third, as for all RNA viruses, the lower viral RNA polymerase fidelity triggers a higher genomic mutation rate than DNA polymerases do.

TABLE 7

Dengue VDV2 individual sequences characteristics

| Name | Start | End | Size | Overlap | Comments |
|---|---|---|---|---|---|
| D2 01+ | 33 | 365 | 332 | 0 | 2 sequences |
| D2 01− | 619 | 79 | 540 | 5 | 2 sequences |
| D2 02+ | 614 | 1334 | 720 | | 736 G > C (M9-G > R) |
| D2 02− | 1488 | 654 | 834 | 127 | 736 G > C (M9-G > R) |
| D2 03+ | 1361 | 2135 | 774 | | 1619 G > A (E228 G > E); 1638 A > G (E234K s) |
| D2 03− | 2227 | 1416 | 811 | 179 | 1619 G > A (E228 G > E); 1638 A > G (E234K s) |
| D2 04+ | 2048 | 2774 | 726 | | 2520 G > A (NS1-33K s) |
| D2 04− | 2866 | 2210 | 656 | 133 | 2520 G > A (NS1-33K s) |
| D2 05+ | 2733 | 3495 | 762 | | |
| D2 05− | 3619 | 2819 | 800 | 251 | |
| D2 06+ | 3393 | 4196 | 803 | | |
| D2 06− | 4257 | 3368 | 889 | 78 | |
| D2 07+ | 4179 | 4830 | 651 | | 4723 T > A (NS3-69 S > T) |
| D2 07− | 4851 | 4223 | 628 | 130 | 4723 T > A (NS3-69 S > T) |
| D2 08+ | 4742 | 5506 | 764 | | 5062 G > C (NS3-181 DD > H) |
| D2 08− | 5582 | 4721 | 861 | 188 | 5062 G > C (NS3-181 DD > H) |
| D2 09+ | 5394 | 6100 | 706 | | |
| D2 09− | 6669 | 5979 | 690 | 545 | |
| D2 10+ | 6124 | 6996 | 872 | | |
| D2 10− | 6983 | 6148 | 835 | 218 | |
| D2 11+ | 6778 | 7567 | 789 | | |
| D2 11− | 7649 | 6781 | 868 | 317 | |
| D2 12+ | 7365 | 8236 | 971 | | |
| D2 12− | 8241 | 7332 | 909 | 191 | |
| D2 13+ | 8050 | 8797 | 747 | | |
| D2 13− | 8819 | 8147 | 672 | 22 | |
| D2 14+ | 8707 | 9700 | 903 | | 9191 G > A (NS5-541 R > K); 9222 A > G (NS5-551E s) |
| D2 14− | 9654 | 8804 | 850 | 199 | 9191 G > A (NS5-541 R > K); 9222 A > G (NS5-551E s) |
| D2 15+ | 9501 | 10285 | 784 | | 10063 T > A (NS5-832 S > T) |
| D2 15− | 10347 | 9702 | 645 | 187 | 10063 T > A (NS5-832 S > T) |
| D2 16i+ | 10486 | 10687 | 201 | | 10507 A > G |
| D2 16i− | 10694 | 10160 | 534 | 0 | 10507 A > G |

The two extremities of the genome could not be sequenced from PCR amplification, because cDNA synthesis and PCR DNA reaction required oligonucleotides complementary to the ends of the genome. During the amplification step, these oligonucleotides are incorporated into the PCR fragment. The In term of sequences, all 9 nucleotide positions which have been linked to viral attenuation of LAV2 are conserved in VDV2 passage 11.

Furthermore, sequence comparison between VDV2 passage 9 and passage 11 showed the occurrence of two mutations between passages 9 and 11 which are linked to differences in phenotype, viremia and immunogenicity.

TABLE 8

Sequence comparison between LAV2/PDK53 strain and VDV2 passages 9 and 11 strains

| | Nucleotides | | | | Amino acids | | | |
|---|---|---|---|---|---|---|---|---|
| | | VDV2 | | | | | VDV2 | |
| Position | LAV2 | Passage 9 | Passage 11 | Region | Position | LAV2 | Passage 9 | Passage 11 |
| 736 | G | G | C | M | 9 | G | G | R |
| 1619 | G | A | A | E | 228 | G | E | E |
| 1638 | A | G | G | E | 234 | K | K | K |
| 2520 | G | A | A | NS1 | 33 | K | K | K |
| 4723 | T | A | A | NS3 | 69 | S | T | T |
| 5062 | G | C | C | NS3 | 181 | D | H | H |
| 5270 | A/T | A | A | NS3 | 250 | E/V | V | V |
| 9191 | G | G | A | NS5 | 541 | R | R | K |
| 9222 | A | G | G | NS5 | 551 | E | E | E |
| 10063 | T | A | A | NS5 | 832 | S | T | T |
| 10507 | A | G | G | 3'nc | — | — | — | — |

Bold: sequence differences between VDV2 passage 9 and passage 11/

When performing sequence alignment between all available Genbank serotype 2 Dengue genomic sequences, it appears that only two positions are shared by other Dengue 2 strains (1638 and 2520), both silent at amino acid level. All other positions are specific to the VDV2 passage 11 strain, triggering an amino acid substitution (Table 8). Concerning amino acid changes, the four changes in non-structural peptides appear relatively conservative, from a biochemical point of view, whereas the two changes in M and in the envelope bring modification both in charge and hydrophobicity.

Example 3

Characterization

The objective of these studies was to assess whether changes in attenuation markers occurred through passages.

The flow chart shown on FIG. 2 summarises the developed manufacturing process that gives rise to the Filled Product (monovalent), "ready to use" doses Briefly, after 2 successive passages on Vero cells of the VDV2 passage 8, the respective working seeds were obtained. The final virus cultivations are also conducted by infection of a Vero cell suspension. The viruses produced are then harvested. DesoxyRiboNucleic Acid (DNA) is digested according to an enzymatic treatment. Impurities are removed by ultrafiltration. Infectious titers are enhanced by a concentration step. An aqueous buffered solution comprising cryoprotective agents (pH=7.5) is added and this 0.22-μm filtrated mixture is then diluted at the targeted dose within the same solution. The active substance is then filled into glass vials, freeze-dried, and stored before use.

3.1 Phenotypic Markers

Table 9 presents data from three phenotypic assays performed on DEN-2 16681 wt strain, DEN-2 16681/PDK53 vaccine strain, VDV2 passage 9 and VDV2 passage 11 (last adaptation passage): temperature-sensitivity (Ts), growth curves on monkey (Vero) and mosquito (C6/36) cells and neurovirulence in Newborn mice (data obtained at CDC). Reduced mouse neurovirulence (reduced mortality and longer average survival time (AST)), restricted-growth at 39° C. and restricted replication on C6/36 are currently accepted by the scientific community as attenuation criteria for Dengue viruses. Vero-adapted passages exhibit clear Ts profile, and are more restricted than DEN2/PDK53. Final adaptation passage is restricted by about 3 log in this assay. Temperature sensitivity was also confirmed by viral growth curves. On Vero cells, similar replication levels were observed with all tested viruses. On mosquito cells, viral growth of Vero-adapted viruses was clearly restricted (about 3 log) compared to wt DEN2, and slightly restricted (about 0.5 log) compared to DEN2-PDK53. Surprisingly, mouse neurovirulence of Vero-adapted viruses was close to neurovirulence of wt DEN2, and significantly higher than neurovirulence of DEN2/PDK53 vaccine. These data point out the low predictive value of this say, with regard to viral strain attenuation (cf clinical data).

Plaque size distribution of VDV2 passages 9 and 11, DEN2/PDK53 and wtDEN2 are compared to FIG. 5. Wt DEN2 exhibits heterogenous profile with 95% of plaques with a size homogeneous profile, with a major population (81%) of plaques<0.6 mm and a minor population (12%) of 1-2 mm plaques. This profile is close to, but distinct from DEN2-PDK53 profile. Noteworthy, the intermediate adaptation passage, VDV2 P9, exhibits a more heteregenous profile, with a major population (70%) of 1-2 mm plaques, and a minor population (25%) of plaques<0.6 mm. These data demonstrate that VDV2 strain was not yet fully adapted at passage 9, and that the two additional passages were required for obtention of a homogeneous population replicating stably in Vero cells.

TABLE 9

Summary of DEN-2 viral phenotypes

| | Temperature sensitivity (Percent titer reduction at 39° C.)$_{Fold\text{-}reduction}$ | | | | | Growth curves (Peak $log_{10}$ pfu/ml) Vero-LS10 | | Neurovirulence in newborn Swiss Webster mice | |
|---|---|---|---|---|---|---|---|---|---|
| Virus | Score | Day 3 | Day 4 | Day 5 | Day 6 | Titer | at Day | $Mortality_n$ | AST (S.D.) |
| D2-16681 | + | n.d. | $92.7_{13.7}$ | n.d. | $92.2_{12.8}$ | 7.5 | 8 | $100.0\%_{16}$ | 12.2 (1.5) |
| D2-PDK53 | + | n.d. | $96.6_{29.4}$ | n.d. | $99.7_{333.3}$ | 7.3 | 8-10 | $43.75\%_{16}$ | 16.0 (2.4) |
| VDV2 P9 | + | n.d. | $99.94_{1666.7}$ | n.d. | $99.97_{3333.3}$ | 7.5 | 8-10 | $100.0\%_{16}$ | 10.9 (0.7) |
| VDV2 P11 | + | n.d. | $99.92_{1250.0}$ | n.d. | $99.88_{833}$ | 7.5 | 10 | $100.0\%_{16}$ | 10.9 (0.6) |

N: number of animals.

Example 4

Immunogenicity, Viremia, and Toxicology in Monkeys

The most solid and numerous data that can be obtained in monkeys concern immunogenicity and viremia. Viremia, in particular, has been identified as one of the factors associated with virulence and disease severity in humans, and then constitute an important parameter to consider. Obviously, immunogenicity is a key parameter when testing vaccines.

Inventors have established minimal/maximal values for viremia and immunogenicity.

TABLE 10

Minimal requirements for responses induced by Dengue vaccine candidates in monkeys, as measured in Vero or LLC-MK2 cells by plaque assay (these cells being considered equivalent in such an assay)

| Viremia mean duration (days) (all serotypes being considered) | Viremia mean peak titer (log 10 pfu) (all serotypes being considered) | Mean neutralizing titer Day 30 (for each serotype) PRNT 50 |
|---|---|---|
| ≦3 days | ≦1.5-2 | ≧80 | pfu: plaque forming unit

PRNT 50: Plaque Reduction Neutralization Titer 50 (titre corresponding to a reduction of 50% of plaque number)

4.1 Pre-Clinical Pharmacology, Pharmacokinetics, and Product Metabolism in Animals 4.1.1 Material and Methods 4.1.1.1 Monkey Experiments Monkey experiments were carried out according to European guidelines regarding animal experiments.

Immunizations were performed on cynomolgus monkeys (*Macaca fascicularis*) originating from Mauritius (CRP Le Vallon). Monkeys were quarantined for 6 weeks in the animal facility of Sanofi Pasteur before immunization.

Monkeys were immunized by subcutaneous (SC) route in the arm with vaccines in a volume of 0.5 ml (see each respective section). After light anesthesia with ketamine (Imalgene, Merial), blood was collected by puncture of the inguinal or saphene veins. At days 0 and 28, 5 ml of blood were sampled for evaluating antibody responses while between days 2 and 10 only 1 ml of blood was sampled for evaluating viremia. Blood was collected on ice and kept on ice until serum separation. To do so, blood was centrifuged for 20 minutes at 4° C., and serum collected and stored at −80° C. until testing in Rich Kinney's laboratory. Shipment to USA was performed in dry ice.

4.1.1.2 Viremia and Neutralizing Antibody Responses (Plaque Reduction Neutralization Test, PRNT)

All analyses were performed in the laboratory of R. Kinney in CDC, Fort Collins, USA. Serum samples were shipped and stored at −80° C. until the time of testing. At the time of first thawing, the samples were tested for viremia, and a 1:5 dilution of the serum was made. The 1:5 serum dilutions were inactivated for 30 min at 56° C. before testing for neutralizing antibodies.

4.1.1.2.1 Viremia 0.125 ml of serum was added to 0.125 ml of diluent (RPMI medium) in the first well of 96-well plate and serial 10-fold dilution series were done, transferring 0.025 ml into 0.225 ml of diluent for each dilution. 0.2 ml of $10^{0.3}$-$10^{5.3}$ dilution series was plated in 6-well plate of Vero cells (virus was adsorbed at 37° C. for 1.5 hour, overlayed with 4 ml of agarose lacking neutral red, overlayed 6-7 days later with 2 ml of agarose containing neutral red, and plaques counted). The limit of virus detection was =10 PFU/ml. For controls stock DEN-16681 PDK-53 (LAV2) vaccine was plated.

4.1.1.2.2 PRNT (Plaque Reduction Neutralization Test)

Neutralizing antibodies were quantified as described in Huang et al. (2000). Briefly, 0.2 ml of heat-inactivated, 1:5 dilution of serum was added to the first well of 96-well plate and serial 2-fold dilution series were made, transferring 0.1 ml into 0.1 ml of diluent (RPMI medium) for each dilution. This resulted in a 1:10-1:320 serum dilution series. 0.1 ml of DEN virus (60-160 PFU; parental DEN2 16681 virus) was added to each serum dilution well for a total of 0.2 ml of serum-virus mixture. 96-well plates were incubated overnight at 4° C. 0.1 ml of serum-virus mixtures (containing 30-80 PFU of input virus) were plated in 6-well Vero plates (as indicated above in the Viremia section) and plaques were counted after staining with neutral red. Multiple back titrations of the input viruses at 2-fold, 1-fold, and 0.5-fold test concentrations provided direct experimental determination of the input PFU, which was the basis for determining 50% ($PRNT_{50}$) and 70% ($PRNT_{70}$) endpoint antibody titers. A negative serum result should have a neutralizing antibody titer of <1:10. Sera showing neutralization titers of 320 were retested at dilutions 1:80-1:2560 for determination of endpoint titer.

4.1.2 Evaluation of Monovalent VDV2 Candidate at Passage 9 in Monkeys

Purification/selection of VDV2 candidate has been conducted as described in example 1. The selected clones (based on phenotypic markers and sequence) have been tested after 9 passages in cell culture in Sanofi Pasteur on male cynomolgus macaques (*Macaca fascicularis*, mean weight 3.1 kg) originating from CRP Le Vallon, Mauritius.

After immunization on D0, viremia was followed from D2 to D10, and immunogenicity measured at D0 and D28. All viruses and vaccines, when in liquid form, were kept at −70° C.

LAV2: titre: $10^{3.93}$ DICC.sub.50/ml; lyophilized, resuspended in 0.5 ml of PBS (containing $Ca^{2+}$ and $Mg^{2+}$; $CaCl_2.2H_2O$ 0.133 g/l; $MgCl.\text{sub.}_2.6H_2O$, 0.1 g/l) and administered in totality.

Passage VDV2 DEN2-TV722 (2 plaque purifications+1 amplification): Titre: $10^{5.6}$ $DICC_{50}$/ml; liquid, diluted at $10^{5.3}$ pfu/ml in PBS (containing $Ca^{2+}$ and $Mg^{2+}$; $CaCl_2.2H_2O$ 0.133 g/l; $MgCl._2.6H_2O$, 0.1 g/l); 0.5 ml administered.

Injection was done by SC route in the arm with a 23G1 needle, at a $10^5$ $DICC_{50}$ dose for VDV2.

The results are as presented in Table 11. Titration at day 28 were carried out in triplicate for both $PRNT_{70}$ or and $PRNT_{50}$.

The comparison between VDV2 and LAV2 showed clear differences in viremia, with high viremia of short duration for VDV2 in ¾ monkeys compared to LAV2, and significant immunogenicity for both types (rather lower for VDV2). This viremia may be considered as too high for VDV2 at this pre-master level after only a few passages on Vero cells. However, wild type DEN-2 (and other types too) induce viremia of longer duration (6 to 7 days) and intensity (up to 5 logs plaque forming units [pfu]) (Monath et al., 2000; Bray et al., 1996).

Male *Macaca fascicularis* monkeys were used as before, originating from C.R.P. Le Vallon, Ile Maurice (24 monkeys, mean weight 3.4 kg).

Passage 11 VDV2: Batch: Titre: 8.07 log 10 g $DICC_{50}$/ml

Placebo: PBS with $Ca^{2+}$ and $Mg^{2+}$

VDV3: VERO-Derived Vaccine Dengue serotype 3 strain, obtained by sanitization of LAV3 on Vero cells.

VDV4: VERO-Derived Vaccine Dengue serotype 4 strain, obtained by sanitization of LAV4 on Vero cells.

Vaccines were diluted at $10^{5.3}$ $DICC_{50}$/ml in PBS (containing $Ca^{2+}$ and $Mg^{2+}$; $CaCl_2.2H_2O$ 0.133 g/l; $MgCl_2.6H_2O$, 0.1 g/l); 0.5 ml administered by SC route in the arm with a 23G1 needle, corresponding to a dose of $10.\text{sup.}^5$ $DICC_{50}$.

Viremia and immunogenicity have been measured as usual in CDC by R Kinney. The results are shown in Table 12.

VDV2 passage 11 monovalent vaccine induced a significant immune response, while viremia was low or absent. The absent/low VDV2-induced viremia is to be considered in light of the previous experiment in which the passage 9 VDV2 induced high early viremia. Some evolution between passages 9 and 11 suppressed this high viremia while immunogenicity was maintained. VDV2 therefore constitutes an acceptable candidate.

It is to be noted that in the same experiment, 4 monkeys were vaccinated with a tetravalent formulation involving the same VDV2 passage 11 vaccine; no viremia was detected for VDV1 and VDV2 while VDV3 and VDV4 induced viremia.

Two other experiments involved the administration of VDV2, alone or in combination with the other serotypes.

In the first one (tetravalent study; 5-log of each serotype), no viremia was detected for VDV2, and VDV1, while high levels of viremia were detected for VDV3 and VDV4.

In the second experiment, VDV2 passage 11 was administered alone or within a tetravalent combination including

TABLE 11

VDV2 passage 9 immunogenicity

| Serum | Group | Neutralizing Antibody Titer | | | | Viremia (PFU/ml in Vero cells) | | | | | | | | | |
|---|---|---|---|---|---|---|---|---|---|---|---|---|---|---|---|
| | | Day (−15) | | Day 28 | | Day −15 | Day 2 | Day 3 | Day 4 | Day 5 | Day 6 | Day 7 | Day 8 | Day 9 | Day 10 |
| | | $PRNT_{70}$ | $PRNT_{50}$ | $PRNT_{70}$ | $PRNT_{50}$ | | | | | | | | | | |
| AD 097 | LAV DEN-2 | <10 | <10 | 80/80/160 | 320/160/320 | 0 | 0 | 0 | 0 | 0 | 0 | 5 | 0 | 50 | 20 |
| AC 170 | | <10 | <10 | 160/80/320 | 320/160/640 | 0 | 0 | 0 | 0 | 0 | 5 | 5 | 0 | 0 | 0 |
| AD 677 | | <10 | <10 | 1280/640/2560 | 2560/1280/2560 | 0 | 5 | 0 | 0 | 10 | 50 | 0 | 5 | 0 | 0 |
| AC 182 | | <10 | <10 | 320/320/320 | 640/1280/1280 | 0 | 0 | 5 | 0 | 15 | 5 | 0 | 5 | 0 | 0 |
| AC 658 | VDV DEN-2 | <10 | <10 | 160/160/160 | 320/160/640 | 0 | 550 | 35 | 0 | 0 | 0 | 0 | 0 | 0 | 0 |
| AC 512 | | <10 | <10 | 160/80/160 | 160/160/160 | 0 | 1650 | 35 | 0 | 5 | 0 | 0 | 0 | 0 | 0 |
| AD 608 | | <10 | <10 | 160/320/160 | 320/320/320 | 0 | 1700 | 60 | 100 | 0 | 0 | 0 | 0 | 0 | 0 |
| AD 132 | | <10 | <10 | 80/80/80 | 80/160/160 | 0 | 70 | 10 | 0 | 50 | 10 | 100 | 0 | 0 | 0 |
| Virus DEN-2 | Exp#1 60PFU | Exp#2 54PFU | Exp#3 46PFU | | | | | | | | | | | | |

4.1.3 Evaluation of Monovalent VDV2 Candidate at Passage 11

As immunogenicity of the vaccines had been tested at the passage 9, a further experiment was designed to test the monovalent passage after two additional passages (passage 10).

VDV1. When administered alone, VDV2 passage 11 induced a low viremia (peak 40) in only 1 out of 4 monkeys while the 3 others were negative. When present within tetravalent formulations, VDV2 induced no or dramatically lower viremia than VDV3 and VDV4, even though VDV2 was administered at 4 log while VDV3 and VDV4 were administered at 2 log.

This demonstrates the higher safety of VDV2, as far as viremia is concerned. Monovalent VDV2 thus fulfilled the success criteria initially defined in monkeys.

In conclusion, the subcutaneous administration of VDV2 to the cynomolgus monkey (*Macaca fascicularis*) at the test doses did not adversely affect the health of the monkeys as assessed by in-life clinical observations and clinical pathology.

TABLE 12 passage 11 VDV2 immunogenicity and viremia

| Monkey | Group | Neutralizing Antibody Titer | | | | Viremia (PFU/ml in Vero cells) | | | | | | | | |
|---|---|---|---|---|---|---|---|---|---|---|---|---|---|---|
| | | Day (−14) | | Day 29 | | Day −14 | Day 3 | Day 4 | Day 5 | Day 6 | Day 7 | Day 8 | Day 9 | Day 10 |
| | | $PRNT_{50}$ | $PRNT_{70}$ | $PRNT_{50}$ | $PRNT_{50}$ | | | | | | | | | |
| AE 971 | VDV DEN-2 | — | — | 180 | 80 | 0 | 0 | 0 | 0 | 0 | 0 | 0 | 0 | 0 |
| AE 990 | | — | — | 160 | 50 | 0 | 15 | 0 | 0 | 5 | 0 | 0 | 0 | 0 |
| AE 998 | | — | — | 905 | 508 | 0 | 0 | 0 | 0 | 0 | 0 | 0 | 0 | 0 |
| AF 182 | | — | — | 285 | 101 | 0 | 0 | 0 | 0 | 0 | 0 | 0 | 0 | 0 |
| Geo Mean | homologous | — | — | 293 | 119 | | | | | | | | | |
| AE 538 | Placebo | —/—/—/— | —/—/—/— | 2.5/—/2/2 | —/—/—/— | 0 | 0 | 0 | 0 | 0 | 0 | 0 | 0 | 0 |
| AE 548 | | —/—/—/— | —/—/—/— | —/—/1/2 | —/—/—/— | 0 | 0 | 0 | 0 | 0 | 0 | 0 | 0 | 0 |
| AE 556 | | —/—/1.5/2 | —/—/—/— | 1/—/—/— | —/—/—/— | 0 | 0 | 0 | 0 | 0 | 0 | 0 | 0 | 0 |
| AE 572 | | —/—/1.5/5 | —/—/1.5/2 | 5/—/—/2 | —/—/—/— | 0 | 0 | 0 | 0 | 0 | 0 | 0 | 0 | 0 |
| Geo Mean | | —/—/1.2/3 | —/—/1/1 | 2/—/ 1.2/1.6 | —/—/—/— | | | | | | | | | |
| | | D1/D2/D3/D4 | D1/D2/D3/D4 | D1/D2/D3/D4 | D1/D2/D3/D4 | | | | | | | | | |

4.2 Toxicology of VDV2

4.2.1 Neurovirulence Tests in Monkeys

The objective of this test was to demonstrate the lack of neurotropic properties in monkeys (Ph. Eur. 2.6.18) of the attenuated 2 dengue virus seed produced by Sanofi Pasteur.

10 cynomolgus monkeys from Mauritius were inoculated with VDV2 passage 9 by the intracerebral route ($10^{7.10}$ $CCID_{50}$/in the thalamus of each hemisphere). At the end of the test, the monkeys were sacrificed and perfused with formaline solution. Tissue samples were taken from the brain of each monkey (medulla oblongata, pons and cerebellum, midbrain, thalamus including the left and the right parts, the left and the right of the cerebral cortex). Sections were cut at a thickness of 8 .mu.m and stained by eosin and gallocyanin.

No histopathological signs of pathogenicity were observed in the monkey brains injected with serotype 2 primary virus seed.

4.2.2 GLP Toxicity Study in the Cynomolqus Monkey after 1 Subcutaneous Administration of VDV2 Followed by a 28-Day Observation Period The objective of this GLP study was to assess the interactions between VDV2 passage 9 and other Dengue vaccine candidates. The 1st step of the study was to assess the safety and immunogenicity of VDV2 prior to the administration of another vaccine candidate.

One human dose of VDV2 (approximately $10^4$ $CCID_{50}$ per dose) was administered subcutaneously on Day 0 to cynomolgus monkeys (4 males and 4 females). A control group of 2 males and 2 females received the vehicle (4% NaCl).

Mortality, clinical condition, body weight, and food consumption were monitored throughout the study. Body temperature was taken once pre-test, daily from the day of each administration and during 2 days after. Blood samples were taken for clinical laboratory determinations once pre-test and on Days 8 and 27.

There were no effects on clinical signs, body weight, food consumption, dermal reactions, body temperature, haematology, clinical chemistry, or organ weights. No deaths were reported during the study.

Example 5

Safety of Monovalent VDV2 in Healthy, Lavivirus-Naive Adults Aged 18 to 40 Years The aim of this phase 1 trial is to document the safety, viremia, and immunogenicity profiles of monovalent VDV2 passage 1 1 at a virus concentration of 1 04 $CCID_{50}$ compared to Stamaril® (used as control group) in flavivirus-naive adults. Single injections are given, with follow-up at 6 and 12 months. For safety precaution, sequential inclusions are performed in the study.

Enrollment and vaccinations are therefore staggered; a 1st cohort (n=4 per group, total n=12) have been vaccinated. The safety data collected up to Day 28 have been reviewed by an Independent Data Monitoring Committee (IDMC) and by the Royal Adelaide Hospital Investigational Drugs Subcommittee (IDSC) before deciding to proceed with the vaccination of the remaining subjects (n=8 per group, total n=16). A schematic representation of the trial design is provided in FIG. 6.

After administration of the vaccine the patient are regularly submitted to various clinical examination and testing. A summary of this follow up is given in Table 13 below.

The enrolled population consists of adults aged 18 to 40 years (i.e. the day of the 18th birthday to the day before the 41st birthday) on day of inclusion who are flaviviruses-naive [persons presenting vaccination against flavivirus diseases (e.g. yellow fever, Japanese encephalitis, dengue fever); or history of flavivirus infection (confirmed either clinically, serologically or microbiologically) or previous residence in or travel to areas with high dengue infection endemicity (whatever the duration), or residence in or travel to North Queensland for 2 weeks or more) were excluded]

TABLE 13

Flow chart for follow up

| | Visit Number | | | | | | | | | | | |
|---|---|---|---|---|---|---|---|---|---|---|---|---|
| | V01 | V02 | V03 | V04 | V05 | V06 | V07 | V08 | V09 | V10 | V11 | V12 |
| | Trial timelines¤ | | | | | | | | | | | |
| Time Windows | D0 | D2 | D4 | D6 | D8 | D10 ±1 d | D12 ±1 d | D14 | D16 | D28 ±4 d | D180 ±15 d | D365 ±30 d |
| Clinical Examination | ✓ | ✓ | ✓ | ✓ | ✓ | ✓ | ✓ | ✓ | ✓ | ✓ | ✓ | ✓ |
| Vital signs (BP, pulse rate) | ✓ | | | | | | | | | | | |
| Oral temperature | ✓ | ✓ | ✓ | ✓ | ✓ | ✓ | ✓ | ✓ | ✓ | ✓ | | |
| Blood Sampling: | | | | | | | | | | | | |
| Serology HBV/HCV/HIV | ✓ | | ✓ | | ✓ | | ✓ | | ✓ | ✓ | | |
| Biological Safety | ✓ | ✓ | ✓ | ✓ | ✓ | ✓ | ✓ | ✓ | ✓ | | | |
| Viremia | ✓ | | | | | | | | ✓ | ✓ | ✓ | ✓ |
| Immunogenicity | ✓ | ✓ | ✓ | ✓ | ✓ | ✓ | ✓ | ✓ | ✓ | ✓ | | |
| Cytokines in serum | ✓ | | | | | | | | | ✓ | | |
| PBMCs for T cell (subset) | ✓ | | | | | | | | | ✓ | | |
| immediate surveillance | ✓ | | | | | | | | | | | |
| Local & systemic events | ✓ | ✓ | ✓ | ✓ | ✓ | ✓ | ✓ | ✓ | ✓ | ✓ | ✓ | ✓ |

V: visit
D: day.

¤ Time intervals between visits will be calculated from the date of study vaccination which might differ from the date of visit (e.g. in case a temporary exclusion criterion is met). V06 and V07 must be done with at least 1-day interval.

The products tested are:

The vaccine evaluated is a lyophilised product in a vial that is reconstituted extemporaneously with the diluent provided separately:

Active ingredient: 4±0.5 $\log_{10}$ $CCID_{50}$ of monovalent Vero dengue virus serotype 2 (VDV2 passage 11) per 0.5 mL dose;

Diluent: Sterile NaCl .sup.4‰ solution for vaccine reconstitution.

The reconstituted vaccine, i.e 0.5 mL of NaCl 4‰ solution of monovalent VDV2, should be used immediately or be maintained until use +2° C. and +8° C.

The 0.5 mL vaccine dose is administered subcutaneously in the deltoid region.

The control vaccine Stamaril®, is a yellow fever vaccine produced by Aventis Pasteur. Stamaril® is presented as a lyophilised, avian-leukosis-free, stabilised product to be reconstituted with a diluent immediately before use. (Active ingredient: Live attenuated yellow fever virus (17D strain): . gtoreq.1,000 mouse Lethal Dose 50% ($LD_{50}$)/Diluent: Sterile NaCl 4‰ solution).

The control vaccine is administered subcutaneously in the deltoid region.

No subject had clinically significant syndrome related to vaccination. One subject had a transient fever (<38° C.). One subject had a local reaction (induration). No serious adverse event related to vaccination was observed.

All subjects have antibodies response 28 days after vaccination against dengue 2 (titer between 1888 and 6393)

REFERENCES

Bhamarapravati, N and Yoksan S. (1997). Dengue and Dengue Hemorrhagic Fever. Live attenuated tetravalent dengue vaccines, CABI Publishing, 367-379.

Burke D S and Monath T P. Flaviviruses (2001) In Knipe D M and Howley P M, eds. Fields Virology 4th ed. Vol 1, 1043-1125

DeFraites R F, Smoak B L, Trofa A F, Hoke C H, Kanesathasan N, King A, MacArthy P O, et al. Dengue fever among U.S. military personnel—Haiti, September-November, 1994. MMWR 1994; 43: 845-848.

Dunnen and Antonarakis (2000) Mutation nomenclature extensions and suggestions to describe complex mutations: a discussion. Hum Mutation. 15:7-12; Erratum in: Hum Mutat 2002; 20(5):403

Gubler D J. Dengue. (1988) In: Epidemiology of arthropod-borne viral disease. Monath T P M, editor, Boca Raton (Fla.): CRC Press:223-60

Gubler D J, Kuno G. Dengue and Dengue Hemorrhagic Fever. CAB International Publishing 1997

Gubler D. Epidemic dengue/dengue hemorrhagic fever as a public health, social and economic problem in the 21st century. (2002) TRENDS in Microbiology. 10:100-103

Halstead S B and Simasthien P (1970). Observations related to pathogenesis of Dengue haemorrhagic fever. II. Antigenic and biological properties of dengue viruses and their association with disease response in the host. Yale J. Biol. Med; 42: 261-275.

Huang et al. (2000). J. Virol 74; 3020-3028.

Jirakanjanakit N, Khin M M, Yoksan S, Bhamarapravati N. (1999) Dynamics of susceptibility and transmissibility of the live, attenuated, candidate vaccines dengue-1 PDK13, dengue-3 PGMK30F3, and dengue-4 PDK48 after oral infection in *Aedes aegypti*. Am J Trop Med. Hyg., 61(4): 672-676

Kautner I, Robinson M J, Kubnle U. (1997) Dengue Virus infection: Epidemiology, pathogenesis, clinical presentation, diagnosis, and prevention. J of Pediatrics; 131:516-524

Monath, T P. (1994) Dengue: the risk to developed and developing countries. Proc Natl Acad Sci; 91: 2395-2400.

Monath T P, Levenbook I, Soike K, Zhang Z X, Ratterree M, Draper K et al. (2000) Chimeric yellow fever virus 17D-Japanese encephalitis virus vaccine: dose-response effectiveness and extended safety testing in rhesus monkeys. Journal of Virology; 74(4):1742-1751

Bray M, Men R, Lai C J. (1996) Monkeys immunized with intertypic chimeric dengue viruses are protected against wild-type virus challenge. J Virol; 70(6):4162-4166

Rigau-Perez J G, Clark G G, Gubler D J, Reiter P, Sanders E J, Vorndam A V. (1998) Dengue and dengue haemorrhagic fever. Lancet; 352: 971-977.

Rothman A L, Ennis F A. (1999) Immunopathogenesis of dengue hemorrhagic fever. Virology; 257: 1-6

Sabin A B. (1952) Research on dengue during World War II. Am J Trop Med Hyg; 1: 30-50

Shirtcliffe P, Cameron E, Nicholson K G, Wiselka M J. (1998) Don't forget dengue! Clinical features of dengue fever in returning travelers. J Roy Coll Phys Lond.; 32: 235-237.

Thompson J D, Higgins D G, and Gibson T J. (1994) CLUSTAL W: improving the sensitivity of progressive multiple sequence alignment through sequence weighting, position-specific gap penalties and weight matrix choice. Nucl. Acids. Res., 22 (22), 4673-4680

Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30.

Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9.

WHO Technical Guide, 1986. Dengue haemorrhagic fever: diagnosis, treatment and control, p 1-2. World Health Organization, Geneva, Switzerland Wu S, Grouard-Vogel G, Sun W, Mascola J, Brachtel E, Putvatana R. (2000) Human skin Langerhans cells are targets of dengue virus infection. Nature Med; 7:816-820

Khin M M, Jirakanjanakit N, Yoksan S, Bhamarapravati N. (1994) Infection, dissemination, transmission, and biological attributes of dengue-2 PDK53 candidate vaccine virus after oral infection in *Aedes aegypti*. Am J Trop Med Hyg., 51(6):864-869

```
                              SEQUENCE LISTING

<160> NUMBER OF SEQ ID NOS: 42

<210> SEQ ID NO 1
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: VDV2
<220> FEATURE:
<221> NAME/KEY: CDS
<222> LOCATION: (97)..(10272)
<220> FEATURE:
<221> NAME/KEY: misc_feature
<222> LOCATION: (10361)..(10361)
<223> OTHER INFORMATION: unknown

<400> SEQUENCE: 1
agttgttagt ctacgtggac cgacaaagac agattctttg agggagctaa gctcaatgta      60
gttctaacag ttttttaatt agagagcaga tctctg atg aat aac caa cgg aaa      114
                                        Met Asn Asn Gln Arg Lys
                                        1               5 aag gcg aaa aac acg cct ttc aat atg ctg aaa cgc gag aga aac cgc      162
Lys Ala Lys Asn Thr Pro Phe Asn Met Leu Lys Arg Glu Arg Asn Arg
            10                  15                  20 gtg tcg act gtg caa cag ctg aca aag aga ttc tca ctt gga atg ctg      210
Val Ser Thr Val Gln Gln Leu Thr Lys Arg Phe Ser Leu Gly Met Leu
        25                  30                  35 cag gga cga gga cca tta aaa ctg ttc atg gcc ctg gtg gcg ttc ctt      258
Gln Gly Arg Gly Pro Leu Lys Leu Phe Met Ala Leu Val Ala Phe Leu
    40                  45                  50 cgt ttc cta aca atc cca cca aca gca ggg ata ttg aag aga tgg gga      306
Arg Phe Leu Thr Ile Pro Pro Thr Ala Gly Ile Leu Lys Arg Trp Gly
55                  60                  65                  70 aca att aaa aaa tca aaa gct att aat gtt ttg aga ggg ttc agg aaa      354
Thr Ile Lys Lys Ser Lys Ala Ile Asn Val Leu Arg Gly Phe Arg Lys
                75                  80                  85 gag att gga agg atg ctg aac atc ttg aat agg aga cgc aga tct gca      402
Glu Ile Gly Arg Met Leu Asn Ile Leu Asn Arg Arg Arg Arg Ser Ala
            90                  95                  100 ggc atg atc att atg ctg att cca aca gtg atg gcg ttc cat tta acc      450
Gly Met Ile Ile Met Leu Ile Pro Thr Val Met Ala Phe His Leu Thr
        105                 110                 115
```

| | | |
|---|---|---|
| aca cgt aac gga gaa cca cac atg atc gtc agc aga caa gag aaa ggg<br>Thr Arg Asn Gly Glu Pro His Met Ile Val Ser Arg Gln Glu Lys Gly<br>120                       125                   130 | | 498 |
| aaa agt ctt ctg ttt aaa aca gag gtt ggc gtg aac atg tgt acc ctc<br>Lys Ser Leu Leu Phe Lys Thr Glu Val Gly Val Asn Met Cys Thr Leu<br>135                   140                  145                  150 | | 546 |
| atg gcc atg gac ctt ggt gaa ttg tgt gaa gac aca atc acg tac aag<br>Met Ala Met Asp Leu Gly Glu Leu Cys Glu Asp Thr Ile Thr Tyr Lys<br>                   155                  160                  165 | | 594 |
| tgt ccc ctt ctc agg cag aat gag cca gaa gac ata gac tgt tgg tgc<br>Cys Pro Leu Leu Arg Gln Asn Glu Pro Glu Asp Ile Asp Cys Trp Cys<br>                 170                  175                  180 | | 642 |
| aac tct acg tcc acg tgg gta act tat ggg acg tgt acc acc atg gga<br>Asn Ser Thr Ser Thr Trp Val Thr Tyr Gly Thr Cys Thr Thr Met Gly<br>                   185                  190                  195 | | 690 |
| gaa cat aga aga gaa aaa aga tca gtg gca ctc gtt cca cat gtg cga<br>Glu His Arg Arg Glu Lys Arg Ser Val Ala Leu Val Pro His Val Arg<br>200                       205                  210 | | 738 |
| atg gga ctg gag aca cga act gaa aca tgg atg tca tca gaa ggg gcc<br>Met Gly Leu Glu Thr Arg Thr Glu Thr Trp Met Ser Ser Glu Gly Ala<br>215                       220                  225                  230 | | 786 |
| tgg aaa cat gtc cag aga att gaa act tgg atc ttg aga cat cca ggc<br>Trp Lys His Val Gln Arg Ile Glu Thr Trp Ile Leu Arg His Pro Gly<br>                   235                  240                  245 | | 834 |
| ttc acc atg atg gca gca atc ctg gca tac acc ata gga acg aca cat<br>Phe Thr Met Met Ala Ala Ile Leu Ala Tyr Thr Ile Gly Thr Thr His<br>                   250                  255                  260 | | 882 |
| ttc caa aga gcc ctg att ttc atc tta ctg aca gct gtc act cct tca<br>Phe Gln Arg Ala Leu Ile Phe Ile Leu Leu Thr Ala Val Thr Pro Ser<br>                   265                  270                  275 | | 930 |
| atg aca atg cgt tgc ata gga atg tca aat aga gac ttt gtg gaa ggg<br>Met Thr Met Arg Cys Ile Gly Met Ser Asn Arg Asp Phe Val Glu Gly<br>280                       285                  290 | | 978 |
| gtt tca gga gga agc tgg gtt gac ata gtc tta gaa cat gga agc tgt<br>Val Ser Gly Gly Ser Trp Val Asp Ile Val Leu Glu His Gly Ser Cys<br>295                       300                  305                  310 | | 1026 |
| gtg acg acg atg gca aaa aac aaa cca aca ttg gat ttt gaa ctg ata<br>Val Thr Thr Met Ala Lys Asn Lys Pro Thr Leu Asp Phe Glu Leu Ile<br>                   315                  320                  325 | | 1074 |
| aaa aca gaa gcc aaa cag cct gcc acc cta agg aag tac tgt ata gag<br>Lys Thr Glu Ala Lys Gln Pro Ala Thr Leu Arg Lys Tyr Cys Ile Glu<br>                   330                  335                  340 | | 1122 |
| gca aag cta acc aac aca aca gaa tct cgc tgc cca aca caa ggg<br>Ala Lys Leu Thr Asn Thr Thr Glu Ser Arg Cys Pro Thr Gln Gly<br>                   345                  350                  355 | | 1170 |
| gaa ccc agc cta aat gaa gag cag gac aaa agg ttc gtc tgc aaa cac<br>Glu Pro Ser Leu Asn Glu Glu Gln Asp Lys Arg Phe Val Cys Lys His<br>360                       365                  370 | | 1218 |
| tcc atg gta gac aga gga tgg gga aat gga tgt gga cta ttt gga aag<br>Ser Met Val Asp Arg Gly Trp Gly Asn Gly Cys Gly Leu Phe Gly Lys<br>375                       380                  385                  390 | | 1266 |
| gga ggc att gtg acc tgt gct atg ttc aga tgc aaa aag aac atg gaa<br>Gly Gly Ile Val Thr Cys Ala Met Phe Arg Cys Lys Lys Asn Met Glu<br>                   395                  400                  405 | | 1314 |
| gga aaa gtt gtg caa cca gaa aac ttg gaa tac acc att gtg ata aca<br>Gly Lys Val Val Gln Pro Glu Asn Leu Glu Tyr Thr Ile Val Ile Thr<br>                   410                  415                  420 | | 1362 |
| cct cac tca ggg gaa gag cat gca gtc gga aat gac aca gga aaa cat<br>Pro His Ser Gly Glu Glu His Ala Val Gly Asn Asp Thr Gly Lys His<br>425                       430                  435 | | 1410 |

```
ggc aag gaa atc aaa ata aca cca cag agt tcc atc aca gaa gca gaa      1458
Gly Lys Glu Ile Lys Ile Thr Pro Gln Ser Ser Ile Thr Glu Ala Glu
    440             445                 450 ttg aca ggt tat ggc act gtc aca atg gag tgc tct cca aga acg ggc      1506
Leu Thr Gly Tyr Gly Thr Val Thr Met Glu Cys Ser Pro Arg Thr Gly
455             460                 465                 470 ctc gac ttc aat gag atg gtt ttg ctg cag atg gaa aat aaa gct tgg      1554
Leu Asp Phe Asn Glu Met Val Leu Leu Gln Met Glu Asn Lys Ala Trp
                475                 480                 485 ctg gtg cac agg caa tgg ttc cta gac ctg ccg tta cca tgg ttg ccc      1602
Leu Val His Arg Gln Trp Phe Leu Asp Leu Pro Leu Pro Trp Leu Pro
            490                 495                 500 gga gcg gac aca caa gag tca aat tgg ata cag aag gag aca ttg gtc      1650
Gly Ala Asp Thr Gln Glu Ser Asn Trp Ile Gln Lys Glu Thr Leu Val
        505                 510                 515 act ttc aaa aat ccc cat gcg aag aaa cag gat gtt gtt gtt tta gga      1698
Thr Phe Lys Asn Pro His Ala Lys Lys Gln Asp Val Val Val Leu Gly
    520                 525                 530 tcc caa gaa ggg gcc atg cac aca gca ctt aca ggg gcc aca gaa atc      1746
Ser Gln Glu Gly Ala Met His Thr Ala Leu Thr Gly Ala Thr Glu Ile
535             540                 545                 550 caa atg tca tca gga aac tta ctc ttc aca gga cat ctc aag tgc agg      1794
Gln Met Ser Ser Gly Asn Leu Leu Phe Thr Gly His Leu Lys Cys Arg
                555                 560                 565 ctg aga atg gac aag cta cag ctc aaa gga atg tca tac tct atg tgc      1842
Leu Arg Met Asp Lys Leu Gln Leu Lys Gly Met Ser Tyr Ser Met Cys
            570                 575                 580 aca gga aag ttt aaa gtt gtg aag gaa ata gca gaa aca caa cat gga      1890
Thr Gly Lys Phe Lys Val Val Lys Glu Ile Ala Glu Thr Gln His Gly
        585                 590                 595 aca ata gtt atc aga gtg caa tat gaa ggg gac ggc tct cca tgc aag      1938
Thr Ile Val Ile Arg Val Gln Tyr Glu Gly Asp Gly Ser Pro Cys Lys
    600                 605                 610 atc cct ttt gag ata atg gat ttg gaa aaa aga cat gtc tta ggt cgc      1986
Ile Pro Phe Glu Ile Met Asp Leu Glu Lys Arg His Val Leu Gly Arg
615             620                 625                 630 ctg att aca gtc aac cca att gtg aca gaa aaa gat agc cca gtc aac      2034
Leu Ile Thr Val Asn Pro Ile Val Thr Glu Lys Asp Ser Pro Val Asn
                635                 640                 645 ata gaa gca gaa cct cca ttt gga gac agc tac atc atc ata gga gta      2082
Ile Glu Ala Glu Pro Pro Phe Gly Asp Ser Tyr Ile Ile Ile Gly Val
            650                 655                 660 gag ccg gga caa ctg aag ctc aac tgg ttt aag aaa gga agt tct atc      2130
Glu Pro Gly Gln Leu Lys Leu Asn Trp Phe Lys Lys Gly Ser Ser Ile
        665                 670                 675 ggc caa atg ttt gag aca aca atg agg ggg gcg aag aga atg gcc att      2178
Gly Gln Met Phe Glu Thr Thr Met Arg Gly Ala Lys Arg Met Ala Ile
    680                 685                 690 tta ggt gac aca gcc tgg gat ttt gga tcc ttg gga gga gtg ttt aca      2226
Leu Gly Asp Thr Ala Trp Asp Phe Gly Ser Leu Gly Gly Val Phe Thr
695             700                 705                 710 tct ata gga aag gct ctc cac caa gtc ttt gga gca atc tat gga gct      2274
Ser Ile Gly Lys Ala Leu His Gln Val Phe Gly Ala Ile Tyr Gly Ala
                715                 720                 725 gcc ttc agt ggg gtt tca tgg act atg aaa atc ctc ata gga gtc att      2322
Ala Phe Ser Gly Val Ser Trp Thr Met Lys Ile Leu Ile Gly Val Ile
            730                 735                 740 atc aca tgg ata gga atg aat tca cgc agc acc tca ctg tct gtg aca      2370
Ile Thr Trp Ile Gly Met Asn Ser Arg Ser Thr Ser Leu Ser Val Thr
        745                 750                 755
```

```
cta gta ttg gtg gga att gtg aca ctg tat ttg gga gtc atg gtg cag          2418
Leu Val Leu Val Gly Ile Val Thr Leu Tyr Leu Gly Val Met Val Gln
    760                 765                 770 gcc gat agt ggt tgc gtt gtg agc tgg aaa aac aaa gaa ctg aaa tgt          2466
Ala Asp Ser Gly Cys Val Val Ser Trp Lys Asn Lys Glu Leu Lys Cys
775                 780                 785                 790 ggc agt ggg att ttc atc aca gac aac gtg cac aca tgg aca gaa caa          2514
Gly Ser Gly Ile Phe Ile Thr Asp Asn Val His Thr Trp Thr Glu Gln
                795                 800                 805 tac aaa ttc caa cca gaa tcc cct tca aaa cta gct tca gct atc cag          2562
Tyr Lys Phe Gln Pro Glu Ser Pro Ser Lys Leu Ala Ser Ala Ile Gln
        810                 815                 820 aaa gcc cat gaa gag gac att tgt gga atc cgc tca gta aca aga ctg          2610
Lys Ala His Glu Glu Asp Ile Cys Gly Ile Arg Ser Val Thr Arg Leu
    825                 830                 835 gag aat ctg atg tgg aaa caa ata aca cca gaa ttg aat cac att cta          2658
Glu Asn Leu Met Trp Lys Gln Ile Thr Pro Glu Leu Asn His Ile Leu
840                 845                 850 tca gaa aat gag gtg aag tta act att atg aca gga gac atc aaa gga          2706
Ser Glu Asn Glu Val Lys Leu Thr Ile Met Thr Gly Asp Ile Lys Gly
855                 860                 865                 870 atc atg cag gca gga aaa cga tct ctg cgg cct cag ccc act gag ctg          2754
Ile Met Gln Ala Gly Lys Arg Ser Leu Arg Pro Gln Pro Thr Glu Leu
                875                 880                 885 aag tat tca tgg aaa aca tgg ggc aaa gca aaa atg ctc tct aca gag          2802
Lys Tyr Ser Trp Lys Thr Trp Gly Lys Ala Lys Met Leu Ser Thr Glu
        890                 895                 900 tct cat aac cag acc ttt ctc att gat ggc ccc gaa aca gca gaa tgc          2850
Ser His Asn Gln Thr Phe Leu Ile Asp Gly Pro Glu Thr Ala Glu Cys
    905                 910                 915 ccc aac aca aat aga gct tgg aat tcg ttg gaa gtt gaa gac tat ggc          2898
Pro Asn Thr Asn Arg Ala Trp Asn Ser Leu Glu Val Glu Asp Tyr Gly
920                 925                 930 ttt gga gta ttc acc acc aat ata tgg cta aaa ttg aaa gaa aaa cag          2946
Phe Gly Val Phe Thr Thr Asn Ile Trp Leu Lys Leu Lys Glu Lys Gln
935                 940                 945                 950 gat gta ttc tgc gac tca aaa ctc atg tca gcg gcc ata aaa gac aac          2994
Asp Val Phe Cys Asp Ser Lys Leu Met Ser Ala Ala Ile Lys Asp Asn
                955                 960                 965 aga gcc gtc cat gcc gat atg ggt tat tgg ata gaa agt gca ctc aat          3042
Arg Ala Val His Ala Asp Met Gly Tyr Trp Ile Glu Ser Ala Leu Asn
        970                 975                 980 gac aca tgg aag ata gag aaa gcc tct ttc att gaa gtt aaa aac tgc          3090
Asp Thr Trp Lys Ile Glu Lys Ala Ser Phe Ile Glu Val Lys Asn Cys
    985                 990                 995 cac tgg  cca aaa tca cac acc  ctc tgg agc aat gga  gtg cta gaa           3135
His Trp  Pro Lys Ser His Thr  Leu Trp Ser Asn Gly  Val Leu Glu
    1000                 1005                 1010 agt gag  atg ata att cca aag  aat ctc gct gga cca  gtg tct caa           3180
Ser Glu  Met Ile Ile Pro Lys  Asn Leu Ala Gly Pro  Val Ser Gln
1015                 1020                 1025 cac aac  tat aga cca ggc tac  cat aca caa ata aca  gga cca tgg           3225
His Asn  Tyr Arg Pro Gly Tyr  His Thr Gln Ile Thr  Gly Pro Trp
    1030                 1035                 1040 cat cta  ggt aag ctt gag atg  gac ttt gat ttc tgt  gat gga aca           3270
His Leu  Gly Lys Leu Glu Met  Asp Phe Asp Phe Cys  Asp Gly Thr
    1045                 1050                 1055 aca gtg  gta gtg act gag gac  tgc gga aat aga gga  ccc tct ttg           3315
Thr Val  Val Val Thr Glu Asp  Cys Gly Asn Arg Gly  Pro Ser Leu
    1060                 1065                 1070
```

```
aga aca acc act gcc tct gga aaa ctc ata aca gaa tgg tgc tgc          3360
Arg Thr Thr Thr Ala Ser Gly Lys Leu Ile Thr Glu Trp Cys Cys
    1075                1080                1085 cga tct tgc aca tta cca ccg cta aga tac aga ggt gag gat ggg          3405
Arg Ser Cys Thr Leu Pro Pro Leu Arg Tyr Arg Gly Glu Asp Gly
    1090                1095                1100 tgc tgg tac ggg atg gaa atc aga cca ttg aag gag aaa gaa gag          3450
Cys Trp Tyr Gly Met Glu Ile Arg Pro Leu Lys Glu Lys Glu Glu
    1105                1110                1115 aat ttg gtc aac tcc ttg gtc aca gct gga cat ggg cag gtc gac          3495
Asn Leu Val Asn Ser Leu Val Thr Ala Gly His Gly Gln Val Asp
    1120                1125                1130 aac ttt tca cta gga gtc ttg gga atg gca ttg ttc ctg gag gaa          3540
Asn Phe Ser Leu Gly Val Leu Gly Met Ala Leu Phe Leu Glu Glu
    1135                1140                1145 atg ctt agg acc cga gta gga acg aaa cat gca ata cta cta gtt          3585
Met Leu Arg Thr Arg Val Gly Thr Lys His Ala Ile Leu Leu Val
    1150                1155                1160 gca gtt tct ttt gtg aca ttg atc aca ggg aac atg tcc ttt aga          3630
Ala Val Ser Phe Val Thr Leu Ile Thr Gly Asn Met Ser Phe Arg
    1165                1170                1175 gac ctg gga aga gtg atg gtt atg gta ggc gcc act atg acg gat          3675
Asp Leu Gly Arg Val Met Val Met Val Gly Ala Thr Met Thr Asp
    1180                1185                1190 gac ata ggt atg ggc gtg act tat ctt gcc cta cta gca gcc ttc          3720
Asp Ile Gly Met Gly Val Thr Tyr Leu Ala Leu Leu Ala Ala Phe
    1195                1200                1205 aaa gtc aga cca act ttt gca gct gga cta ctc ttg aga aag ctg          3765
Lys Val Arg Pro Thr Phe Ala Ala Gly Leu Leu Leu Arg Lys Leu
    1210                1215                1220 acc tcc aag gaa ttg atg atg act act ata gga att gta ctc ctc          3810
Thr Ser Lys Glu Leu Met Met Thr Thr Ile Gly Ile Val Leu Leu
    1225                1230                1235 tcc cag agc acc ata cca gag acc att ctt gag ttg act gat gcg          3855
Ser Gln Ser Thr Ile Pro Glu Thr Ile Leu Glu Leu Thr Asp Ala
    1240                1245                1250 tta gcc tta ggc atg atg gtc ctc aaa atg gtg aga aat atg gaa          3900
Leu Ala Leu Gly Met Met Val Leu Lys Met Val Arg Asn Met Glu
    1255                1260                1265 aag tat caa ttg gca gtg act atc atg gct atc ttg tgc gtc cca          3945
Lys Tyr Gln Leu Ala Val Thr Ile Met Ala Ile Leu Cys Val Pro
    1270                1275                1280 aac gca gtg ata tta caa aac gca tgg aaa gtg agt tgc aca ata          3990
Asn Ala Val Ile Leu Gln Asn Ala Trp Lys Val Ser Cys Thr Ile
    1285                1290                1295 ttg gca gtg gtg tcc gtt tcc cca ctg ttc tta aca tcc tca cag          4035
Leu Ala Val Val Ser Val Ser Pro Leu Phe Leu Thr Ser Ser Gln
    1300                1305                1310 caa aaa aca gat tgg ata cca tta gca ttg acg atc aaa ggt ctc          4080
Gln Lys Thr Asp Trp Ile Pro Leu Ala Leu Thr Ile Lys Gly Leu
    1315                1320                1325 aat cca aca gct att ttt cta aca acc ctc tca aga acc agc aag          4125
Asn Pro Thr Ala Ile Phe Leu Thr Thr Leu Ser Arg Thr Ser Lys
    1330                1335                1340 aaa agg agc tgg cca tta aat gag gct atc atg gca gtc ggg atg          4170
Lys Arg Ser Trp Pro Leu Asn Glu Ala Ile Met Ala Val Gly Met
    1345                1350                1355 gtg agc att tta gcc agt tct ctc cta aaa aat gat att ccc atg          4215
Val Ser Ile Leu Ala Ser Ser Leu Leu Lys Asn Asp Ile Pro Met
    1360                1365                1370
```

```
aca gga cca tta gtg gct gga ggg ctc ctc act gtg tgc tac gtg         4260
Thr Gly Pro Leu Val Ala Gly Gly Leu Leu Thr Val Cys Tyr Val
    1375            1380                1385 ctc act gga cga tcg gcc gat ttg gaa ctg gag aga gca gcc gat         4305
Leu Thr Gly Arg Ser Ala Asp Leu Glu Leu Glu Arg Ala Ala Asp
    1390            1395                1400 gtc aaa tgg gaa gac cag gca gag ata tca gga agc agt cca atc         4350
Val Lys Trp Glu Asp Gln Ala Glu Ile Ser Gly Ser Ser Pro Ile
    1405            1410                1415 ctg tca ata aca ata tca gaa gat ggt agc atg tcg ata aaa aat         4395
Leu Ser Ile Thr Ile Ser Glu Asp Gly Ser Met Ser Ile Lys Asn
    1420            1425                1430 gaa gag gaa gaa caa aca ctg acc ata ctc att aga aca gga ttg         4440
Glu Glu Glu Glu Gln Thr Leu Thr Ile Leu Ile Arg Thr Gly Leu
    1435            1440                1445 ctg gtg atc tca gga ctt ttt cct gta tca ata cca atc acg gca         4485
Leu Val Ile Ser Gly Leu Phe Pro Val Ser Ile Pro Ile Thr Ala
    1450            1455                1460 gca gca tgg tac ctg tgg gaa gtg aag aaa caa cgg gcc gga gta         4530
Ala Ala Trp Tyr Leu Trp Glu Val Lys Lys Gln Arg Ala Gly Val
    1465            1470                1475 ttg tgg gat gtt cct tca ccc cca ccc atg gga aag gct gaa ctg         4575
Leu Trp Asp Val Pro Ser Pro Pro Pro Met Gly Lys Ala Glu Leu
    1480            1485                1490 gaa gat gga gcc tat aga att aag caa aaa ggg att ctt gga tat         4620
Glu Asp Gly Ala Tyr Arg Ile Lys Gln Lys Gly Ile Leu Gly Tyr
    1495            1500                1505 tcc cag atc gga gcc gga gtt tac aaa gaa gga aca ttc cat aca         4665
Ser Gln Ile Gly Ala Gly Val Tyr Lys Glu Gly Thr Phe His Thr
    1510            1515                1520 atg tgg cat gtc aca cgt ggc gct gtt cta atg cat aaa gga aag         4710
Met Trp His Val Thr Arg Gly Ala Val Leu Met His Lys Gly Lys
    1525            1530                1535 agg att gaa cca aca tgg gcg gac gtc aag aaa gac cta ata tca         4755
Arg Ile Glu Pro Thr Trp Ala Asp Val Lys Lys Asp Leu Ile Ser
    1540            1545                1550 tat gga gga ggc tgg aag tta gaa gga gaa tgg aag gaa gga gaa         4800
Tyr Gly Gly Gly Trp Lys Leu Glu Gly Glu Trp Lys Glu Gly Glu
    1555            1560                1565 gaa gtc cag gta ttg gca ctg gag cct gga aaa aat cca aga gcc         4845
Glu Val Gln Val Leu Ala Leu Glu Pro Gly Lys Asn Pro Arg Ala
    1570            1575                1580 gtc caa acg aaa cct ggt ctt ttc aaa acc aac gcc gga aca ata         4890
Val Gln Thr Lys Pro Gly Leu Phe Lys Thr Asn Ala Gly Thr Ile
    1585            1590                1595 ggt gct gta tct ctg gac ttt tct cct gga acg tca gga tct cca         4935
Gly Ala Val Ser Leu Asp Phe Ser Pro Gly Thr Ser Gly Ser Pro
    1600            1605                1610 att atc gac aaa aaa gga aaa gtt gtg ggt ctt tat ggt aat ggt         4980
Ile Ile Asp Lys Lys Gly Lys Val Val Gly Leu Tyr Gly Asn Gly
    1615            1620                1625 gtt gtt aca agg agt gga gca tat gtg agt gct ata gcc cag act         5025
Val Val Thr Arg Ser Gly Ala Tyr Val Ser Ala Ile Ala Gln Thr
    1630            1635                1640 gaa aaa agc att gaa gac aac cca gag atc gaa gat cac att ttc         5070
Glu Lys Ser Ile Glu Asp Asn Pro Glu Ile Glu Asp His Ile Phe
    1645            1650                1655 cga aag aga aga ctg acc atc atg gac ctc cac cca gga gcg gga         5115
Arg Lys Arg Arg Leu Thr Ile Met Asp Leu His Pro Gly Ala Gly
    1660            1665                1670
```

```
aag acg aag aga tac ctt ccg gcc ata gtc aga gaa gct ata aaa       5160
Lys Thr Lys Arg Tyr Leu Pro Ala Ile Val Arg Glu Ala Ile Lys
    1675            1680                1685 cgg ggt ttg aga aca tta atc ttg gcc ccc act aga gtt gtg gca       5205
Arg Gly Leu Arg Thr Leu Ile Leu Ala Pro Thr Arg Val Val Ala
1690                1695                1700 gct gaa atg gag gaa gcc ctt aga gga ctt cca ata aga tac cag       5250
Ala Glu Met Glu Glu Ala Leu Arg Gly Leu Pro Ile Arg Tyr Gln
    1705            1710                1715 acc cca gcc atc aga gct gag cac acc ggg cgg gag att gtg gac       5295
Thr Pro Ala Ile Arg Ala Glu His Thr Gly Arg Glu Ile Val Asp
1720                1725                1730 cta atg tgt cat gcc aca ttt acc atg agg ctg cta tca cca gtt       5340
Leu Met Cys His Ala Thr Phe Thr Met Arg Leu Leu Ser Pro Val
    1735            1740                1745 aga gtg cca aac tac aac ctg att atc atg gac gaa gcc cat ttc       5385
Arg Val Pro Asn Tyr Asn Leu Ile Ile Met Asp Glu Ala His Phe
1750                1755                1760 aca gac cca gca agt ata gca gct aga gga tac atc tca act cga       5430
Thr Asp Pro Ala Ser Ile Ala Ala Arg Gly Tyr Ile Ser Thr Arg
    1765            1770                1775 gtg gag atg ggt gag gca gct ggg att ttt atg aca gcc act ccc       5475
Val Glu Met Gly Glu Ala Ala Gly Ile Phe Met Thr Ala Thr Pro
1780                1785                1790 ccg gga agc aga gac cca ttt cct cag agc aat gca cca atc ata       5520
Pro Gly Ser Arg Asp Pro Phe Pro Gln Ser Asn Ala Pro Ile Ile
    1795            1800                1805 gat gaa gaa aga gaa atc cct gaa cgc tcg tgg aat tcc gga cat       5565
Asp Glu Glu Arg Glu Ile Pro Glu Arg Ser Trp Asn Ser Gly His
1810                1815                1820 gaa tgg gtc acg gat ttt aaa ggg aag act gtt tgg ttc gtt cca       5610
Glu Trp Val Thr Asp Phe Lys Gly Lys Thr Val Trp Phe Val Pro
    1825            1830                1835 agt ata aaa gca gga aat gat ata gca gct tgc ctg agg aaa aat       5655
Ser Ile Lys Ala Gly Asn Asp Ile Ala Ala Cys Leu Arg Lys Asn
1840                1845                1850 gga aag aaa gtg ata caa ctc agt agg aag acc ttt gat tct gag       5700
Gly Lys Lys Val Ile Gln Leu Ser Arg Lys Thr Phe Asp Ser Glu
    1855            1860                1865 tat gtc aag act aga acc aat gat tgg gac ttc gtg gtt aca act       5745
Tyr Val Lys Thr Arg Thr Asn Asp Trp Asp Phe Val Val Thr Thr
1870                1875                1880 gac att tca gaa atg ggt gcc aat ttc aag gct gag agg gtt ata       5790
Asp Ile Ser Glu Met Gly Ala Asn Phe Lys Ala Glu Arg Val Ile
    1885            1890                1895 gac ccc aga cgc tgc atg aaa cca gtc ata cta aca gat ggt gaa       5835
Asp Pro Arg Arg Cys Met Lys Pro Val Ile Leu Thr Asp Gly Glu
1900                1905                1910 gag cgg gtg att ctg gca gga cct atg cca gtg acc cac tct agt       5880
Glu Arg Val Ile Leu Ala Gly Pro Met Pro Val Thr His Ser Ser
    1915            1920                1925 gca gca caa aga aga ggg aga ata gga aga aat cca aaa aat gag       5925
Ala Ala Gln Arg Arg Gly Arg Ile Gly Arg Asn Pro Lys Asn Glu
1930                1935                1940 aat gac cag tac ata tac atg ggg gaa cct ctg gaa aat gat gaa       5970
Asn Asp Gln Tyr Ile Tyr Met Gly Glu Pro Leu Glu Asn Asp Glu
    1945            1950                1955 gac tgt gca cac tgg aaa gaa gct aaa atg ctc cta gat aac atc       6015
Asp Cys Ala His Trp Lys Glu Ala Lys Met Leu Leu Asp Asn Ile
1960                1965                1970
```

-continued

```
aac acg cca gaa gga atc att cct agc atg ttc gaa cca gag cgt      6060
Asn Thr Pro Glu Gly Ile Ile Pro Ser Met Phe Glu Pro Glu Arg
1975                1980                1985 gaa aag gtg gat gcc att gat ggc gaa tac cgc ttg aga gga gaa      6105
Glu Lys Val Asp Ala Ile Asp Gly Glu Tyr Arg Leu Arg Gly Glu
    1990                1995                2000 gca agg aaa acc ttt gta gac tta atg aga aga gga gac cta cca      6150
Ala Arg Lys Thr Phe Val Asp Leu Met Arg Arg Gly Asp Leu Pro
2005                2010                2015 gtc tgg ttg gcc tac aga gtg gca gct gaa ggc atc aac tac gca      6195
Val Trp Leu Ala Tyr Arg Val Ala Ala Glu Gly Ile Asn Tyr Ala
    2020                2025                2030 gac aga agg tgg tgt ttt gat gga gtc aag aac aac caa atc cta      6240
Asp Arg Arg Trp Cys Phe Asp Gly Val Lys Asn Asn Gln Ile Leu
2035                2040                2045 gaa gaa aac gtg gaa gtt gaa atc tgg aca aaa gaa ggg gaa agg      6285
Glu Glu Asn Val Glu Val Glu Ile Trp Thr Lys Glu Gly Glu Arg
    2050                2055                2060 aag aaa ttg aaa ccc aga tgg ttg gat gct agg atc tat tct gac      6330
Lys Lys Leu Lys Pro Arg Trp Leu Asp Ala Arg Ile Tyr Ser Asp
2065                2070                2075 cca ctg gcg cta aaa gaa ttt aag gaa ttt gca gcc gga aga aag      6375
Pro Leu Ala Leu Lys Glu Phe Lys Glu Phe Ala Ala Gly Arg Lys
    2080                2085                2090 tct ctg acc ctg aac cta atc aca gaa atg ggt agg ctc cca acc      6420
Ser Leu Thr Leu Asn Leu Ile Thr Glu Met Gly Arg Leu Pro Thr
2095                2100                2105 ttc atg act cag aag gca aga gac gca ctg gac aac tta gca gtg      6465
Phe Met Thr Gln Lys Ala Arg Asp Ala Leu Asp Asn Leu Ala Val
    2110                2115                2120 ctg cac acg gct gag gca ggt gga agg gcg tac aac cat gct ctc      6510
Leu His Thr Ala Glu Ala Gly Gly Arg Ala Tyr Asn His Ala Leu
2125                2130                2135 agt gaa ctg ccg gag acc ctg gag aca ttg ctt tta ctg aca ctt      6555
Ser Glu Leu Pro Glu Thr Leu Glu Thr Leu Leu Leu Leu Thr Leu
    2140                2145                2150 ctg gct aca gtc acg gga ggg atc ttt tta ttc ttg atg agc gca      6600
Leu Ala Thr Val Thr Gly Gly Ile Phe Leu Phe Leu Met Ser Ala
2155                2160                2165 agg ggc ata ggg aag atg acc ctg gga atg tgc tgc ata atc acg      6645
Arg Gly Ile Gly Lys Met Thr Leu Gly Met Cys Cys Ile Ile Thr
    2170                2175                2180 gct agc atc ctc cta tgg tac gca caa ata cag cca cac tgg ata      6690
Ala Ser Ile Leu Leu Trp Tyr Ala Gln Ile Gln Pro His Trp Ile
2185                2190                2195 gca gct tca ata ata ctg gag ttt ttt ctc ata gtt ttg ctt att      6735
Ala Ala Ser Ile Ile Leu Glu Phe Phe Leu Ile Val Leu Leu Ile
    2200                2205                2210 cca gaa cct gaa aaa cag aga aca ccc caa gac aac caa ctg acc      6780
Pro Glu Pro Glu Lys Gln Arg Thr Pro Gln Asp Asn Gln Leu Thr
2215                2220                2225 tac gtt gtc ata gcc atc ctc aca gtg gtg gcc gca acc atg gca      6825
Tyr Val Val Ile Ala Ile Leu Thr Val Val Ala Ala Thr Met Ala
    2230                2235                2240 aac gag atg ggt ttc cta gaa aaa acg aag aaa gat ctc gga ttg      6870
Asn Glu Met Gly Phe Leu Glu Lys Thr Lys Lys Asp Leu Gly Leu
2245                2250                2255 gga agc att gca acc cag caa ccc gag agc aac atc ctg gac ata      6915
Gly Ser Ile Ala Thr Gln Gln Pro Glu Ser Asn Ile Leu Asp Ile
    2260                2265                2270
```

```
gat cta cgt cct gca tca gca tgg acg ctg tat gcc gtg gcc aca    6960
Asp Leu Arg Pro Ala Ser Ala Trp Thr Leu Tyr Ala Val Ala Thr
    2275            2280                2285 aca ttt gtt aca cca atg ttg aga cat agc att gaa aat tcc tca    7005
Thr Phe Val Thr Pro Met Leu Arg His Ser Ile Glu Asn Ser Ser
2290            2295                2300 gtg aat gtg tcc cta aca gct ata gcc aac caa gcc aca gtg tta    7050
Val Asn Val Ser Leu Thr Ala Ile Ala Asn Gln Ala Thr Val Leu
    2305            2310                2315 atg ggt ctc ggg aaa gga tgg cca ttg tca aag atg gac atc gga    7095
Met Gly Leu Gly Lys Gly Trp Pro Leu Ser Lys Met Asp Ile Gly
2320            2325                2330 gtt ccc ctt ctc gcc att gga tgc tac tca caa gtc aac ccc ata    7140
Val Pro Leu Leu Ala Ile Gly Cys Tyr Ser Gln Val Asn Pro Ile
    2335            2340                2345 act ctc aca gca gct ctt ttc tta ttg gta gca cat tat gcc atc    7185
Thr Leu Thr Ala Ala Leu Phe Leu Leu Val Ala His Tyr Ala Ile
2350            2355                2360 ata ggg cca gga ctc caa gca aaa gca acc aga gaa gct cag aaa    7230
Ile Gly Pro Gly Leu Gln Ala Lys Ala Thr Arg Glu Ala Gln Lys
    2365            2370                2375 aga gca gcg gcg ggc atc atg aaa aac cca act gtc gat gga ata    7275
Arg Ala Ala Ala Gly Ile Met Lys Asn Pro Thr Val Asp Gly Ile
2380            2385                2390 aca gtg att gac cta gat cca ata cct tat gat cca aag ttt gaa    7320
Thr Val Ile Asp Leu Asp Pro Ile Pro Tyr Asp Pro Lys Phe Glu
    2395            2400                2405 aag cag ttg gga caa gta atg ctc cta gtc ctc tgc gtg act caa    7365
Lys Gln Leu Gly Gln Val Met Leu Leu Val Leu Cys Val Thr Gln
2410            2415                2420 gta ttg atg atg agg act aca tgg gct ctg tgt gag gct tta acc    7410
Val Leu Met Met Arg Thr Thr Trp Ala Leu Cys Glu Ala Leu Thr
    2425            2430                2435 tta gct acc ggg ccc atc tcc aca ttg tgg gaa gga aat cca ggg    7455
Leu Ala Thr Gly Pro Ile Ser Thr Leu Trp Glu Gly Asn Pro Gly
2440            2445                2450 agg ttt tgg aac act acc att gcg gtg tca atg gct aac att ttt    7500
Arg Phe Trp Asn Thr Thr Ile Ala Val Ser Met Ala Asn Ile Phe
    2455            2460                2465 aga ggg agt tac ttg gcc gga gct gga ctt ctc ttt tct att atg    7545
Arg Gly Ser Tyr Leu Ala Gly Ala Gly Leu Leu Phe Ser Ile Met
2470            2475                2480 aag aac aca acc aac aca aga agg gga act ggc aac ata gga gag    7590
Lys Asn Thr Thr Asn Thr Arg Arg Gly Thr Gly Asn Ile Gly Glu
    2485            2490                2495 acg ctt gga gag aaa tgg aaa agc cga ttg aac gca ttg gga aaa    7635
Thr Leu Gly Glu Lys Trp Lys Ser Arg Leu Asn Ala Leu Gly Lys
2500            2505                2510 agt gaa ttc cag atc tac aag aaa agt gga atc cag gaa gtg gat    7680
Ser Glu Phe Gln Ile Tyr Lys Lys Ser Gly Ile Gln Glu Val Asp
    2515            2520                2525 aga acc tta gca aaa gaa ggc att aaa aga gga gaa acg gac cat    7725
Arg Thr Leu Ala Lys Glu Gly Ile Lys Arg Gly Glu Thr Asp His
2530            2535                2540 cac gct gtg tcg cga ggc tca gca aaa ctg aga tgg ttc gtt gag    7770
His Ala Val Ser Arg Gly Ser Ala Lys Leu Arg Trp Phe Val Glu
    2545            2550                2555 aga aac atg gtc aca cca gaa ggg aaa gta gtg gac ctc ggt tgt    7815
Arg Asn Met Val Thr Pro Glu Gly Lys Val Val Asp Leu Gly Cys
2560            2565                2570
```

```
ggc aga gga ggc tgg tca tac tat tgt gga gga cta aag aat gta      7860
Gly Arg Gly Gly Trp Ser Tyr Tyr Cys Gly Gly Leu Lys Asn Val
2575             2580                 2585 aga gaa gtc aaa ggc cta aca aaa gga gga cca gga cac gaa gaa      7905
Arg Glu Val Lys Gly Leu Thr Lys Gly Gly Pro Gly His Glu Glu
    2590             2595                 2600 ccc atc ccc atg tca aca tat ggg tgg aat cta gtg cgt ctt caa      7950
Pro Ile Pro Met Ser Thr Tyr Gly Trp Asn Leu Val Arg Leu Gln
2605             2610                 2615 agt gga gtt gac gtt ttc ttc atc ccg cca gaa aag tgt gac aca      7995
Ser Gly Val Asp Val Phe Phe Ile Pro Pro Glu Lys Cys Asp Thr
    2620             2625                 2630 tta ttg tgt gac ata ggg gag tca tca cca aat ccc aca gtg gaa      8040
Leu Leu Cys Asp Ile Gly Glu Ser Ser Pro Asn Pro Thr Val Glu
2635             2640                 2645 gca gga cga aca ctc aga gtc ctt aac tta gta gaa aat tgg ttg      8085
Ala Gly Arg Thr Leu Arg Val Leu Asn Leu Val Glu Asn Trp Leu
    2650             2655                 2660 aac aac aac act caa ttt tgc ata aag gtt ctc aac cca tat atg      8130
Asn Asn Asn Thr Gln Phe Cys Ile Lys Val Leu Asn Pro Tyr Met
2665             2670                 2675 ccc tca gtc ata gaa aaa atg gaa gca cta caa agg aaa tat gga      8175
Pro Ser Val Ile Glu Lys Met Glu Ala Leu Gln Arg Lys Tyr Gly
    2680             2685                 2690 gga gcc tta gtg agg aat cca ctc tca cga aac tcc aca cat gag      8220
Gly Ala Leu Val Arg Asn Pro Leu Ser Arg Asn Ser Thr His Glu
2695             2700                 2705 atg tac tgg gta tcc aat gct tcc ggg aac ata gtg tca tca gtg      8265
Met Tyr Trp Val Ser Asn Ala Ser Gly Asn Ile Val Ser Ser Val
    2710             2715                 2720 aac atg att tca agg atg ttg atc aac aga ttt aca atg aga tac      8310
Asn Met Ile Ser Arg Met Leu Ile Asn Arg Phe Thr Met Arg Tyr
2725             2730                 2735 aag aaa gcc act tac gag ccg gat gtt gac ctc gga agc gga acc      8355
Lys Lys Ala Thr Tyr Glu Pro Asp Val Asp Leu Gly Ser Gly Thr
    2740             2745                 2750 cgt aac atc ggg att gaa agt gag ata cca aac cta gat ata att      8400
Arg Asn Ile Gly Ile Glu Ser Glu Ile Pro Asn Leu Asp Ile Ile
2755             2760                 2765 ggg aaa aga ata gaa aaa ata aag caa gag cat gaa aca tca tgg      8445
Gly Lys Arg Ile Glu Lys Ile Lys Gln Glu His Glu Thr Ser Trp
    2770             2775                 2780 cac tat gac caa gac cac cca tac aaa acg tgg gca tac cat ggt      8490
His Tyr Asp Gln Asp His Pro Tyr Lys Thr Trp Ala Tyr His Gly
2785             2790                 2795 agc tat gaa aca aaa cag act gga tca gca tca tcc atg gtc aac      8535
Ser Tyr Glu Thr Lys Gln Thr Gly Ser Ala Ser Ser Met Val Asn
    2800             2805                 2810 gga gtg gtc agg ctg ctg aca aaa cct tgg gac gtt gtc ccc atg      8580
Gly Val Val Arg Leu Leu Thr Lys Pro Trp Asp Val Val Pro Met
2815             2820                 2825 gtg aca cag atg gca atg aca gac acg act cca ttt gga caa cag      8625
Val Thr Gln Met Ala Met Thr Asp Thr Thr Pro Phe Gly Gln Gln
    2830             2835                 2840 cgc gtt ttt aaa gag aaa gtg gac acg aga acc caa gaa ccg aaa      8670
Arg Val Phe Lys Glu Lys Val Asp Thr Arg Thr Gln Glu Pro Lys
2845             2850                 2855 gaa ggc acg aag aaa cta atg aaa ata aca gca gag tgg ctt tgg      8715
Glu Gly Thr Lys Lys Leu Met Lys Ile Thr Ala Glu Trp Leu Trp
    2860             2865                 2870
```

```
aaa gaa tta ggg aag aaa aag aca ccc agg atg tgc acc aga gaa    8760
Lys Glu Leu Gly Lys Lys Lys Thr Pro Arg Met Cys Thr Arg Glu
    2875            2880            2885 gaa ttc aca aga aag gtg aga agc aat gca gcc ttg ggg gcc ata    8805
Glu Phe Thr Arg Lys Val Arg Ser Asn Ala Ala Leu Gly Ala Ile
    2890            2895            2900 ttc act gat gag aac aag tgg aag tcg gca cgt gag gct gtt gaa    8850
Phe Thr Asp Glu Asn Lys Trp Lys Ser Ala Arg Glu Ala Val Glu
    2905            2910            2915 gat agt agg ttt tgg gag ctg gtt gac aag gaa agg aat ctc cat    8895
Asp Ser Arg Phe Trp Glu Leu Val Asp Lys Glu Arg Asn Leu His
    2920            2925            2930 ctt gaa gga aag tgt gaa aca tgt gtg tac aac atg atg gga aaa    8940
Leu Glu Gly Lys Cys Glu Thr Cys Val Tyr Asn Met Met Gly Lys
    2935            2940            2945 aga gag aag aag cta ggg gaa ttc ggc aag gca aaa ggc agc aga    8985
Arg Glu Lys Lys Leu Gly Glu Phe Gly Lys Ala Lys Gly Ser Arg
    2950            2955            2960 gcc ata tgg tac atg tgg ctt gga gca cgc ttc tta gag ttt gaa    9030
Ala Ile Trp Tyr Met Trp Leu Gly Ala Arg Phe Leu Glu Phe Glu
    2965            2970            2975 gcc cta gga ttc tta aat gaa gat cac tgg ttc tcc aga gag aac    9075
Ala Leu Gly Phe Leu Asn Glu Asp His Trp Phe Ser Arg Glu Asn
    2980            2985            2990 tcc ctg agt gga gtg gaa gga gaa ggg ctg cac aag cta ggt tac    9120
Ser Leu Ser Gly Val Glu Gly Glu Gly Leu His Lys Leu Gly Tyr
    2995            3000            3005 att cta aga gac gtg agc aag aaa gag gga gga gca atg tat gcc    9165
Ile Leu Arg Asp Val Ser Lys Lys Glu Gly Gly Ala Met Tyr Ala
    3010            3015            3020 gat gac acc gca gga tgg gat aca aaa atc aca cta gaa gac cta    9210
Asp Asp Thr Ala Gly Trp Asp Thr Lys Ile Thr Leu Glu Asp Leu
    3025            3030            3035 aaa aat gaa gag atg gta aca aac cac atg gaa gga gaa cac aag    9255
Lys Asn Glu Glu Met Val Thr Asn His Met Glu Gly Glu His Lys
    3040            3045            3050 aaa cta gcc gag gcc att ttc aaa cta acg tac caa aac aag gtg    9300
Lys Leu Ala Glu Ala Ile Phe Lys Leu Thr Tyr Gln Asn Lys Val
    3055            3060            3065 gtg cgt gtg caa aga cca aca cca aga ggc aca gta atg gac atc    9345
Val Arg Val Gln Arg Pro Thr Pro Arg Gly Thr Val Met Asp Ile
    3070            3075            3080 ata tcg aga aga gac caa aga ggt agt gga caa gtt ggc acc tat    9390
Ile Ser Arg Arg Asp Gln Arg Gly Ser Gly Gln Val Gly Thr Tyr
    3085            3090            3095 gga ctc aat act ttc acc aat atg gaa gcc caa cta atc aga cag    9435
Gly Leu Asn Thr Phe Thr Asn Met Glu Ala Gln Leu Ile Arg Gln
    3100            3105            3110 atg gag gga gaa gga gtc ttt aaa agc att cag cac cta aca atc    9480
Met Glu Gly Glu Gly Val Phe Lys Ser Ile Gln His Leu Thr Ile
    3115            3120            3125 aca gaa gaa atc gct gtg caa aac tgg tta gca aga gtg ggg cgc    9525
Thr Glu Glu Ile Ala Val Gln Asn Trp Leu Ala Arg Val Gly Arg
    3130            3135            3140 gaa agg tta tca aga atg gcc atc agt gga gat gat tgt gtt gtg    9570
Glu Arg Leu Ser Arg Met Ala Ile Ser Gly Asp Asp Cys Val Val
    3145            3150            3155 aaa cct tta gat gac agg ttc gca agc gct tta aca gct cta aat    9615
Lys Pro Leu Asp Asp Arg Phe Ala Ser Ala Leu Thr Ala Leu Asn
    3160            3165            3170
```

| | | | | | | | | | | | |
|---|---|---|---|---|---|---|---|---|---|---|---|
| gac<br>Asp<br>3175 | atg<br>Met | gga<br>Gly | aag<br>Lys | att<br>Ile<br>3180 | agg<br>Arg | aaa<br>Lys | gac<br>Asp | ata<br>Ile<br>3185 | caa<br>Gln | caa<br>Gln | tgg<br>Trp | gaa<br>Glu | cct<br>Pro | tca<br>Ser | 9660 |

```
aga gga tgg aat gat tgg aca caa gtg ccc ttc tgt tca cac cat      9705
Arg Gly Trp Asn Asp Trp Thr Gln Val Pro Phe Cys Ser His His
    3190            3195                3200 ttc cat gag tta atc atg aaa gac ggt cgc gta ctc gtt gtt cca      9750
Phe His Glu Leu Ile Met Lys Asp Gly Arg Val Leu Val Val Pro
    3205            3210                3215 tgt aga aac caa gat gaa ctg att ggc aga gcc cga atc tcc caa      9795
Cys Arg Asn Gln Asp Glu Leu Ile Gly Arg Ala Arg Ile Ser Gln
    3220            3225                3230 gga gca ggg tgg tct ttg cgg gag acg gcc tgt ttg ggg aag tct      9840
Gly Ala Gly Trp Ser Leu Arg Glu Thr Ala Cys Leu Gly Lys Ser
    3235            3240                3245 tac gcc caa atg tgg agc ttg atg tac ttc cac aga cgc gac ctc      9885
Tyr Ala Gln Met Trp Ser Leu Met Tyr Phe His Arg Arg Asp Leu
    3250            3255                3260 agg ctg gcg gca aat gct att tgc tcg gca gta cca tca cat tgg      9930
Arg Leu Ala Ala Asn Ala Ile Cys Ser Ala Val Pro Ser His Trp
    3265            3270                3275 gtt cca aca agt cga aca acc tgg tcc ata cat gct aaa cat gaa      9975
Val Pro Thr Ser Arg Thr Thr Trp Ser Ile His Ala Lys His Glu
    3280            3285                3290 tgg atg aca acg gaa gac atg ctg aca gtc tgg aac agg gtg tgg     10020
Trp Met Thr Thr Glu Asp Met Leu Thr Val Trp Asn Arg Val Trp
    3295            3300                3305 att caa gaa aac cca tgg atg gaa gac aaa act cca gtg gaa aca     10065
Ile Gln Glu Asn Pro Trp Met Glu Asp Lys Thr Pro Val Glu Thr
    3310            3315                3320 tgg gag gaa atc cca tac ttg ggg aaa aga gaa gac caa tgg tgc     10110
Trp Glu Glu Ile Pro Tyr Leu Gly Lys Arg Glu Asp Gln Trp Cys
    3325            3330                3335 ggc tca ttg att ggg tta aca agc agg gcc acc tgg gca aag aac     10155
Gly Ser Leu Ile Gly Leu Thr Ser Arg Ala Thr Trp Ala Lys Asn
    3340            3345                3350 atc caa gca gca ata aat caa gtt aga tcc ctt ata ggc aat gaa     10200
Ile Gln Ala Ala Ile Asn Gln Val Arg Ser Leu Ile Gly Asn Glu
    3355            3360                3365 gaa tac aca gat tac atg cca tcc atg aaa aga ttc aga aga gaa     10245
Glu Tyr Thr Asp Tyr Met Pro Ser Met Lys Arg Phe Arg Arg Glu
    3370            3375                3380 gag gaa gaa gca gga gtt ctg tgg tag aaagcaaaac taacatgaaa       10292
Glu Glu Glu Ala Gly Val Leu Trp
    3385            3390 caaggctaga agtcaggtcg gattaagcca tagtacggaa aaaactatgc tacctgtgag  10352
ccccgtccaa ggacgttaaa agaagtcagg ccatcataaa tgccatagct tgagtaaact  10412
atgcagcctg tagctccacc tgagaaggtg taaaaaatcc gggaggccac aaaccatgga  10472
agctgtacgc atgcgtagt ggactagcgg ttaggggaga cccctccctt acaaatcgca   10532
gcaacaatgg gggcccaagg cgagatgaag ctgtagtctc gctggaagga ctagaggtta  10592
gaggagaccc ccccgaaaca aaaaacagca tattgacgct gggaaagacc agagatcctg  10652
ctgtctcctc agcatcattc caggcacaga acgccagaaa atggaatggt gctgttgaat  10712
caacaggttc t                                                     10723
```

<210> SEQ ID NO 2
<211> LENGTH: 3391
<212> TYPE: PRT

<213> ORGANISM: Dengue virus

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Arg Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
```

```
                405                 410                 415
Tyr Thr Ile Val Ile Thr Pro His Ser Gly Glu Glu His Ala Val Gly
                    420                 425                 430

Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Glu Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
        610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
        690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830
```

-continued

Arg Ser Val Thr Arg Leu Glu Asn Leu Met Trp Lys Gln Ile Thr Pro
    835                 840                 845

Glu Leu Asn His Ile Leu Ser Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Thr Asn Ile Trp Leu
930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
            965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
            995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Asp Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Lys Glu Leu Met Met Thr Thr Ile
    1220                1225                1230

Gly Ile Val Leu Leu Ser Gln Ser Thr Ile Pro Glu Thr Ile Leu
    1235                1240                1245

```
Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320

Thr Ile Lys Gly Leu Asn Pro Thr Ala Ile Phe Leu Thr Thr Leu
    1325                1330                1335

Ser Arg Thr Ser Lys Lys Arg Ser Trp Pro Leu Asn Glu Ala Ile
    1340                1345                1350

Met Ala Val Gly Met Val Ser Ile Leu Ala Ser Ser Leu Leu Lys
    1355                1360                1365

Asn Asp Ile Pro Met Thr Gly Pro Leu Val Ala Gly Gly Leu Leu
    1370                1375                1380

Thr Val Cys Tyr Val Leu Thr Gly Arg Ser Ala Asp Leu Glu Leu
    1385                1390                1395

Glu Arg Ala Ala Asp Val Lys Trp Glu Asp Gln Ala Glu Ile Ser
    1400                1405                1410

Gly Ser Ser Pro Ile Leu Ser Ile Thr Ile Ser Glu Asp Gly Ser
    1415                1420                1425

Met Ser Ile Lys Asn Glu Glu Glu Gln Thr Leu Thr Ile Leu
    1430                1435                1440

Ile Arg Thr Gly Leu Leu Val Ile Ser Gly Leu Phe Pro Val Ser
    1445                1450                1455

Ile Pro Ile Thr Ala Ala Ala Trp Tyr Leu Trp Glu Val Lys Lys
    1460                1465                1470

Gln Arg Ala Gly Val Leu Trp Asp Val Pro Ser Pro Pro Pro Met
    1475                1480                1485

Gly Lys Ala Glu Leu Glu Asp Gly Ala Tyr Arg Ile Lys Gln Lys
    1490                1495                1500

Gly Ile Leu Gly Tyr Ser Gln Ile Gly Ala Gly Val Tyr Lys Glu
    1505                1510                1515

Gly Thr Phe His Thr Met Trp His Val Thr Arg Gly Ala Val Leu
    1520                1525                1530

Met His Lys Gly Lys Arg Ile Glu Pro Thr Trp Ala Asp Val Lys
    1535                1540                1545

Lys Asp Leu Ile Ser Tyr Gly Gly Gly Trp Lys Leu Glu Gly Glu
    1550                1555                1560

Trp Lys Glu Gly Glu Glu Val Gln Val Leu Ala Leu Glu Pro Gly
    1565                1570                1575

Lys Asn Pro Arg Ala Val Gln Thr Lys Pro Gly Leu Phe Lys Thr
    1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
```

|     |     |     |     |     |     |     |     |     |     |
| --- | --- | --- | --- | --- | --- | --- | --- | --- | --- |
|     | 1640 |     |     |     | 1645 |     |     |     | 1650 |

Glu Asp His Ile Phe Arg Lys Arg Leu Thr Ile Met Asp Leu
     1655                          1660                         1665

His Pro Gly Ala Gly Lys Thr Lys Arg Tyr Leu Pro Ala Ile Val
     1670                         1675                        1680

Arg Glu Ala Ile Lys Arg Gly Leu Arg Thr Leu Ile Leu Ala Pro
     1685                         1690                        1695

Thr Arg Val Val Ala Ala Glu Met Glu Glu Ala Leu Arg Gly Leu
     1700                         1705                        1710

Pro Ile Arg Tyr Gln Thr Pro Ala Ile Arg Ala Glu His Thr Gly
     1715                         1720                        1725

Arg Glu Ile Val Asp Leu Met Cys His Ala Thr Phe Thr Met Arg
     1730                         1735                        1740

Leu Leu Ser Pro Val Arg Val Pro Asn Tyr Asn Leu Ile Ile Met
     1745                         1750                        1755

Asp Glu Ala His Phe Thr Asp Pro Ala Ser Ile Ala Ala Arg Gly
     1760                         1765                        1770

Tyr Ile Ser Thr Arg Val Glu Met Gly Glu Ala Ala Gly Ile Phe
     1775                         1780                        1785

Met Thr Ala Thr Pro Pro Gly Ser Arg Asp Pro Phe Pro Gln Ser
     1790                         1795                        1800

Asn Ala Pro Ile Ile Asp Glu Glu Arg Glu Ile Pro Glu Arg Ser
     1805                         1810                        1815

Trp Asn Ser Gly His Glu Trp Val Thr Asp Phe Lys Gly Lys Thr
     1820                         1825                        1830

Val Trp Phe Val Pro Ser Ile Lys Ala Gly Asn Asp Ile Ala Ala
     1835                         1840                        1845

Cys Leu Arg Lys Asn Gly Lys Lys Val Ile Gln Leu Ser Arg Lys
     1850                         1855                        1860

Thr Phe Asp Ser Glu Tyr Val Lys Thr Arg Thr Asn Asp Trp Asp
     1865                         1870                        1875

Phe Val Val Thr Thr Asp Ile Ser Glu Met Gly Ala Asn Phe Lys
     1880                         1885                        1890

Ala Glu Arg Val Ile Asp Pro Arg Arg Cys Met Lys Pro Val Ile
     1895                         1900                        1905

Leu Thr Asp Gly Glu Glu Arg Val Ile Leu Ala Gly Pro Met Pro
     1910                         1915                        1920

Val Thr His Ser Ser Ala Ala Gln Arg Arg Gly Arg Ile Gly Arg
     1925                         1930                        1935

Asn Pro Lys Asn Glu Asn Asp Gln Tyr Ile Tyr Met Gly Glu Pro
     1940                         1945                        1950

Leu Glu Asn Asp Glu Asp Cys Ala His Trp Lys Glu Ala Lys Met
     1955                         1960                        1965

Leu Leu Asp Asn Ile Asn Thr Pro Glu Gly Ile Ile Pro Ser Met
     1970                         1975                        1980

Phe Glu Pro Glu Arg Glu Lys Val Asp Ala Ile Asp Gly Glu Tyr
     1985                         1990                        1995

Arg Leu Arg Gly Glu Ala Arg Lys Thr Phe Val Asp Leu Met Arg
     2000                         2005                        2010

Arg Gly Asp Leu Pro Val Trp Leu Ala Tyr Arg Val Ala Ala Glu
     2015                         2020                        2025

Gly Ile Asn Tyr Ala Asp Arg Arg Trp Cys Phe Asp Gly Val Lys
     2030                         2035                        2040

-continued

```
Asn Asn Gln Ile Leu Glu Glu Asn Val Glu Val Glu Ile Trp Thr
2045                2050                2055
Lys Glu Gly Glu Arg Lys Lys Leu Lys Pro Arg Trp Leu Asp Ala
2060                2065                2070
Arg Ile Tyr Ser Asp Pro Leu Ala Leu Lys Glu Phe Lys Glu Phe
2075                2080                2085
Ala Ala Gly Arg Lys Ser Leu Thr Leu Asn Leu Ile Thr Glu Met
2090                2095                2100
Gly Arg Leu Pro Thr Phe Met Thr Gln Lys Ala Arg Asp Ala Leu
2105                2110                2115
Asp Asn Leu Ala Val Leu His Thr Ala Glu Ala Gly Gly Arg Ala
2120                2125                2130
Tyr Asn His Ala Leu Ser Glu Leu Pro Glu Thr Leu Glu Thr Leu
2135                2140                2145
Leu Leu Leu Thr Leu Leu Ala Thr Val Thr Gly Gly Ile Phe Leu
2150                2155                2160
Phe Leu Met Ser Ala Arg Gly Ile Gly Lys Met Thr Leu Gly Met
2165                2170                2175
Cys Cys Ile Ile Thr Ala Ser Ile Leu Leu Trp Tyr Ala Gln Ile
2180                2185                2190
Gln Pro His Trp Ile Ala Ala Ser Ile Ile Leu Glu Phe Phe Leu
2195                2200                2205
Ile Val Leu Leu Ile Pro Glu Pro Glu Lys Gln Arg Thr Pro Gln
2210                2215                2220
Asp Asn Gln Leu Thr Tyr Val Val Ile Ala Ile Leu Thr Val Val
2225                2230                2235
Ala Ala Thr Met Ala Asn Glu Met Gly Phe Leu Glu Lys Thr Lys
2240                2245                2250
Lys Asp Leu Gly Leu Gly Ser Ile Ala Thr Gln Gln Pro Glu Ser
2255                2260                2265
Asn Ile Leu Asp Ile Asp Leu Arg Pro Ala Ser Ala Trp Thr Leu
2270                2275                2280
Tyr Ala Val Ala Thr Thr Phe Val Thr Pro Met Leu Arg His Ser
2285                2290                2295
Ile Glu Asn Ser Ser Val Asn Val Ser Leu Thr Ala Ile Ala Asn
2300                2305                2310
Gln Ala Thr Val Leu Met Gly Leu Gly Lys Gly Trp Pro Leu Ser
2315                2320                2325
Lys Met Asp Ile Gly Val Pro Leu Leu Ala Ile Gly Cys Tyr Ser
2330                2335                2340
Gln Val Asn Pro Ile Thr Leu Thr Ala Ala Leu Phe Leu Leu Val
2345                2350                2355
Ala His Tyr Ala Ile Ile Gly Pro Gly Leu Gln Ala Lys Ala Thr
2360                2365                2370
Arg Glu Ala Gln Lys Arg Ala Ala Ala Gly Ile Met Lys Asn Pro
2375                2380                2385
Thr Val Asp Gly Ile Thr Val Ile Asp Leu Asp Pro Ile Pro Tyr
2390                2395                2400
Asp Pro Lys Phe Glu Lys Gln Leu Gly Gln Val Met Leu Leu Val
2405                2410                2415
Leu Cys Val Thr Gln Val Leu Met Met Arg Thr Thr Trp Ala Leu
2420                2425                2430
Cys Glu Ala Leu Thr Leu Ala Thr Gly Pro Ile Ser Thr Leu Trp
2435                2440                2445
```

```
Glu Gly Asn Pro Gly Arg Phe Trp Asn Thr Thr Ile Ala Val Ser
    2450            2455                2460
Met Ala Asn Ile Phe Arg Gly Ser Tyr Leu Ala Gly Ala Gly Leu
    2465            2470                2475
Leu Phe Ser Ile Met Lys Asn Thr Thr Asn Thr Arg Arg Gly Thr
    2480            2485                2490
Gly Asn Ile Gly Glu Thr Leu Gly Glu Lys Trp Lys Ser Arg Leu
    2495            2500                2505
Asn Ala Leu Gly Lys Ser Glu Phe Gln Ile Tyr Lys Lys Ser Gly
    2510            2515                2520
Ile Gln Glu Val Asp Arg Thr Leu Ala Lys Glu Gly Ile Lys Arg
    2525            2530                2535
Gly Glu Thr Asp His His Ala Val Ser Arg Gly Ser Ala Lys Leu
    2540            2545                2550
Arg Trp Phe Val Glu Arg Asn Met Val Thr Pro Glu Gly Lys Val
    2555            2560                2565
Val Asp Leu Gly Cys Gly Arg Gly Gly Trp Ser Tyr Tyr Cys Gly
    2570            2575                2580
Gly Leu Lys Asn Val Arg Glu Val Lys Gly Leu Thr Lys Gly Gly
    2585            2590                2595
Pro Gly His Glu Glu Pro Ile Pro Met Ser Thr Tyr Gly Trp Asn
    2600            2605                2610
Leu Val Arg Leu Gln Ser Gly Val Asp Val Phe Phe Ile Pro Pro
    2615            2620                2625
Glu Lys Cys Asp Thr Leu Leu Cys Asp Ile Gly Glu Ser Ser Pro
    2630            2635                2640
Asn Pro Thr Val Glu Ala Gly Arg Thr Leu Arg Val Leu Asn Leu
    2645            2650                2655
Val Glu Asn Trp Leu Asn Asn Asn Thr Gln Phe Cys Ile Lys Val
    2660            2665                2670
Leu Asn Pro Tyr Met Pro Ser Val Ile Glu Lys Met Glu Ala Leu
    2675            2680                2685
Gln Arg Lys Tyr Gly Gly Ala Leu Val Arg Asn Pro Leu Ser Arg
    2690            2695                2700
Asn Ser Thr His Glu Met Tyr Trp Val Ser Asn Ala Ser Gly Asn
    2705            2710                2715
Ile Val Ser Ser Val Asn Met Ile Ser Arg Met Leu Ile Asn Arg
    2720            2725                2730
Phe Thr Met Arg Tyr Lys Lys Ala Thr Tyr Glu Pro Asp Val Asp
    2735            2740                2745
Leu Gly Ser Gly Thr Arg Asn Ile Gly Ile Glu Ser Glu Ile Pro
    2750            2755                2760
Asn Leu Asp Ile Ile Gly Lys Arg Ile Glu Lys Ile Lys Gln Glu
    2765            2770                2775
His Glu Thr Ser Trp His Tyr Asp Gln Asp His Pro Tyr Lys Thr
    2780            2785                2790
Trp Ala Tyr His Gly Ser Tyr Glu Thr Lys Gln Thr Gly Ser Ala
    2795            2800                2805
Ser Ser Met Val Asn Gly Val Val Arg Leu Leu Thr Lys Pro Trp
    2810            2815                2820
Asp Val Val Pro Met Val Thr Gln Met Ala Met Thr Asp Thr Thr
    2825            2830                2835
Pro Phe Gly Gln Gln Arg Val Phe Lys Glu Lys Val Asp Thr Arg
```

```
                 2840              2845                   2850

Thr Gln Glu Pro Lys Glu Gly Thr Lys Lys Leu Met Lys Ile Thr
        2855                2860                   2865

Ala Glu Trp Leu Trp Lys Glu Leu Gly Lys Lys Lys Thr Pro Arg
        2870                2875                   2880

Met Cys Thr Arg Glu Glu Phe Thr Arg Lys Val Arg Ser Asn Ala
        2885                2890                   2895

Ala Leu Gly Ala Ile Phe Thr Asp Glu Asn Lys Trp Lys Ser Ala
        2900                2905                   2910

Arg Glu Ala Val Glu Asp Ser Arg Phe Trp Glu Leu Val Asp Lys
        2915                2920                   2925

Glu Arg Asn Leu His Leu Glu Gly Lys Cys Glu Thr Cys Val Tyr
        2930                2935                   2940

Asn Met Met Gly Lys Arg Glu Lys Lys Leu Gly Glu Phe Gly Lys
        2945                2950                   2955

Ala Lys Gly Ser Arg Ala Ile Trp Tyr Met Trp Leu Gly Ala Arg
        2960                2965                   2970

Phe Leu Glu Phe Glu Ala Leu Gly Phe Leu Asn Glu Asp His Trp
        2975                2980                   2985

Phe Ser Arg Glu Asn Ser Leu Ser Gly Val Glu Gly Glu Gly Leu
        2990                2995                   3000

His Lys Leu Gly Tyr Ile Leu Arg Asp Val Ser Lys Lys Glu Gly
        3005                3010                   3015

Gly Ala Met Tyr Ala Asp Asp Thr Ala Gly Trp Asp Thr Lys Ile
        3020                3025                   3030

Thr Leu Glu Asp Leu Lys Asn Glu Glu Met Val Thr Asn His Met
        3035                3040                   3045

Glu Gly Glu His Lys Lys Leu Ala Glu Ala Ile Phe Lys Leu Thr
        3050                3055                   3060

Tyr Gln Asn Lys Val Val Arg Val Gln Arg Pro Thr Pro Arg Gly
        3065                3070                   3075

Thr Val Met Asp Ile Ile Ser Arg Arg Asp Gln Arg Gly Ser Gly
        3080                3085                   3090

Gln Val Gly Thr Tyr Gly Leu Asn Thr Phe Thr Asn Met Glu Ala
        3095                3100                   3105

Gln Leu Ile Arg Gln Met Glu Gly Glu Gly Val Phe Lys Ser Ile
        3110                3115                   3120

Gln His Leu Thr Ile Thr Glu Glu Ile Ala Val Gln Asn Trp Leu
        3125                3130                   3135

Ala Arg Val Gly Arg Glu Arg Leu Ser Arg Met Ala Ile Ser Gly
        3140                3145                   3150

Asp Asp Cys Val Val Lys Pro Leu Asp Asp Arg Phe Ala Ser Ala
        3155                3160                   3165

Leu Thr Ala Leu Asn Asp Met Gly Lys Ile Arg Lys Asp Ile Gln
        3170                3175                   3180

Gln Trp Glu Pro Ser Arg Gly Trp Asn Asp Trp Thr Gln Val Pro
        3185                3190                   3195

Phe Cys Ser His His Phe His Glu Leu Ile Met Lys Asp Gly Arg
        3200                3205                   3210

Val Leu Val Val Pro Cys Arg Asn Gln Asp Glu Leu Ile Gly Arg
        3215                3220                   3225

Ala Arg Ile Ser Gln Gly Ala Gly Trp Ser Leu Arg Glu Thr Ala
        3230                3235                   3240
```

```
Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Thr Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390

<210> SEQ ID NO 3
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: Wild-type DEN2 strain 16681

<400> SEQUENCE: 3
agttgttagt ctacgtggac cgacaaagac agattctttg agggagctaa gctcaacgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggatggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
```

```
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaagaacat ggaaggaaaa     1320
gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca caatgagtg ctctccaaga     1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttttgag ataatggatt tggaaaaaag acatgtctta   1980
ggtcgcctga ttacagtcaa cccaattgtg acagaaaaag atagcccagt caacatagaa    2040
gcagaacctc cattcggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttggagtca tggtgcaggc cgatagtggt tgcgttgtga ctggaaaaa caaagaactg    2460
aaaatgtggc gtgggattt catcacagac aacgtgcaca catggacaga acaatacaag    2520
ttccaaccag aatcccct tc aaaactagct tcagctatcc agaaagccca tgaagagggc    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca tgacacatg gaagatagag    3060
aaagcctctt tcattgaagt taaaaactgc cactggccaa atcacacac cctctgagc    3120
aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
```

```
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctattttcct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga gatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaagggat tcttggatat   4620
tcccagatcg gagccggagt ttacaaagaa ggaacattcc atacaatgtg gcatgtcaca   4680
cgtggcgctg ttctaatgca taaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag atcgaagga tgcatttttc gaaagagaa gactgaccat catggaccte   5100
cacccaggag cggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag acccccagcc tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggatttt   5460
atgacagcca ctccccgggg aagcagagac ccatttcctc agagcaatgc accaatcata   5520
gatgaagaaa gagaaatccc tgaacgttcg tggaattccg acatgaatgg gtcacggat   5580
tttaagggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
```

```
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgga    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg gaagcattg caaccagca acccgagagc    6900 aacatcctgg acatagatct acgtcctgca tcagcatgga cgctgtatgc cgtggccaca    6960
acatttgtta caccaatgtt gagacatagc attgaaaatt cctcagtgaa tgtgtccta    7020 acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg    7380
actacatggg ctctgtgtga ggctttaacc ttagctaccg ggcccatctc acattgtgg    7440 gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa agccgattg    7620 aacgcattgg gaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
```

```
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt cgtcoccatg    8580 gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacatg gaaccttca    9660 agaggatgga atgattggac acaagtgccc ttctgttcac accatttcca tgagttaatc    9720
atgaaagacg tcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca    10080
tacttgggga aaagagaaga ccaatggtgc ggctcattga ttgggttaac aagcagggcc    10140
acctgggcaa agaacatcca agcagcaata aatcaagtta tcccttat aggcaatgaa    10200 gaatacacag attcatgcc atccatgaaa agattcagaa gagaagagga agaagcagga    10260
gttctgtggt agaaagcaaa actaacatga acaaggcta gagtcaggt cggattaagc    10320 catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gaccoctccc ttacaaatcg cagcaacaat gggggcccaa ggcgagatga    10560
agctgtagtc tcgctggaag gactagaggt tagaggagac ccccccgaaa caaaaaacag    10620
catattgacg ctgggaaaga ccagagatcc tgctgtctcc tcagcatcat tccaggcaca    10680
gaacgccaga aaatggaatg gtgctgttga atcaacaggt tct                      10723
```

```
<210> SEQ ID NO 4
<211> LENGTH: 37
<212> TYPE: DNA
<213> ORGANISM: Artificial sequence
<220> FEATURE:
<223> OTHER INFORMATION: primer

<400> SEQUENCE: 4
gttttcccag tcacgacacg tggaccgaca aagacag                                37

<210> SEQ ID NO 5
<211> LENGTH: 36
<212> TYPE: DNA
<213> ORGANISM: Artificial sequence
<220> FEATURE:
<223> OTHER INFORMATION: primer

<400> SEQUENCE: 5
aacagctatg accatgttcc tcctgaaacc ccttcc                                 36

<210> SEQ ID NO 6
<211> LENGTH: 36
<212> TYPE: DNA
<213> ORGANISM: Artificial sequence
<220> FEATURE:
<223> OTHER INFORMATION: primer

<400> SEQUENCE: 6
gttttcccag tcacgacatc acgtacaagt gtcccc                                 36

<210> SEQ ID NO 7
<211> LENGTH: 37
<212> TYPE: DNA
<213> ORGANISM: Artificial sequence
<220> FEATURE:
<223> OTHER INFORMATION: primer

<400> SEQUENCE: 7
aacagctatg accatgagca acaccatctc attgaag                                37

<210> SEQ ID NO 8
<211> LENGTH: 42
<212> TYPE: DNA
<213> ORGANISM: Artificial
<220> FEATURE:
<223> OTHER INFORMATION: primer

<400> SEQUENCE: 8
gttttcccag tcacgactgc aaccagaaaa cttggaatac ac                          42

<210> SEQ ID NO 9
<211> LENGTH: 39
<212> TYPE: DNA
<213> ORGANISM: Artificial sequence
<220> FEATURE:
<223> OTHER INFORMATION: primer

<400> SEQUENCE: 9
aacagctatg accatggctc catagattgc tccaaagac                              39

<210> SEQ ID NO 10
<211> LENGTH: 41
<212> TYPE: DNA
<213> ORGANISM: Artificial sequence
<220> FEATURE:
<223> OTHER INFORMATION: primer
```

-continued

<400> SEQUENCE: 10
gttttcccag tcacgacccc agtcaacata gaagcagaac c            41

<210> SEQ ID NO 11
<211> LENGTH: 40
<212> TYPE: DNA
<213> ORGANISM: Artificial sequence
<220> FEATURE:
<223> OTHER INFORMATION: primer

<400> SEQUENCE: 11
aacagctatg accatgccaa agccatagtc ttcaacttcc             40

<210> SEQ ID NO 12
<211> LENGTH: 36
<212> TYPE: DNA
<213> ORGANISM: Artificial sequence
<220> FEATURE:
<223> OTHER INFORMATION: primer

<400> SEQUENCE: 12
gttttcccag tcacgacatc atgcaggcag gaaaac                 36

<210> SEQ ID NO 13
<211> LENGTH: 37
<212> TYPE: DNA
<213> ORGANISM: Artificial sequence
<220> FEATURE:
<223> OTHER INFORMATION: primer

<400> SEQUENCE: 13
aacagctatg accatgacca taaccatcac tcttccc                37

<210> SEQ ID NO 14
<211> LENGTH: 37
<212> TYPE: DNA
<213> ORGANISM: Artificial sequence
<220> FEATURE:
<223> OTHER INFORMATION: primer

<400> SEQUENCE: 14
aacagctatg accatgacca taaccatcac tcttccc                37

<210> SEQ ID NO 15
<211> LENGTH: 36
<212> TYPE: DNA
<213> ORGANISM: Artificial sequence
<220> FEATURE:
<223> OTHER INFORMATION: primer

<400> SEQUENCE: 15
aacagctatg accatggctc tctccagttc caaatc                 36

<210> SEQ ID NO 16
<211> LENGTH: 38
<212> TYPE: DNA
<213> ORGANISM: Artificial sequence
<220> FEATURE:
<223> OTHER INFORMATION: priemr

<400> SEQUENCE: 16
gttttcccag tcacgacaag aaccagcaag aaaaggag               38

<210> SEQ ID NO 17
<211> LENGTH: 38
<212> TYPE: DNA

```
<213> ORGANISM: Artificial sequence
<220> FEATURE:
<223> OTHER INFORMATION: primer

<400> SEQUENCE: 17
aacagctatg accatgcacc attaccataa agacccac                              38

<210> SEQ ID NO 18
<211> LENGTH: 37
<212> TYPE: DNA
<213> ORGANISM: Artificial sequence
<220> FEATURE:
<223> OTHER INFORMATION: primer

<400> SEQUENCE: 18
gttttcccag tcacgacttg aaccatcatg ggcggac                               37

<210> SEQ ID NO 19
<211> LENGTH: 41
<212> TYPE: DNA
<213> ORGANISM: Artificial sequence
<220> FEATURE:
<223> OTHER INFORMATION: primer

<400> SEQUENCE: 19
aacagctatg accatgtcct gcttttatac ttggaacgaa c                          41

<210> SEQ ID NO 20
<211> LENGTH: 36
<212> TYPE: DNA
<213> ORGANISM: Artificial sequence
<220> FEATURE:
<223> OTHER INFORMATION: primer

<400> SEQUENCE: 20
gttttcccag tcacgacaag cccatttcac agaccc                                36

<210> SEQ ID NO 21
<211> LENGTH: 38
<212> TYPE: DNA
<213> ORGANISM: Artificial sequence
<220> FEATURE:
<223> OTHER INFORMATION: primer

<400> SEQUENCE: 21
aacagctatg accatgtcaa tttcttcctt tccccttc                              38

<210> SEQ ID NO 22
<211> LENGTH: 38
<212> TYPE: DNA
<213> ORGANISM: Artificial sequence
<220> FEATURE:
<223> OTHER INFORMATION: primer

<400> SEQUENCE: 22
gttttcccag tcacgacgag aggagaagca aggaaaac                              38

<210> SEQ ID NO 23
<211> LENGTH: 35
<212> TYPE: DNA
<213> ORGANISM: Artificial sequence
<220> FEATURE:
<223> OTHER INFORMATION: primer

<400> SEQUENCE: 23
aacagctatg accatgaggg acacattcac tgagg                                 35
```

<210> SEQ ID NO 24
<211> LENGTH: 36
<212> TYPE: DNA
<213> ORGANISM: Artificial sequence
<220> FEATURE:
<223> OTHER INFORMATION: primer

<400> SEQUENCE: 24
gttttcccag tcacgacaca gagaacaccc caagac         36

<210> SEQ ID NO 25
<211> LENGTH: 35
<212> TYPE: DNA
<213> ORGANISM: Artificial sequence
<220> FEATURE:
<223> OTHER INFORMATION: primer

<400> SEQUENCE: 25
aacagctatg accatgtcca cttcctggat tccac          35

<210> SEQ ID NO 26
<211> LENGTH: 39
<212> TYPE: DNA
<213> ORGANISM: Artificial sequence
<220> FEATURE:
<223> OTHER INFORMATION: primer

<400> SEQUENCE: 26
gttttcccag tcacgacaca agtaatgctc ctagtcctc      39

<210> SEQ ID NO 27
<211> LENGTH: 38
<212> TYPE: DNA
<213> ORGANISM: Artificial sequence
<220> FEATURE:
<223> OTHER INFORMATION: primer

<400> SEQUENCE: 27
aacagctatg accatgttca ctgatgacac tatgttcc       38

<210> SEQ ID NO 28
<211> LENGTH: 37
<212> TYPE: DNA
<213> ORGANISM: Artificial sequence
<220> FEATURE:
<223> OTHER INFORMATION: primer

<400> SEQUENCE: 28
gttttcccag tcacgacgtc atcaccaaat cccacag        37

<210> SEQ ID NO 29
<211> LENGTH: 39
<212> TYPE: DNA
<213> ORGANISM: Artificial sequence
<220> FEATURE:
<223> OTHER INFORMATION: priemr

<400> SEQUENCE: 29
aacagctatg accatggctt cttctctctt tttcccatc      39

<210> SEQ ID NO 30
<211> LENGTH: 36
<212> TYPE: DNA
<213> ORGANISM: Artificial sequence
<220> FEATURE:
<223> OTHER INFORMATION: primer

```
<400> SEQUENCE: 30
gttttcccag tcacgacaag gtgagaagca atgcag                              36

<210> SEQ ID NO 31
<211> LENGTH: 37
<212> TYPE: DNA
<213> ORGANISM: Artificial sequence
<220> FEATURE:
<223> OTHER INFORMATION: primer

<400> SEQUENCE: 31
aacagctatg accatgtgga atggtgtga acagaag                              37

<210> SEQ ID NO 32
<211> LENGTH: 39
<212> TYPE: DNA
<213> ORGANISM: Artificial sequence
<220> FEATURE:
<223> OTHER INFORMATION: primer

<400> SEQUENCE: 32
gttttcccag tcacgacgca ttcagcacct aacaatcac                           39

<210> SEQ ID NO 33
<211> LENGTH: 35
<212> TYPE: DNA
<213> ORGANISM: Artificial sequence
<220> FEATURE:
<223> OTHER INFORMATION: primer

<400> SEQUENCE: 33
aacagctatg accatgggca tttatgatgg cctga                               35

<210> SEQ ID NO 34
<211> LENGTH: 17
<212> TYPE: DNA
<213> ORGANISM: Artificial sequence
<220> FEATURE:
<223> OTHER INFORMATION: primer

<400> SEQUENCE: 34
ccatggaagc tgtacgc                                                   17

<210> SEQ ID NO 35
<211> LENGTH: 36
<212> TYPE: DNA
<213> ORGANISM: Artificial sequence
<220> FEATURE:
<223> OTHER INFORMATION: primer

<400> SEQUENCE: 35
aacagctatg accatgtgat tcaacagcac cattcc                              36

<210> SEQ ID NO 36
<211> LENGTH: 17
<212> TYPE: DNA
<213> ORGANISM: Artificial sequence
<220> FEATURE:
<223> OTHER INFORMATION: primer tail

<400> SEQUENCE: 36
gttttcccag tcacgac                                                   17

<210> SEQ ID NO 37
<211> LENGTH: 16
<212> TYPE: DNA
```

```
<213> ORGANISM: Artificial sequence
<220> FEATURE:
<223> OTHER INFORMATION: primer tail

<400> SEQUENCE: 37
aacagctatg accatg                                                    16

<210> SEQ ID NO 38
<211> LENGTH: 10723
<212> TYPE: DNA
<213> ORGANISM: Dengue virus
<220> FEATURE:
<221> NAME/KEY: misc_feature
<222> LOCATION: (1)..(10723)
<223> OTHER INFORMATION: LAV2

<400> SEQUENCE: 38
agttgttagt ctacgtggac cgacaaagac agattctttg agggagctaa gctcaatgta      60
gttctaacag ttttttaatt agagagcaga tctctgatga ataaccaacg aaaaaggcg      120 aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag aaagagatt     360 ggaaggatgc tgaacatctt gaataggaga cgcagatctg caggcatgat cattatgctg     420
attccaacag tgatggcgtt ccatttaacc acgtaacg agaaccaca catgatcgtc     480 agcagacaag agaaagggaa aagtcttctg tttaaaacag aggttggcgt gaacatgtgt     540
accctcatgg ccatggacct tggtgaattg tgtgaagaca caatcacgta caagtgtccc     600
cttctcaggc agaatgagcc agaagacata gactgttggt gcaactctac gtccacgtgg     660
gtaacttatg gacgtgtac caccatggga gaacatagaa gagaaaaag atcagtggca     720 ctcgttccac atgtgggaat gggactggag acacgaactg aaacatggat gtcatcagaa     780
ggggcctgga acatgtcca gagaattgaa acttggatct tgagacatcc aggcttcacc     840
atgatggcag caatcctggc atacaccata ggaacgacac atttccaaag agccctgatt     900
ttcatcttac tgacagctgt cactccttca atgacaatgc gttgcatagg aatgtcaaat     960 agagacttg tggaagggt tcaggagga agctgggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taatgaaga gcaggacaaa    1200 aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa acctcactc aggggaagag    1380 catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atcccatgc gaagaaacag    1680 gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
```

```
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta     1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt tgagacaac aatgaggggg     2160 gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg ataggaatg     2340 aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagaggac    2580
atttgtggaa tccgctcagt aacaagactg gagaatctga tgtggaaaca ataacacca    2640 gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct cttttgagaac aacccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttggaa tggcattgtt cctggaggaa     3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caactttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aatggtgag aaatatggaa    3900 aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttcct aacaaccctc tcaagaacca gcaagaaaag gagctggcca    4140
ttaaatgagg ctatcatggc agtcgggatg gtgagcattt tagccagttc tctcctaaaa    4200
```

```
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggaccte    5100 cacccaggag cgggaaagac gaagagatac cttccggcca tagtcagaga agctataaaa    5160
cggggtttga gaacattaat cttggccccc actagagttg tggcagctga aatggaggaa    5220
gcccttagag gacttccaat aagataccag accccagcca tcagagctgw gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg acatgaatgg gtcacggat    5580 tttaaaggga agactgtttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata daccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt    6120 gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
```

```
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg gacaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atgaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt tgtccccatg    8580
gtgacacaga tggcaatgac agacacgact ccatttggac aacagcgcgt ttttaaagag    8640
aaagtggaca cgagaaccca agaaccgaaa gaaggcacga gaaactaat gaaaataaca    8700 gcagagtggc tttggaaaga attagggaag aaaaagacac ccaggatgtg caccagagaa    8760
gaattcacaa gaaaggtgag aagcaatgca gccttgggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
```

-continued tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa gaatcacact agaagaccta aaaaatgaag aaatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 39
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: VDV1

<400> SEQUENCE: 39
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300

```
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga acaaacgtt ccgtcgcatt    720
ggccccacac gtggggcttg gcctagaaac aagagccgaa acgtggatgt cctctgaagg    780
tgcttggaaa cagatacaaa agtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctgggc aatggctgtg ggctattcgg   1260
aaaaggtagt ctaataacgt gtgccaagtt taagtgtgtg acaaaactag aaggaaagat   1320
agctcaatat gaaaacctaa aatattcagt gatagtcacc gtccacactg agatcagca   1380
ccaggtggga atgagacta cagaacatgg aacaactgca accataacac ctcaagctcc   1440
tacgtcggaa atacagctga ccgactacg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattggagc   2040
agaaccaccc tttggtgaga gctacatcgt ggtaggagca ggtgaaaaag ctttgaaact   2100
aagctggttc aagaaggaa gcagcatagg gaaaatgttt gaagcaactg cccgaggagc   2160
acgaaggatg gccattctgg agacaccgc atgggacttc ggttctatag gaggagtgtt   2220
cacgtctatg gaaaactgg tacaccaggt ttttggaact gcatatggag ttttgtttag   2280
cggagtttct tggaccatga aaataggaat agggattctg ctgacatggc taggattaaa   2340
ttcaaggaac acgtccctt cggtgatgtg catcgcagtt ggcatggtca cactgtacct   2400
aggagtcatg gttcaggcag attcgggatg tgtaatcaac tggaaaggca gagaacttaa   2460
atgtggaagc ggcattttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg agagcgttag   2700
```

-continued

```
tggaatcttg gcccaaggaa aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atggggtact ggatagaaag tgaaaagaac gagacatgga agttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga    3240 actagatttc gattttttgtg aaggtaccac agttgttgtg gatgaacatt gtggaaatcg    3300
aggaccatct ctcagaacca caacagtcac aggaaagata tccatgaat ggtgctgcag    3360 atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta aacagaaaaa caaaatctgg ggaaggaaga gttggccccct    4140 caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc aatgtcaat accagcgacc cttttttgtgt ggtatttttg    4500 gcagaaaaag aaacagagat caggagtgct atgggacaca cccagccccc cagaagtgga    4560
aagagcagtt cttgatgatg gcatctatag aattttgcaa agaggactgt gggcaggtc    4620 ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag ccccctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
```

```
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggccttttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacgggaa acggtgat ccaattgagc agaaaaacct ttgacactga    5700
gtaccagaaa acaaaaaaca cgactgggaa ctatgtcgtc acaacagaca tttccgaaat    5760
gggagcaaat ttccgggccg acagggtaat agacccaagg cggtgtctga accggtaat    5820 actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcctttaa aaaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca gaaggtggtg cttcgatggg gaaaggaaca accaggtgtt    6240
ggaggagaac atggacgtgg agatctgac aaaagaagga gaaagaaaga actacgacc    6300 tcgctggttg gacgccagaa catactctga cccactggct ctgcgcgagt ttaaagagtt    6360
tgcagcagga agaagaagcg tctcaggtga cctaatatta gaaatagga acttccaca    6420 acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggta ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
cacaacaatc atcactccta tgatgagaca cacaattgaa acacaacgg caaatatttc    7020 cctgacagcc atcgcaaacc aagcagctat attgatggga cttgacaagg atgccaat    7080 atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttcttttgat    7380
gcggactaca tgggcttgt gtgaatccat cacattggct actggacctc tgaccactct    7440
ttgggaggga tctccaggaa aattctggaa caccacaata gcggtatcca tggcaaacat    7500
```

```
tttcaggggg agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaagg aggacctgga catgaggaac caatcccaat     7920
ggcgacctat ggatggaacc tagtaaggct gcactccgga aaagatgtat tttttatacc    7980
acctgagaaa tgtgacaccc ttttgtgtga tattggtgag tcctctccga acccaactat    8040
agaggaagga agaacgttac gtgttctgaa atggtggaa ccatggctca gaggaaacca     8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg gaacaggaaa cattgtgtca gcagtaaaca tgacatctag    8280
aatgttgcta atcggttca caatggctca caggaagcca acatatgaaa gagacgtgga     8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttggga caacagaggg tgtttaaaga    8640
gaaagttgac acgcgcacac caaagcaaa acgtggcaca gcacaaatta tggaagtgac     8700
agccaggtgg ttatggggtt cctttctag aaacaaaaaa cccagaattt gcacaagaga     8760
ggagtttaca agaaagtta ggtcaaacgc agctattgga gcagtgttcg ttgatgaaaa     8820
tcaatggaac tcggcaaaag aagcagtgga agacgaacgg ttctgggaac ttgtccacag    8880
agagagggag cttcataaac aggggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca acttggata     9120 catactcaga gacatatcaa ggattccagg ggggaacatg tatgcagatg acacagccgg    9180
atgggacaca gaataacag aggatgatct ccagaatgag gctaaaatca ctgacatcat     9240
ggagcccgaa catgccctgc tggctacgtc aatctttaag ctgacctacc aaaataaggt    9300
ggtaagggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatctttta cccagcgaat ggaaacccc      9480 aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
```

-continued

```
cgctatttgt tcagccgttc cagttgattg ggtcccaacc agccgcacca cctggtcgat    9960
ccatgcccat caccaatgga tgacaacaga agacatgtta tcagtatgga atagggtctg   10020
gatagaggaa aacccatgga tggaggataa gactcatgtg tccagttggg aagaagttcc   10080
ataccctagga aagagggaag atcagtggtg tggatccctg ataggcttaa cagcaagggc   10140
cacctgggcc actaatatac aagtggccat aaaccaagtg agaaggctca ttgggaatga   10200
gaattatcta gattacatga catcaatgaa gagattcaag aatgagagtg atcccgaagg   10260
ggcactctgg taagtcaaca cattcacaaa ataaggaaaa ataaaaaatc aaatgaggca   10320
agaagtcagg ccagattaag ccatagtacg gtaagagcta tgctgcctgt gagccccgtc   10380
caaggacgta aaatgaagtc aggccgaaag ccacggtttg agcaagccgt gctgcctgtg   10440
gctccatcgt ggggatgtaa aaacccggga ggctgcaacc catggaagct gtacgcatgg   10500
ggtagcagac tagtggttag aggagacccc tcccaagaca caacgcagca gcggggccca   10560
acaccagggg aagctgtacc ctggtggtaa ggactagagg ttagaggaga ccccccgcgt   10620
aacaataaac agcatattga cgctgggaga gaccagagat cctgctgtct ctacagcatc   10680
attccaggca cagaacgcca gaaaatggaa tggtgctgtt gaatcaacag gttct         10735
```

<210> SEQ ID NO 40
<211> LENGTH: 10735
<212> TYPE: DNA
<213> ORGANISM: Dengue virus
<220> FEATURE:
<221> NAME/KEY: misc_feature
<222> LOCATION: (1)..(10735)
<223> OTHER INFORMATION: LAV1/PDK13

<400> SEQUENCE: 40

```
agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgcccccg    600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
```

-continued

```
ctttgtgtgc cgacgaacgt tcgtggacag aggctggggc aatggctgtg ggctattcgg    1260
aaaaggtagt ctaataacgt gtgccaagtt taagtgtgtg acaaaactag aaggaaagat    1320
agctcaatat gaaaacctaa aatattcagt gatagtcacc gtccacactg gagatcagca    1380
ccaggtggga aatgagacta cagaacatgg aacaactgca accataacac ctcaagctcc    1440
tacgtcggaa atacagctga ccgactacgg aaccctttaca ttagattgtt cacctaggac   1500
agggctagat tttaacgaga tggtgttgct gacaatgaaa aagaaatcat ggcttgtcca    1560
caaacagtgg tttctagact taccactgcc ttggacctct ggggctttaa catcccaaga    1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc cctttttcgac ccaagatgag aaaggagcaa cccagaatgg   1980
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg gagacaccgc atgggacttc ggttctatag gaggagtgtt    2220
cacgtctatg ggaaaactgg tacaccaggt ttttggaact gcatatgag ttttgtttag     2280 cggagtttct tggaccatga aaataggaat agggattctg ctgacatggc taggattaaa    2340
ttcaaggaac acgtcccttt cggtgatgtg catcgcagtt ggcatggtca cactgtacct    2400
aggagtcatg gttcaggcag attcgggatg tgtaatcaac tggaaaggca gagaacttaa    2460
atgtggaagc ggcattttttg tcactaatga agttcacact tggacagagc aatacaaatt    2520
ccaggctgac tcccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg gagacgttag    2700
tggaatcttg gcccaaggga aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg gattttcac gacaaacata tggttgaaat tgcgtgactc     2940
ctacacccaa gtatgtgacc accggctgat gtcagctgcc attaaggaca gcaaggcagt    3000
ccatgctgac atggggtact ggatagaaag tgaaaagaac gagacatgga agttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga    3240 actagatttc gatttttgtg aaggtaccac agttgttgtg gatgaacatt gtggaaatcg    3300
aggaccatct ctcagaacca acagtcac aggaaagata atccatgaat ggtgctgcag     3360
atcttgtacg ctaccccccc tacgtttcaa agggaagac gggtgttggt acggcatgga     3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
```

```
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta taacagaaaa caaaatctgg ggaaggaaga gttggcccct    4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc caatgtcaat accagcgacc cttttgtgt ggtatttttg    4500 gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gttttcaagga tcctggaaca cgggagaaga    4800
agtacaggtg attgctgttg aaccgggaaa aaaccccaaa aatgtacaaa caacgccggg    4860
taccttcaag accctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctc cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag atcggtgga ggccttttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640 ctgttttaaga aaaacgggaa acggtgtat ccaattgagc agaaaaacct ttgacactga    5700
gtaccagaaa acaaaaaaca cgactgggaa ctatgtcgtc acaacagaca tttccgaaat    5760
gggagcaaat ttccgggccg acagggtaat agacccaagg cggtgtctga acccggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagccttaa acaatgatga ggaccacgct cattggacag aagcaaagat    6000
```

-continued

```
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca gaaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaaataggga aacttccaca    6420
acatttgacg caaagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggacccctct atgcagtggc    6960 cacaacaatc atcactccta tgatgagaca cacaattgaa aacacaacgg caaatatttc    7020
cctgacagcc atcgcaaacc aagcagctat attgatggga cttgacaagg gatggccaat    7080
atcgaagatg gacataggag ttccacttct cgccttgggg tgctattccc aagtgaatcc    7140
gctgacactg atagcggcag tattgatgct agtagctcat tacgccataa ttggacctgg    7200
actgcaagca aaagctacta gagaagctca aaaaagaaca gcggctggaa taatgaaaaa    7260
tccaactgtc gacgggattg ttgcaataga cttagatccc gtggtttacg atgcaaaatt    7320
tgaaaaacag ctaggccaaa taatgttgtt gatactttgc acatcacaga ttcttttgat    7380
gcggactaca tgggccttgt gtgaatccat cacattggct actggacctc tgaccactct    7440
ttgggaggga tctccaggaa aattctggaa caccacaata gcggtatcca tggcaaacat    7500 tttcagggg agttatctag caggagcagg tctggccttc tcattaatga aatctctagg    7560
aggaggtagg agaggcacgg gagcccaagg ggaaacactg ggagaaaaat ggaaaagaca    7620
actaaaccaa ctgagcaagt cagaattcaa tacttacaag aggagtggga ttatggaggt    7680
ggatagatcc gaagccaaag agggactgaa aagaggagaa caaccaaac acgcagtatc    7740 gagaggaacg gccaaactga ggtggttcgt ggagaggaac cttgtgaaac cagaagggaa    7800
agtcatagac ctcggttgtg gaagaggtgg ctggtcatat tattgcgctg ggctgaagaa    7860
agtcacagaa gtgaaaggat acacaaaagg aggacctgga catgaggaac caatcccaat    7920
ggcgacctat ggatggaacc tagtaaagct gcactccgga aaagatgtat tttttatacc    7980
acctgagaaa tgtgacaccc ttttgtgtga tattggtgag tcctctccga acccaactat    8040
agaggaagga gaacgttac gtgttctgaa aatggtggaa ccatggctca gaggaaacca    8100
attttgcata aaaattctaa atcctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg gaacaggaaa cattgtgtca gcagtaaaca tgacatctag    8280
aatgttgcta aatcggttca caatggctca caggaagcca acatatgaaa gagacgtgga    8340
cttaggcgct ggaacaagac atgtggcagt agaaccagag gtagccaacc tagatatcat    8400
```

-continued

```
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttggga caacagaggg tgtttaaaga    8640
gaaagttgac acgcgcacac caaaagcaaa acgtggcaca gcacaaatta tggaagtgac    8700
agccaggtgg ttatggggtt tcctttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca aacttggata    9120
catactcaga gacatatcaa ggattccagg ggggaacatg tatgcagatg acacagccgg    9180
atgggacaca agaataacag aggatgatct ccagaatgag gctaaaatca ctgacatcat    9240
ggagcccgaa catgccctgc tggctacgtc aatctttaag ctgacctacc aaaataaggt    9300
ggtaaggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatcttttta cccagcgaat ggaaaccc     9480
aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat ggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga ataggtctg   10020
gatagaggaa acccatggat ggaggataa gactcatgtg tccagttggg aagaagttcc   10080
atacctagga aagagggaag atcagtggtg tggatccctg ataggcttaa cagcaagggc   10140
cacctgggcc actaatatac aagtggccat aaaccaagtg agaaggctca ttgggaatga   10200
gaattatcta gattacatga catcaatgaa gagattcaag aatgagagtg atccccgaagg   10260
ggcactctgg taagtcaaca cattcacaaa ataaggaaaa taaaaaatc aaatgaggca   10320
agaagtcagg ccagattaag ccatagtacg gtaagagcta tgctgcctgt gagccccgtc   10380
caaggacgta aaatgaagtc aggccgaaag ccacggtttg agcaagccgt gctgcctgtg   10440
gctccatcgt ggggatgtaa aaacccggga ggctgcaacc catggaagct gtacgcatgg   10500
ggtagcagac tagtggttag aggagacccc tcccaagaca caacgcagca gcgggggccca  10560
acaccagggg aagctgtacc ctggtggtaa ggactagagg ttagaggaga ccccccgcgt   10620
aacaataaac agcatattga cgctgggaga gaccagagat cctgctgtct ctacagcatc   10680
attccaggca cagaacgcca gaaaatggaa tggtgctgtt gaatcaacag gttct         10735
```

<210> SEQ ID NO 41

<211> LENGTH: 10699
<212> TYPE: DNA
<213> ORGANISM: Dengue virus
<220> FEATURE:
<221> NAME/KEY: misc_feature
<222> LOCATION: (1)..(10699)
<223> OTHER INFORMATION: LAV3

<400> SEQUENCE: 41

```
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagct atggatctgg gagagatgtg tgatgacacg gtcacttaca aatgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca aatacaccgt catcatcaca gtgcacacag gagaccaaca   1380
ccaggtggga aatgaaacgc agggagtcac ggctgagata acaccccagg catcaaccgc   1440
tgaagccatt ttacctgaat atggaaccct cgggctagaa tgctcaccac ggacaggttt   1500
ggatttcaat gaaatgatct yattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaagggatga gctatgcaat gtgcttgggt agctttgtgt tgaagaaaga   1860
agtctccgaa acgcagcatg ggacaatact cattaaggtt gagtacaaag ggaaagatgc   1920
accctgcaag attccttttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
```

```
gtacaagaag ggaagctcga ttgggaagat gttcgaggct actgccagag gtgcaaggcg    2160
catggccatc ttgggagaca cagcctggga ctttggatca gtgggtggtg ttttgaattc    2220
attagggaaa atggtccacc aaatatttgg gagtgcttac acagccctat ttggtggagt    2280
ctcctggatg atgaaaattg gaataggtgt cctcttaacc tggatagggt tgaactcaaa    2340
aaatacttct atgtcatttt catgcatcgc gataggaatc attacactct atctgggagc    2400
cgtggtgcaa gctgacatgg ggtgtgtcat aaactgaaaa ggcaaagaac tcaaatgtgg    2460
aagtggaatt ttcgtcacta atgaggtcca cacctggaca gagcaataca aatttcaagc    2520
agactccccc aagagactgg caacagccat tgcaggcgct tgggaaaatg gagtgtgcgg    2580
aattaggtca caaccagaa tggagaacct cttgtggaag caaatagcca atgaactgaa    2640
ttacatatta tgggaaaaca acattaaatt aacggtagtt gtaggcgaca taactggggt    2700
cttagagcaa gggaaaagaa cactaacacc acaacccatg gagctaaaat attcttggaa    2760
aacatgggga aaggcaaaaa tagtgacagc tgaaacacaa aattcctctt tcataataga    2820
tgggccaagc acaccggagt gtccaagtgc ctcaagagca tggaatgtgt gggaggtgga    2880
ggattacggg ttcggagttt tcacaaccaa catatggctg aaactccgag aggtgtacac    2940
ccaactatgt gaccataggc taatgtcggc agccgtcaag gatgagaggg ctgtacatgc    3000
cgacatgggc tattggatag aaagccaaaa gaatgggagt tggaagctag aaaaagcatc    3060
cttcatagag gtgaaaacct gcacatggcc aaaatcacac actctctgga gcaatggtgt    3120
gctagagagt gacatgatta tcccaaagag tctagctggt cccatttcgc aacacaacca    3180
caggcccggg taccacaccc aaacggcagg accctggcac ttaggaaaat tggagctgga    3240
cttcaactat tgtgaaggaa caacagttgt catctcagaa actgtgggaa caagaggccc    3300
atcattgaga acaacaacgg tgtcaggaa gttgatacac gaatggtgct gccgctcgtg    3360
cacacttcct cccctacgat acatgggaga agacggctgc tggtatgcca tggaaatcag    3420
acccattaat gagaaagaag agaatatggt aaagtctcta gcctcagcag ggagtggaaa    3480
ggtggacaac ttcacaatgg gtgtcttgtg tttggcaatc ctctttgaag aggtgatgag    3540
aggaaaattt gggaaaaaac acatgattgc aggggttctc ttcacgtttg tgctcctcct    3600
ctcagggcaa ataacatgga gagacatggc gcacacactc ataatgattg ggtccaacgc    3660
ctctgacaga atggggatgg cgtcacttta cctagctcta attgcaacat ttaaaattca    3720
gccactcctg gctttgggat tcttcctgag gaaactgaca tctagagaaa atttattgct    3780
gggagttggg ttggccatgg cagcaacgtt acgactgcca gaggacattg aacagatggc    3840
gaatggaatt gctttggggc tcatggctct taaactgata acacaatttg aaacatacca    3900 actatgacg gcattagttt ccctaacgtg ttcaaataca attttcacgt tgactgttgc    3960
ctggagaaca gccactctga ttttagccgg aatttcgctt ttgccagtgt gccagtcttc    4020
gagcatgagg aaaacagatt ggctcccaat gactgtggca gctatgggag ctcaaccccct    4080 accacttttt attttcagtc tgaaagatac actcaaaagg agaagctggc cactgaatga    4140
gggggtgatg gcagttggac ttgtgagcat tctagctagt tctctcctta ggaatgatgt    4200
gcctatggct ggaccattag tggctggggg cttgctgata gcgtgctacg tcataactgg    4260
cacgtcagca gacctcactg tagaaaaagc agcagatgta acatgggagg aagaggccga    4320
gcaaacagga gtgtcccaca tttaatggt cacagttgat gatgatggaa caatgagaat    4380
aaaagatgac gagactgaga acatcttaac agtgcttta aaaacagcac tactaatagt    4440
atcaggcatc tttccatact ccatacccgc aacactgttg gtctggcata cttggcaaaa    4500
```

-continued

```
gcaaacccaa agatccggcg tcctatggga cgtacccagc cccccagaga cacagaaagc    4560
ggaactggaa gaaggggtct ataggatcaa acagcaagga atttttggga aaacccaagt    4620
gggggttgga gtacagaaag aaggagtttt ccacaccatg tggcatgtca caagaggggc    4680
agtgttgaca cacaatggga aaagactgga accaaactgg gctagcgtga aaaaagatct    4740
gatttcatac ggaggaggat ggagattgag tgcacaatgg aaaaggggg aggaggtgca     4800 ggttattgcc gtagagcctg ggaagaaccc aaagaacttt caaaccatgc caggcatttt    4860
tcagacaaca cagggaaa taggagcaat tgcactggat ttcaagcctg gaacttcagg      4920
atctcccatc ataaacagag agggaaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atctccatcc    5100
tgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggcccatttc acagacccag ccagtatagc    5400
ggctagaggg tacatatcaa ctcgtgtagg aatgggagag gcagccgcaa ttttcatgac    5460
agcaacaccc cctggaacag ctgatgcctt tcctcagagc aacgctccaa ttcaagatga    5520
agagagagac ataccggaac gctcatgaa ttcaggcaat gaatggatta ctgactttgt     5580
tgggaagaca gtgtggtttg tccctagcat caaagccgga aatgacatag caaactgctt    5640
gcggaaaaat ggaaaaaagg ttattcaact cagcaggaag acctttgaca cagaatatca    5700
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagacggcg aataccgcct gaagggtgag tccaggaaga ctttcgtgga    6120
actcatgagg agggggtgacc tcccagtttg gctagcccat aaagtagcat cagaagggat    6180
caaatataca gatagaaaat ggtgctttga tggagaacgt aataatcaaa ttttagagga    6240
gaatatggat gtggaaatct ggacaaagga aggagaaaag aaaaaactga gacctaggtg    6300
gcttgatgcc cgcacttatt cagatccttt agcactcaaa gaattcaagg attttgcagc    6360
tggcagaaag tcaatcgccc ttgatcttgt gacagaaata ggaagagtgc cttcacactt    6420
agcccacaga acgagaaacg ccctggataa tttggtgatg ctgcacacgt cagaacatgg    6480
cggtagggcc tacaggcatg cagtggagga actaccagaa acgatggaaa cactcttact    6540
cctgggactg atgatcttgt taacaggtgg agcaatgctc ttcttgatat caggtaaagg    6600
gattggaaag acttcaatag gactcatttg tgtaattgct tccagcggca tgttatggat    6660
ggctgatgtc ccactccaat ggatcgcatc ggctatagtc ctggagtttt ttatgatggt    6720
gttgctcata ccagaaccag aaaagcagag aactccccaa gacaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
```

```
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
ggacttgggc gtaccactat tggcactggg ttgctattca caagtgaacc cactaactct    7140
tgcagcggca gtacttttgc tagtcacaca ttatgcaatt ataggtccag gattgcaggc    7200
aaaagccacc cgtgaagctc agaaaaggac agctgctgga ataatgaaga tccaacggt    7260 ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggccttg tgtgaagttc taaccctagc cacaggacca ataacaacac tctgggaagg    7440
atcacctggg aagttctgga acaccacgat agctgtttcc atggcgaaca tctttagagg    7500
gagctattta gcaggagctg ggcttgcttt ttctatcatg aaatcagttg gaacaggaaa    7560
gagaggaaca gggtcacaag gtgaaacctt aggagaaaag tggaaaaaga aattaaatca    7620
gttatcccgg aaagagtttg acctttacaa gaaatccgga atcaccgaag tggatagaac    7680
agaagccaaa gaagggttaa aaagaggaga ataacacac catgccgtgt ccagaggcag    7740
cgcaaaactt caatggttcg tggagagaaa catggtcatt cctgaaggaa gagtcataga    7800
cctaggctgt ggaagaggag gctggtcata ttactgtgca ggactgaaaa agttacaga    7860 agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttcacca agcccaacag tggaagaaag    8040
cagaaccata agagttttga gatggttga accatggcta aagaacaacc agttttgcat    8100
taaagtattg aacccataca tgccaactgt gattgagcac ttagaaagac tacaaaggaa    8160
acatggagga atgcttgtga gaaatccact ctcacgaaac tccacgcacg aaatgtattg    8220
gatatccaat ggtacaggca atatcgtctc ttcagtcaac atggtatcca gattgctact    8280
gaacagattc acaatgacac acaggagacc caccatagag aaagatgtgg atctaggagc    8340 aggaaccga catgtcaatg cggaaccaga acacccaac atggatgtca ttggggaaag    8400
aataaaaagg atcaaagagg agcatagttc aacatggcac tatgatgatg aaaatcctta    8460
caaaacgtgg gcttaccatg gatcctatga agtaaaagcc acaggctcag cctcctccat    8520
gataaatgga gtcgtgaaac tcctcacaaa accatgggat gtggtgccca tggtgacaca    8580
gatggcaatg acagatacaa ctccattcgg ccagcaaaga gttttaaag agaaagtgga    8640 caccaggaca cctaggccca tgccaggaac aagaaaggtt atggagatca cagcggagtg    8700
gctttggagg accctgggaa ggaacaaaag acccagatta tgcacaaggg aggaattcac    8760
aaagaaggtc agaaccaacg cagctatggg cgctgtcttc acagaagaga accaatggga    8820
cagtgcgaga gctgctgttg aggacgaaga attttggaa cttgtggaca gagaacgtga    8880
actccacaaa ctgggcaagt gtggaagctg cgtttacaac atgatgggca agagagagaa    8940
aaaacttgga gagtttggta aagcaaaagg cagtagggct atatggtaca tgtggttggg    9000
agccaggtac cttgagttcg aggcgctcgg attcctcaat gaagaccact ggttctcgcg    9060
tgaaaactct tacagtggag tagaaggaga aggactgcac aagctgggat acatcttgag    9120
agatatttcc aagataccg gaggagccat gtatgctgat gacacagccg ttggacac    9180 aagaataaca gaagatgacc tgcacaatga ggaaaaaatc acacagcaga tggaccctga    9240
acacaggcag ctagcgaacg ctatattcaa gctcacatac caaaacaaag tggtcaaagt    9300
```

```
ccaacgacca actccaaagg gcacggtaat ggacatcata tctaggaaag accaaagagg   9360
cagtggacag gtgggaactt atggtctgaa cacattcacc aacatggaag cccagctaat   9420
cagacaaatg gaaggagaag gcgtgttgtc aaaggcagac ctcgagaacc cccatccgct   9480
agagaagaaa attacacaat ggttggaaac taaaggagtg gaaaggttaa aaagaatggc   9540
catcagcggg gatgattgcg ttgtgaaacc aatcgacgac agattcgcca atgccctgct   9600
tgccctgaac gatatgggaa aggttagaaa ggacatacct caatggcagc catcaaaggg   9660
atggcatgat tggcaacagg tccccttctg ctcccaccac tttcatgaat tgatcatgaa   9720
agatggaaga aagttggtag ttccctgcag accccaggac gaactaatag gaagagcgag   9780
aatctcccaa ggagcaggat ggagccttag agaaactgca tgtctaggga agcctacgc    9840 tcaaatgtgg gctctcatgt attttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtggataga  10020
ggacaatcca tggatggaag acaaaactcc agtcacaacg tgggaagatg ttccatatct  10080
agggaagaga gaagaccaat ggtgcggatc actcatagg ctcacttcca gagcaacctg   10140
ggcccagaac atactcacag caatccaaca ggtgagaagc ctcataggca atgaagagtt  10200
tctggactac atgccttcga tgaagagatt caggaaggag gaggagtcag agggagccat  10260
ttggtaaaag caggaggtaa actgtcaggc cacattaagc cacagtacgg aagaagctgt  10320
gcagcctgtg agccccgtcc aaggacgtta aagaagaag tcaggcccaa aagccacggt   10380
ttgagcaaac cgtgctgcct gtagctccgt cgtggggacg taaagcctgg gaggctgcaa  10440
accgtggaag ctgtacgcac ggtgtagcag actagtggtt agaggagacc cctcccatga  10500
cacaacgcag cagcggggcc cgagcactga gggaagctgt acctccttgc aaaggactag  10560
aggttagagg agacccccg caaacaaaaa cagcatattg acgctgggag agaccagaga   10620
tcctgctgtc tcctcagcat cattccaggc acagaacgcc agaaaatgga atggtgctgt  10680
tgaatcaaca ggttctagt                                               10699
```

<210> SEQ ID NO 42
<211> LENGTH: 10648
<212> TYPE: DNA
<213> ORGANISM: Dengue virus
<220> FEATURE:
<221> NAME/KEY: misc_feature
<222> LOCATION: (1)..(10648)
<223> OTHER INFORMATION: LAV4

<400> SEQUENCE: 42

```
agttgttagt ctgtgtggac c

```
ccttactggt caataccgaa cctgaagaca ttgattgctg gtgcaatctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacgaaat gcgatgcgta ggagtaggaa    960
acagagactt tgtggaagga gtctcaggtg gagcatgggt cgatctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taaccacggc aacaagatgt ccaacgcaag gagagcctta tctaaaagag gaacaagacc   1200
aacagtacat ctgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccacgata actcccaggt   1440
caccatcggt ggaagtcaaa ttgccggact atggagaact aacactcgat tgtgaaccca   1500
ggtctggaat tgactttaat gagatgattc tgatgaaaat gaaaagaaa acatggcttg   1560 tgcataagca atggtttttg gatctacctc taccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca gtgtttgcagg acatctcaag tgcaaagtcc   1800
gtatggagaa attgagaatc aagggaatgt catacacgat gtgttcagga aagttctcaa   1860
ttgacaaaga gatggcagaa acacagcatg ggacaacagt ggtgaaagtc aagtatgaag   1920
gtgctggagc tccgtgtaaa gtccccatag agataagaga tgtgaacaag aaaaaagtgg   1980
ttgggcgtat catctcatcc accccttggg ctgagaatac caacagtgca accaacatag   2040
agttagaacc ccccttgggg acagctacta gtgataggt gttggaaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggtttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
gggtctgtgg aattagatca accacgagc tggaaaatgt catgtggaag caaataacca   2640
acgagctaaa ttatgttctc tgggaaggag acatgacct cactgtagtg gctggggatg   2700 tgaaggggt gttgaccaaa ggcaagagag cactcacacc cccagtgaat gatctgaaat   2760
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
```

```
ctgtgcatgc tgacatgggt tattggatag agagctcaaa aaaccagacc tggcagatag    3060
agaaagcatc tcttattgaa gtgaaaacat gtctgtggcc caagacccac acattgtgga    3120
gcaatggagt gctggaaagc cagatgctca ttccaaaatc atatgcgggc ccttttttcac   3180 accacaatta ccgccagggc tatgccacgc aaaccgtggg cccatggcac ttaggcaaat    3240
tagagataga ctttggagaa tgccccggaa caacagtcgc aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaagaag agaacatggt caaatcacag gtaacggccg     3480
gacagggcac atcagaaact ttttctatgg gtctgttgtg cctgaccttg tttgtggaag    3540
aatgcttgag gagaagagtc actaggaaac acatgatatt ggttgtggtg atcactcttt    3600
gtgccatcat cctaggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctggggctaa ttttgctaaa aatagtgaca cattttgaca    3900
acacccaagt gggaaccta gcccttttcct tgaccttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtggggtt tggttagtct cttaggaagc gctcttttaa    4200
agaatgatgt ccccttttagct ggcccaatgg tggcaggagg cttacttctg gcggcttacg   4260
tgatgagtgg tagctcagca gatctgtcac tagagaaggc cgccaatgtg cagtgggatg    4320
aaatggcaga cataacaggc tcaagcccaa tcatagaagt gaagcaggat gaagatggct    4380
ctttctccat acgggacgtc gaggaaacca atatgataac ccttttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctcaaaaagc cgcactgtct gaaggagtgt acaggatcat gcaaagaggg ttatttggga    4620
aaactcaggt tggagtaggg atacacatgg aaggtgtatt tcacacaatg tggcatgtaa    4680
caagaggatc agtgatctgc catgagactg ggagattgga gccatcttgg gctgacgtca    4740
ggaatgacat gatatcatac ggtggggat ggagacttgg agacaaatgg gacaaagaag    4800
aagatgttca ggtcctcgcc atagaaccag gaaaaaatcc taaacatgtc caaacgaaac    4860
ccggcctttt caagacccta actggagaaa ttggagcagt aacattagat ttcaaacccg    4920
gaacgtctgg ttctcccatc atcaacagga aggaaaagt catcggactc tatgaaatg    4980 gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctggaaag acaaaaagaa ttcttccatc aatagtgaga gaagccttaa    5160
aaaggaggct gcgaaccttg attttggctc ccacgagagt ggtggcggcc gagatggaag    5220
aggccctacg tggactgcca atccgttatc agaccccagc tgtgaaatca gaacacacag    5280
gaagagagat tgtagacctc atgtgtcatg caaccttcac aacaagactt ttgtcatcaa    5340
ccagagttcc aaattacaac ctcatagtga tggatgaagc acatttcacc gatcccttcta   5400
```

```
gtgtcgcggc tagaggatac atctcgacca gggtggaaat gggagaggca gcagccatct    5460
tcatgaccgc aaccccctccc ggagcgacag atccctttcc ccagagcaac agcccaatag   5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga agaaagtta tccagttgag taggaaaacc tttgatacag     5700
agtatccaaa aacgaaactc acggactggg attttgtggt cactacagac atatctgaaa   5760
tgggggccaa ttttagagct gggagagtga tagaccctag gagatgcctc aagccagtta   5820
tcctaacaga tgggccagag agagtcattt tagcaggtcc tattccagtg actccagcaa    5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac accccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgccc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatgggtt tgataaccat tgcggtggct agtggcttgt   6660
tctgggtagc agaaattcaa ccccagtgga tagcggcctc aatcatacta gagttttttc   6720
tcatggtact gttgataccg gaaccagaaa aacaaaggac cccacaagac aatcaattga   6780
tctacgtcat attgaccatt ctcaccatta ttggtctcat agcagccaac gagatggggc   6840
tgattgaaaa aacaaaaacg gattttgggt tttaccaggt aaaaacagaa accaccatcc   6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca ggcggccgtc ctaatggggc ttgaaaaagg atggccgctc cacagaatgg   7080
acctcggtgt gccgctgtta gcaatgggat gctattctca agtgaaccca caaactttga   7140
cagcatcctt agtcatgctt tcagtccatt atgcaataat aggtccagga ttgcaggcaa   7200
aagccacaag agaggcccag aaaaggacag ctgctgggat catgaaaaac ccacgcgtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggcttctgt tgaagtcttg actttggcca caggaccaat cttgacccttg tgggagggca   7440 acccgggaag gttttggaac acgaccatag ccgtatccac cgccaacatt tcaggggaa    7500 gttacctggc gggagctgga ctggcttttt cactcataaa gaatgyacaa accccctagga   7560 ggggaactgg gaccacagga gagacactgg gagagaagtg gaagagacag ctaaactcat   7620
takacagaaa agagtttgaa gagtatataaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
```

```
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga acattgtga gctctgtgaa cacaacatca agatgttgt    8280 tgaacaggtt cacaacaagg cataggaaac ccacttatga aaggacgta gatcttgggg    8340 caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg ggcgtatcat ggaagctatg aagctccttc gacaggctct gcatcctcca   8520
tggtgaacgg ggtagtaaaa ctgctaacaa aaccttggga tgtggttcca atggtgaccc   8580
agttagccat gacagacaca accccttttg ggcaacaaag agtgttcaaa gagaaggtgg   8640
ataccagaac accacaacca aaacccggta cacgaatggt tatgaccacg acagccaatt   8700
ggctgtgggc cctccttggg aagaagaaaa atcccagact gtgcacaagg aaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctacaa catgatggga aaacgtgaga   8940
aaaagttagg agagttttggc agagccaagg gaagccgagc aatctggtac atgtggctgg   9000
gagcgcggtt tctggaattt gaagccctgg gttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgcacagca ggctgggaca    9180 caagaatcac tgaggatgac cttcaaaatg aagaactgat cacggaacag atggcccccc   9240
accacaagat cctagccaaa gccattttca actaaccta tcaaaacaaa gtggtgaaag    9300
tcctcagacc cacaccgaga ggagcggtga tggatatcat atccaggaaa gaccaaagag   9360
gtagtggaca agttggaaca tatggttgaa acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtgtgt cgacaggtta aagaggatgg   9540
caatcagtgg agacgattgc gtggtgaagc ccctggatga gaggtttggc acttccctcc   9600
tcttcttgaa cgacatggga aaggtgagga agacattcc gcagtgggaa ccatctaagg   9660
gatggaaaaa ctggcaagag gttcctttt gctcccacca cttccacaag atcttcatga   9720
aggatggccg ctcactagtt gttccatgta gaaaccagga tgaactgata gggagagcca   9780
gaatctcgca gggggctgga tggagcttaa gagaaacagc ctgcctgggc aaagcttacg   9840
cccagatgtg gtcgctcatg tacttccaca gaagggatct gcgtttagcc tccatggcca   9900
tatgctcagc agttccaacg gaatggtttc caacaagcag aacaacatgg tcaatccacg   9960
ctcatcatca gtggatgacc actgaagata tgctcaaagt gtggaacaga gtgtggtag   10020 aagacaaccc taatatgact gacaagactc cagtccattc gtgggaagat atacc ttacc  10080 tagggaaaag agaggatttg tggtgtggat ccctgattgg actttcttcc agagccacct   10140
gggcgaagaa cattcacacg gccataaccc aggtcagaaa cctgatcgga aaagaggaat   10200
```

| | | | | |
|---|---|---|---|---|
| acgtggatta | catgccagta | atgaaaagat | acagcgctcc | ttcagagagt gaaggagttc 10260 |
| tgtaattacc | aacaacaaac | accaaaggct | attgaagtca | ggccacttgt gccacggctt 10320 |
| gagcaaaccg | tgctgcctgt | agctccgcca | ataatgggag | gcgtgaaatc cctagggagg 10380 |
| ccatgcgcca | cggaagctgt | acgcgtggca | tattggacta | gcggttagag gagacccctc 10440 |
| ccatcactga | caaaacgcag | caaaaggggg | cccgaagcca | ggaggaagct gtactcctgg 10500 |
| tggaaggact | agaggttaga | ggagaccccc | ccaacacaaa | aacagcatat tgacgctggg 10560 |
| aaagaccaga | gatcctgctg | tctctgcaac | atcaatccag | gcacagagcg aagcaagatg 10620 |
| gattggtgtt | gttgatccaa | caggttct | | 10648 |

What is claimed is:

1. An isolated nucleic acid which comprises the DNA sequence SEQ ID NO: 1 or its equivalent RNA sequence.

2. The isolated nucleic acid according to claim 1 wherein the deoxythymidines are replaced by uridines.

3. The isolated nucleic acid according to claim 1 wherein the sequence encodes the dengue serotype 2 virus (VDV2) strain.

4. An isolated nucleic acid encoding the polyprotein having the sequence SEQ ID NO: 2.

* * * * *